United States Patent
Evans

(10) Patent No.: US 11,105,744 B2
(45) Date of Patent: Aug. 31, 2021

(54) METHOD AND SYSTEM INCORPORATING BEAM SHAPING OPTICS AND BEAM STABILIZATION

(71) Applicant: Inguran, LLC, Navasota, TX (US)

(72) Inventor: Kenneth Michael Evans, College Station, TX (US)

(73) Assignee: Inguran, LLC, Navasota, TX (US)

( * ) Notice: Subject to any disclaimer, the term of this patent is extended or adjusted under 35 U.S.C. 154(b) by 573 days.

(21) Appl. No.: 16/039,629

(22) Filed: Jul. 19, 2018

(65) Prior Publication Data

US 2019/0025212 A1    Jan. 24, 2019

Related U.S. Application Data

(60) Provisional application No. 62/534,508, filed on Jul. 19, 2017.

(51) Int. Cl.

| G01N 21/64 | (2006.01) |
|---|---|
| G01N 15/14 | (2006.01) |
| C12N 5/071 | (2010.01) |
| C12Q 1/6879 | (2018.01) |
| G02B 27/09 | (2006.01) |
| G01N 15/10 | (2006.01) |
| H01S 3/0941 | (2006.01) |

(52) U.S. Cl.
CPC ....... *G01N 21/6428* (2013.01); *C12N 5/0612* (2013.01); *C12Q 1/6879* (2013.01); *G01N 15/1434* (2013.01); *G01N 15/1459* (2013.01); *G02B 27/0966* (2013.01); *G01N 2015/1006* (2013.01); *G01N 2015/145* (2013.01); *G01N 2015/149* (2013.01); *G01N 2021/6439* (2013.01); *G01N 2201/06113* (2013.01); *H01S 3/0941* (2013.01)

(58) Field of Classification Search
None
See application file for complete search history.

(56) References Cited

U.S. PATENT DOCUMENTS

| 4,498,766 | A | 2/1985 | Unterleitner |
| 4,545,677 | A | 10/1985 | Chupp |
| 5,760,900 | A | 6/1998 | Ito |
| 5,858,667 | A | 1/1999 | Dertinger |
| 6,275,777 | B1 | 8/2001 | Shimizu |
| 7,311,476 | B2 | 12/2007 | Gilbert |
| 7,371,517 | B2 | 5/2008 | Evans |
| 8,502,976 | B2 | 8/2013 | Sharpe et al. |
| 9,057,676 | B2 | 6/2015 | Sharpe |
| 2004/0042008 | A1 | 3/2004 | Wagner |
| 2006/0256335 | A1 | 11/2006 | Chen |
| 2010/0122359 | A1* | 5/2010 | Suh ................. C12N 15/873 800/8 |
| 2011/0001963 | A1 | 1/2011 | Durack |
| 2011/0008767 | A1 | 1/2011 | Durack |
| 2012/0307244 | A1* | 12/2012 | Sharpe ............... G01N 15/1484 356/338 |
| 2014/0092378 | A1 | 4/2014 | Sharpe |
| 2014/0220620 | A1* | 8/2014 | Durack ............... A01N 1/0284 435/34 |
| 2014/0264097 | A1* | 9/2014 | Heanue ............... G01N 15/1459 250/576 |
| 2014/0273192 | A1* | 9/2014 | Sharpe ............... G01N 15/1459 435/288.7 |
| 2015/0114093 | A1 | 4/2015 | Appleyard |
| 2016/0326489 | A1 | 11/2016 | Durack |

FOREIGN PATENT DOCUMENTS

| JP | 02013830 A | 1/1990 |
| WO | 2001/40765 A2 | 6/2001 |
| WO | 01/85913 A2 | 11/2001 |
| WO | 2004/088283 A2 | 10/2004 |
| WO | 2004/104178 A2 | 12/2004 |
| WO | 20101148332 A2 | 12/2010 |
| WO | 2012/155106 A2 | 11/2012 |
| WO | 2014/142924 A2 | 9/2014 |

OTHER PUBLICATIONS

Australian Office Action dated Jan. 21, 2021 in related AU Appl. No. 2018302191.
New Zealand Office Action dated Nov. 27, 2020 in related NZ Appl. No. 760907.
Australian Office Action dated Jul. 2, 2020 in related AU Appl. No. 2018302191.
Amann, R.P. "Issues Affecting Commercialization of Sexed Sperm." Theriogenology 52: pp. 1441-1457, 1999.
Johnson, L. A. "Advances in Gender Preselection in Swine." Journals of Reproduction and Fertility Ltd. pp. 255-266 1997.
Johnson, L.A., "Sex Preselection: High-Speed Flow Cytometric Sorting of X and Y Sperm for Maximum Efficiency." Theriogenology 52: pp. 1323-1341, 1999.
Rens et al. "Slit-Scan Flow Cytometry for Consistent High Resolution DNA Analysis of X- and Y-Chromosome Bearing Sperm." Cytometry 25: pp. 191-199. 1996.
Shapiro, Howard "Practical Flow Cytometry" Third Edition. Wiley-Liss pp. 103-104.2003. 1995.
Sharpe et al. "Advances in Flow Cytometry for Sperm Sexing." Theriogenology 71: pp. 4-10, 2009.
Johnson, L.A., "Sex Preselection by Flow Cytometric Separation of X and Y Chromosome Bearing Spermatozoa Based on DNA Difference: a Review." Reprod. Fertil. Dev. 7:893-901 (1995).

(Continued)

*Primary Examiner* — Susan M Hanley

(74) *Attorney, Agent, or Firm* — Ryan Christensen; Hashim Rahman

(57) ABSTRACT

This disclosure pertains to analytical instruments and related methods incorporating beam shaping optics for differentiating very bright and closely related signals over a wide range of operating conditions with an improved and uniform performance.

37 Claims, 28 Drawing Sheets

(56) References Cited

OTHER PUBLICATIONS

Johnson, L.A., et al., "Modification of a Laser-Based Flow Cytometer for High-Resolution DNA Analysis of Mammalian Spermatozoa" Cytometry 7, pp. 268-273 (1986).
International Search Report and Written Opinion dated Oct. 5, 2018 issued in related International Appl. No. PCT/US2018/042835.
Shapiro, Howard M. et al., "Multistation Multiparameter Flow Cytometry: Some influences of Instrumental Factors on System Performance", 1983, pp. 11-19, 4, Allan R. Liss, Inc.
Shapiro, Howard "Practical Flow Cytometry" Fourth Edition. Wiley-Liss pp. 136-138. 2003.
Steinkamp, John A. "Improved Multilaser/Multiparameter Flow Cytometer for Analysis and Sorting of Cells and Particles" Review of Scientific instruments 62, 2751-2764. (1991).
Indian Office Action dated Apr. 13, 2021 in related IN Appl. No. 202037005538.
Canadian Office Action dated Apr. 19, 2021 in related CA Appl. No. 3,068,874.
New Zealand Office Action dated Jun. 9, 2021 in related NZ Appl. No. 760907.

\* cited by examiner

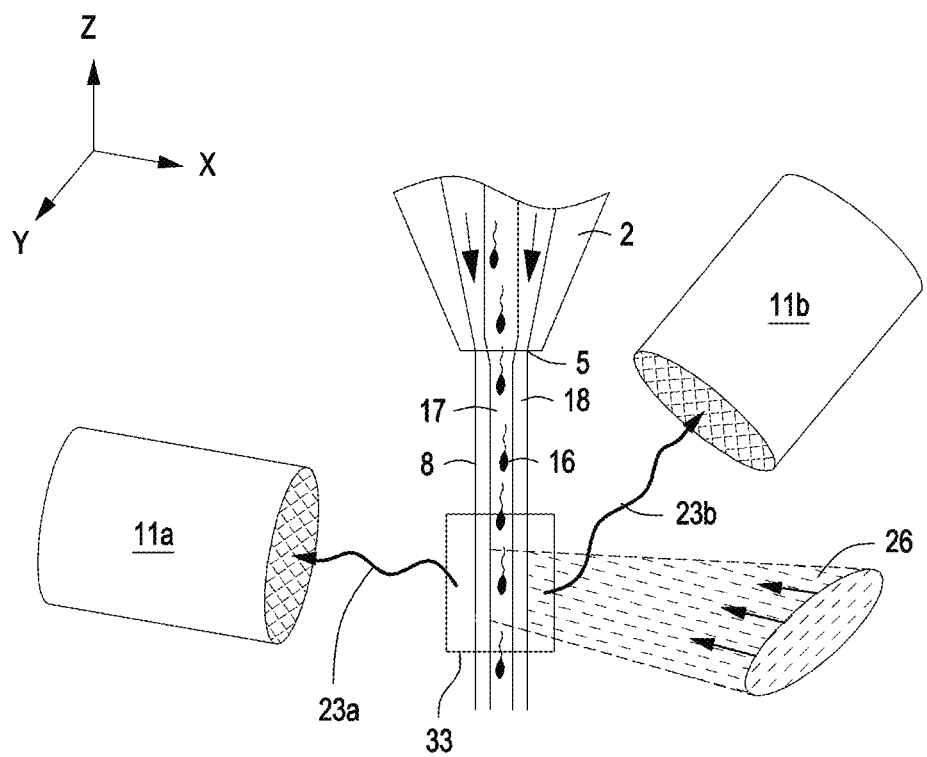
FIG. 2
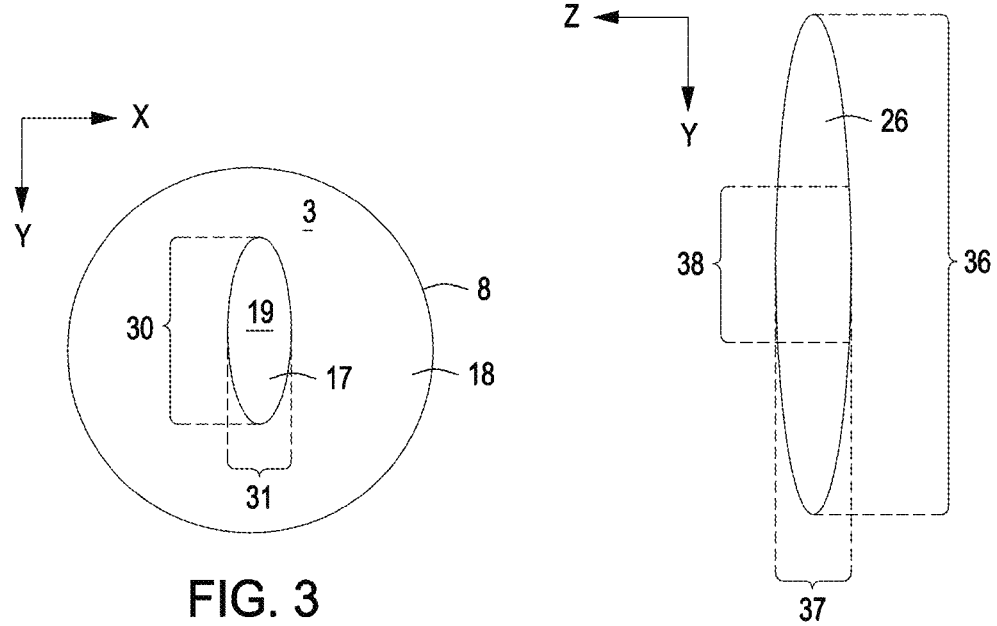
FIG. 3
FIG. 4

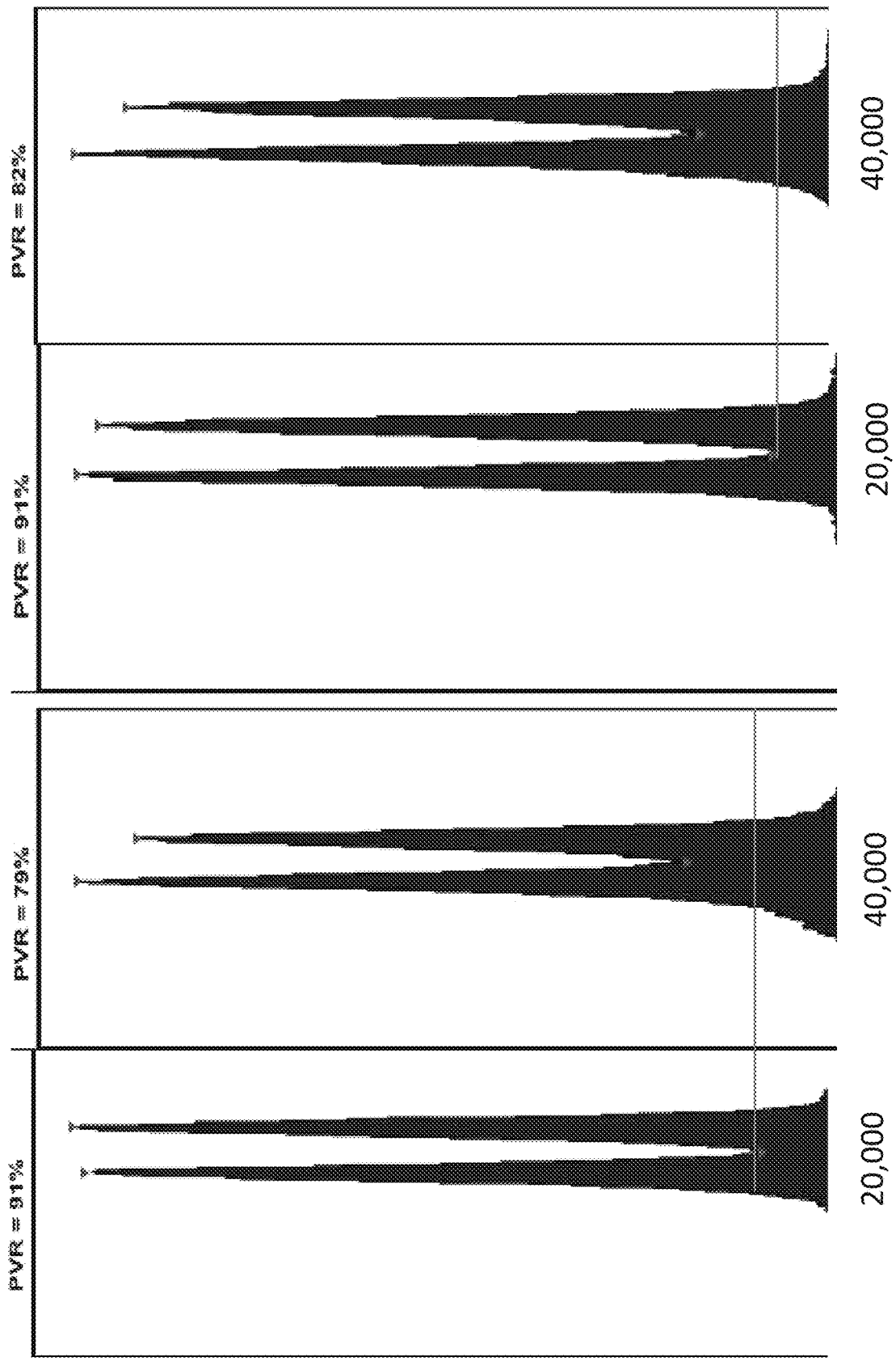

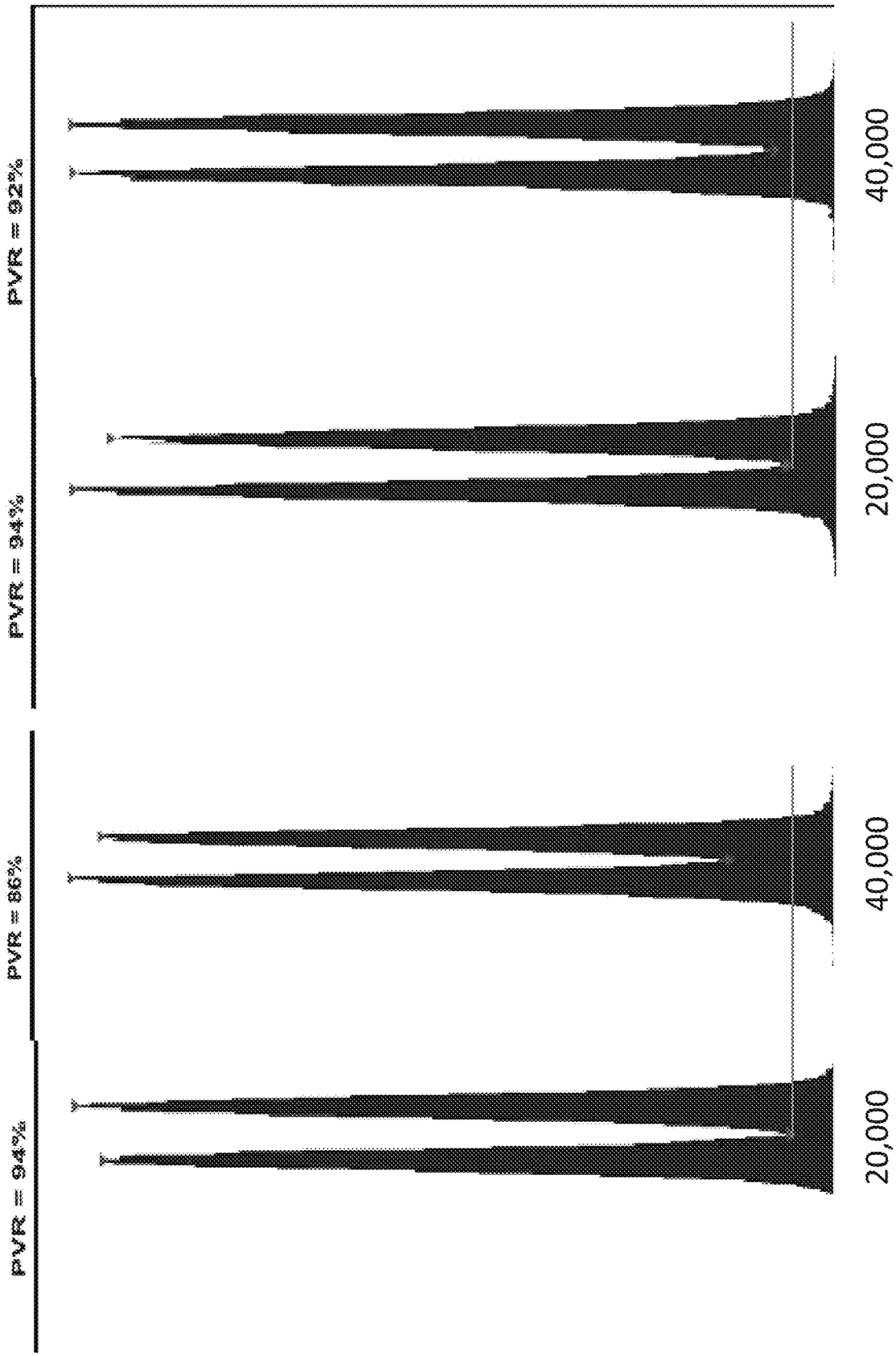

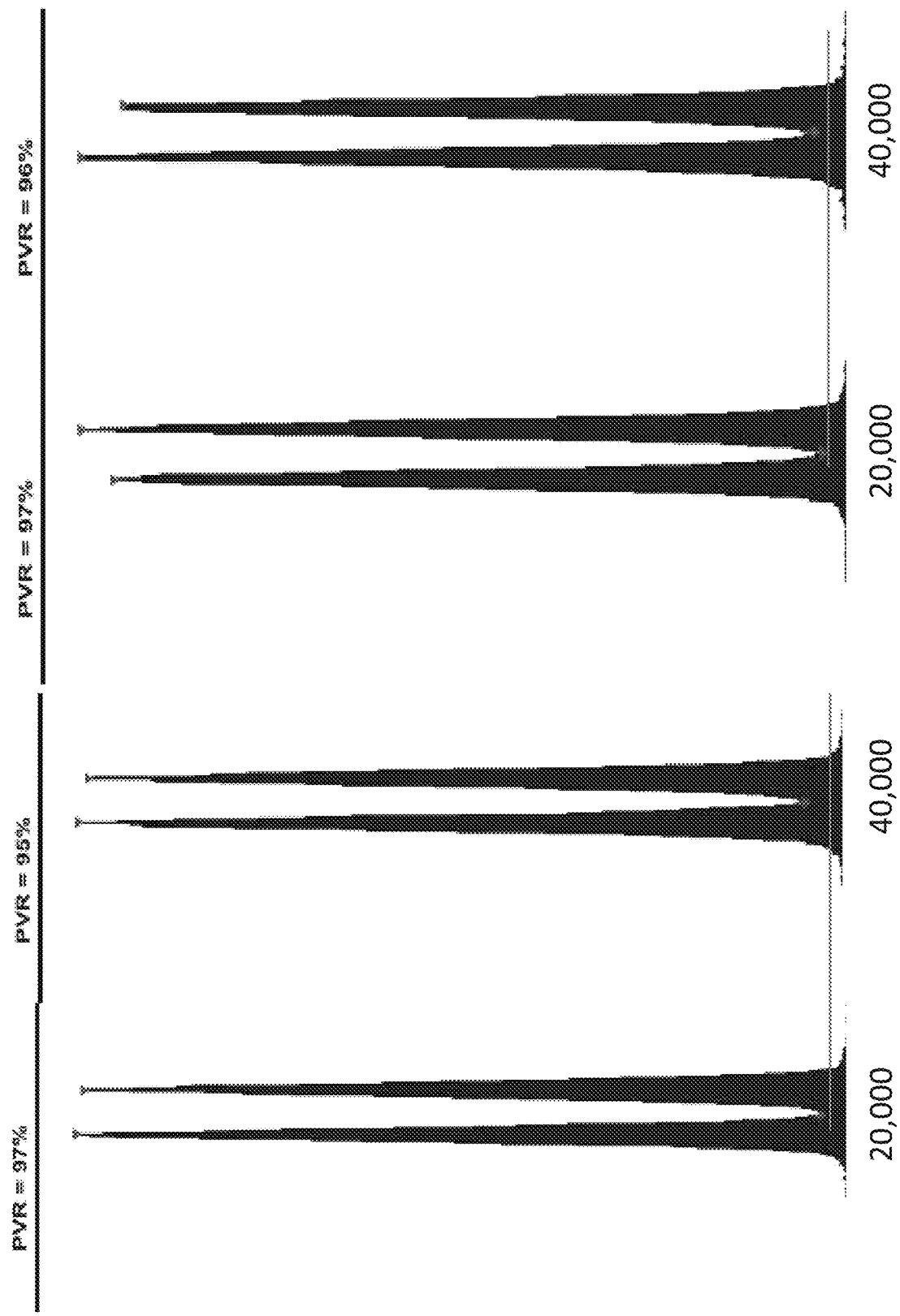

FIG. 26

Stability (10 = Stable, 1 = Unstable)

| Beam Width | 100mW | 150mW | 200mW | 250mW |
|---|---|---|---|---|
| 70 um | 7 | 8 | 10 | 10 |
| 80 um | 8 | 8 | 10 | 10 |
| 90 um | 9 | 9.5 | 10 | 10 |
| 100 um | 10 | 10 | 10 | 10 |
| 110 um | 10 | 10 | 10 | 10 |

FIG. 27

Ease of Alignment (10 = Easy, 1 = Difficult)

| Beam Width | 100mW | 150mW | 200mW | 250mW |
|---|---|---|---|---|
| 70 um | 4 | 5 | 7 | 7 |
| 80 um | 4 | 5 | 7 | 8 |
| 90 um | 8 | 9 | 9 | 10 |
| 100 um | 9 | 9 | 10 | 10 |
| 110 um | 8.5 | 9 | 10 | 10 |

FIG. 28

PVR

| | 100mW | | 150mW | | 200mW | | 250mW | |
|---|---|---|---|---|---|---|---|---|
| | 20,000 | 40,000 | 20,000 | 40,000 | 20,000 | 40,000 | 20,000 | 40,000 |
| 80 um | 76 | 63 | 84 | 65 | 84 | 68 | 89 | 69 |
| 90 um | 91 | 79 | 91 | 82 | 97 | 86 | 96 | 92 |
| 100 um | 91 | 89 | 96 | 92 | 94 | 91 | 93 | 91 |
| 110 um | 94 | 86 | 94 | 92 | 97 | 95 | 97 | 96 |

QC Results:

| | | Visual Motility | | Analytical Sorter | | | | IVOS II | | | |
|---|---|---|---|---|---|---|---|---|---|---|---|
| | | | | 0 HR | | 3 HR | | 0 HR | | 3 HR | |
| | | 0 Hour | 3 Hour | Viable | P1A | Viable | P1A | MOTILE | PROG | MOTILE | PROG |
| Pre-freeze | Vanguard | 75 | 75 | 77.2 | 88.6 | 70.1 | 82.5 | 70.0 | 58.7 | 70.0 | 64.4 |
| | Coherent | 75 | 73 | 76.5 | 88.6 | 70.2 | 81.6 | 72.5 | 66.2 | 72.5 | 54.9 |
| Post-freeze | Vanguard | 68 | 64 | 64.0 | 66.1 | 52.9 | 71.0 | 59.2 | 42.5 | 59.2 | 30.2 |
| | Coherent | 65 | 56 | 62.3 | 82.9 | 50.0 | 66.5 | 59.9 | 50.4 | 59.9 | 26.6 |

| | Other | | |
|---|---|---|---|
| | Bact | Conc | Purity |
| Vanguard | 0 | 4.2 | 91.7 |
| Coherent | 0 | 3.9 | 89.3 |

METHOD AND SYSTEM INCORPORATING BEAM SHAPING OPTICS AND BEAM STABILIZATION

This application claims the benefit of U.S. Patent Application No. 62/534,508 filed Jul. 19, 2017. The entire disclosure of which is incorporated herein by reference.

FIELD

The technology of this disclosure pertains generally to methods and systems for analyzing and/or sorting particles, and more particularly to such methods and systems incorporating improved beam shaping optics and beam stabilization for use in the analysis and/or sorting of sperm.

BACKGROUND

An analytical instrument, such as a flow cytometer, may be used to sort a variety of cells or particles based on detectable characteristics. In one specialized application such flow cytometers have been modified to differentiate stained sperm into one or more enriched subpopulations, such as an X- or Y-chromosome bearing sperm subpopulations based on small variations in chromosomal DNA.

One modification required to render a flow cytometer suitable for analyzing and/or subsequently sorting sperm based on small variations in DNA content, is that the beam shaping optics are adapted to produce an elliptical beam spot. However, prior modifications fail to achieve stable resolution at a variety of laser powers or at a variety of throughput speeds. Indeed, previously unidentified deficiencies exist with current beam shaping optics employed in commercial sex sorting with flow cytometers.

Accordingly, a need exists to employ beam shaping optics in analytical instruments, including flow cytometers that achieves a beam profile capable of achieving high resolution at a variety of beam powers and event rates.

SUMMARY

A broad object of the present disclosure is to provide an analytical system with improved performance over a number of varied operating conditions, in particular for the purpose of differentiating very bright and closely related signals. In order to accomplish such broad objectives the present invention broadly relates to analytical instruments incorporating beam shaping optics having certain properties.

Certain embodiments relate to an analytical instrument for sperm having a flow channel that receives a sheath fluid and a sample fluid having at least one sperm to be analyzed and that creates a coaxial flow of a fluid stream having an inner core stream of the sample fluid and an outer stream of the sheath fluid. The analytical instrument also includes a laser that produces a laser beam and beam shaping optics that shape the laser beam to have a beam width and a beam height at an interrogation location. The beam shaping optics shape the laser beam for interrogating the at least one sperm to be analyzed at the interrogation location and substantially match a center portion of the beam width to an inner core stream width facing the laser. The analytical instrument also includes a beam path along which the laser beam traverses between the laser and the beam shaping optics, at least one detector that generates a signal in response to electromagnetic radiation from the interrogation location, and an analyzer that receives the signal from the at least one detector.

Certain other embodiments relate to an analytical instrument for sperm having a flow channel that receives a sheath fluid and a sample fluid having at least one sperm to be analyzed and that creates a coaxial flow of a fluid stream having an inner core stream of the sample fluid and an outer stream of the sheath fluid. Such analytical instruments also include a laser that produces a laser beam and beam shaping optics that shape the laser beam to a have a beam height and a beam width. The beam width of the shaped or modified laser beam being in a range of about 130 µm to about 70 µm and having a beam width to beam height ratio between 7:1 and 3:1 at an interrogation location. The beam shaping optics may be configured to shape the laser beam for interrogating the at least one sperm to be analyzed at the interrogation location. The analytical instrument also includes a beam path along which the laser beam traverses between the laser and the beam shaping optics, at least one detector that generates a signal in response to electromagnetic radiation at the interrogation location, and an analyzer that receives the signal from the at least one detector.

One embodiment relates to a method of generating a population of sperm having a skewed sex ratio of viable sperm. Such a method may include the step of creating a coaxial flow of a fluid stream, where the coaxial flow is formed from an inner core stream of a sample fluid having differing orthogonal dimensions transverse to the coaxial flow and an outer stream of a sheath fluid. Such a method may further includes the steps of modifying a laser beam from a laser into a laser beam pattern having a beam height and a beam width, substantially matching an inner core stream width facing the laser to a center portion of the beam width, interrogating the sperm in the core stream with the laser beam pattern, detecting a response to the interrogation of the sperm, generating at least one signal based on the detected response, and classifying a sex differentiation characteristic of the sperm based on the at least one signal.

Another embodiment relates to generating a population of sperm having a skewed sex ratio of viable sperm. Such a method may include the step of creating a coaxial flow of a fluid stream, where the coaxial flow is formed from an inner core stream of a sample fluid and an outer stream of a sheath fluid. The method may further include modifying a laser beam into a laser beam pattern having a beam width in a range of about 130 µm to about 70 µm and having a beam width to beam height ratio between 7:1 and 3:1. Such a method may further include the steps of interrogating the sperm in the core stream with the laser beam pattern, detecting a response to the interrogation of the sperm, generating at least one signal based on the detected response, and classifying a sex differentiation characteristic of the sperm based on the at least one signal.

Still another embodiment relates to a multichannel analytical instrument. Such an instrument may include two or more flow channels, each flow channel receiving a sheath fluid and a sample fluid having at least one sperm to be analyzed that creates a coaxial flow of a fluid stream having an inner core stream of the sample fluid and an outer stream of the sheath fluid. The multichannel analytical instrument may also include a laser associated with each flow channel and beam shaping optics associated with each flow channel. The beam shaping optics may produce a uniform beam shape from the laser associated with the flow channel and provide a uniform beam shape at each flow channel and substantially identical performance at each flow channel. The analytical instrument may also include a beam path from each laser to the associated flow channel, where there is no overlap in the beam paths as well as at least one detector that generates a signal in response to the interrogated at least one sperm and an analyzer that receives the signal from the at least one detector.

Additional embodiments relate to a method of generating a population of sperm having a skewed sex ratio of viable sperm. Such a method may employ, for example, first and second coaxial flows of a fluid stream, first and second inner core streams, first and second outer streams, first and second laser beams generated along first and second laser beam paths that do not overlap. In such embodiments, the method includes modifying the first laser beam and the second laser beam to each have a beam height and beam width, interrogating the sperm in the first inner core stream with the first modified beam and interrogating the sperm in the second inner core stream with the second modified laser beam, detecting a response to the interrogation of the sperm with the first modified beam and detecting a response to the interrogation of the sperm with the second modified laser beam, generating at least one first signal based on the detected response to the interrogation of the sperm with the first modified laser and generating at least one second signal based on the detected response to the interrogation of the sperm with the second modified laser beam, and classifying a sex differentiation characteristic of the sperm in the first inner core stream based on the at least one first signal and classifying a sex differentiation characteristic of the sperm in the second inner core stream based on the at least one second signal.

Yet another embodiment relates to an analytical instrument for sperm including a flow channel that receives a sheath fluid and a sample fluid having at least one sperm to be analyzed and that creates a coaxial flow of a fluid stream having an inner core stream of the sample fluid and an outer stream of the sheath fluid as well as a laser that produces a laser beam. Such an embodiment may also include beam shaping optics that shape the laser beam to have a beam width and a beam height at an interrogation location, where the beam shaping optics provide substantially similar performance at event rates between 5,000 events per second and 65,000 events per second. The method may further include a beam path along which the laser beam traverses between the laser and the beam shaping optics, at least one detector that generates a signal in response to electromagnetic radiation from the interrogation location, and an analyzer that receives the signal from the at least one detector.

Another embodiment relates to a method of generating a population of sperm having a skewed sex ratio of viable sperm that includes the step of creating a coaxial flow of a fluid stream having an inner core stream of a sample fluid having differing orthogonal dimensions transverse to the coaxial flow and an outer stream of a sheath fluid. Such a method may also include the step of modifying a laser beam into a laser beam pattern that provides substantially similar sperm sorting resolution at event rates between 5,000 events per second and 65,000 events per second, where the laser beam pattern has a beam width and a beam height. The method may also include the steps of interrogating the sperm in the core stream with the laser beam pattern, detecting a response to the interrogation of the sperm, generating at least one signal based on the detected response, and classifying a sex differentiation characteristic of the sperm based on the at least one signal.

BRIEF DESCRIPTION OF DRAWINGS

FIG. 2 shows a second view of an analytical instrument according to an embodiment of the present disclosure.

FIG. 3 shows a cross sectional view of the fluid stream at an interrogation location.

FIG. 4 shows a cross sectional view of a laser beam at the interrogation location.

FIG. 14 shows a comparison between histograms of resulting sorting resolutions from use of a 90 μm width beam profile.

FIG. 15 shows a comparison between histograms of resulting sorting resolutions from use of a 90 μm width beam profile.

FIG. 20 shows a comparison between histograms of resulting sorting resolutions from use of a 100 μm width beam profile.

FIG. 21 shows a comparison between histograms of resulting sorting resolutions from use of a 100 μm width beam profile.

FIG. 22 shows a comparison between histograms of resulting sorting resolutions from use of a 110 μm width beam profile.

FIG. 23 shows a comparison between histograms of resulting sorting resolutions from use of a 110 μm width beam profile.

FIG. 24 shows a comparison between histograms of resulting sorting resolutions from use of a 110 μm width beam profile.

FIG. 25 shows a comparison between histograms of resulting sorting resolutions from use of a 110 μm width beam profile.

FIG. 26 shows laser beam stability results from testing a continuous wave laser at various laser powers and various beam profile widths.

FIG. 27 shows ease of alignment results from testing a continuous wave laser at various laser powers and various beam profile widths.

FIG. 28 shows PVR results at different event rates from testing a continuous wave laser at various laser powers and various beam profile widths.

FIG. 38 shows a table that compares quality control results of pre- and post-frozen sperm that were previously sorted by a sorting system including a Coherent Genesis continuous wave laser or a Vanguard pulsed laser.

FIG. 39 shows a table that compares PVR results from use of a Vanguard pulsed laser and a Coherent Genesis continuous wave laser in a sorting system across increasing event rates.

Figure 1:
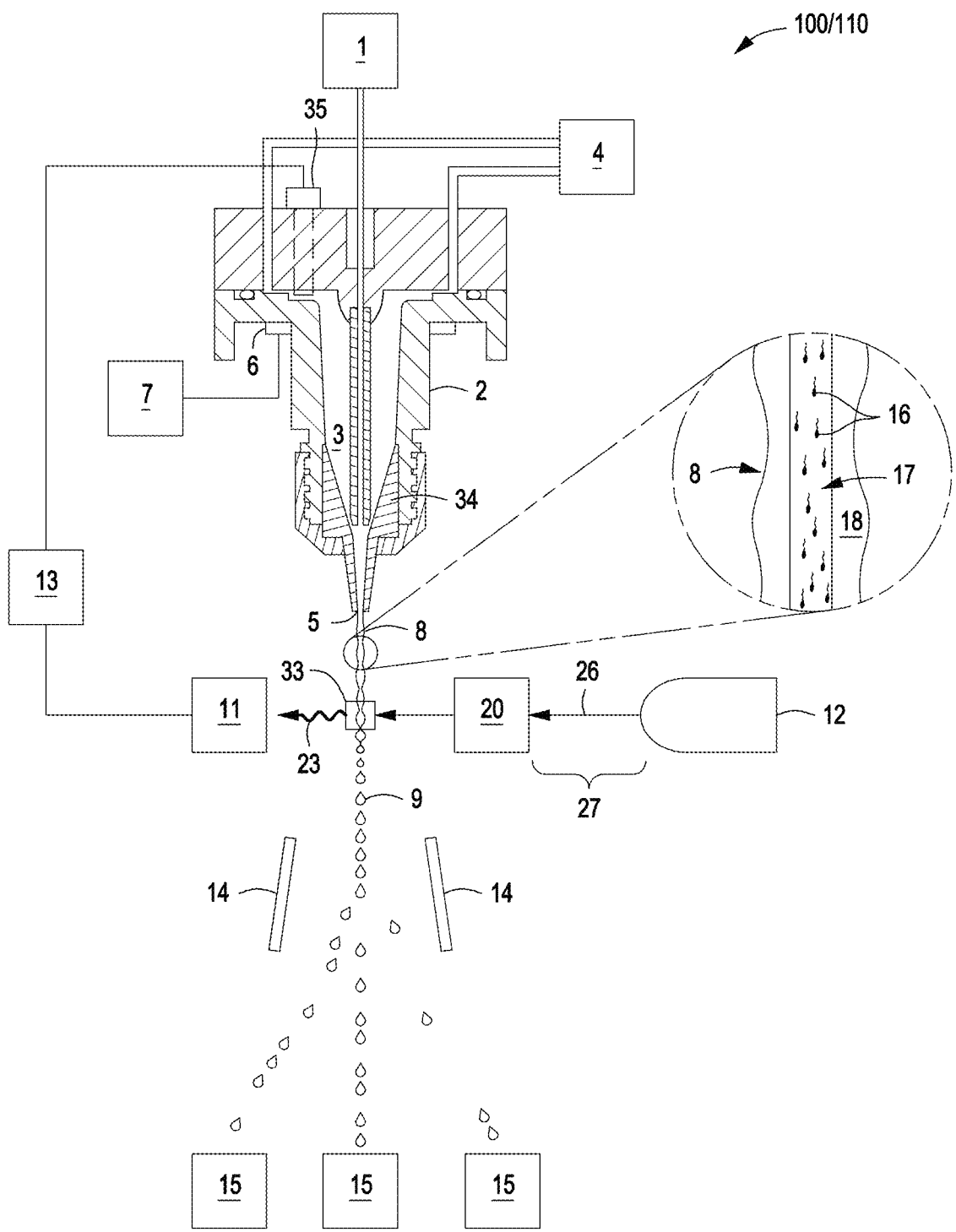
FIG. 1 shows a partial schematic of an analytical instrument according to an embodiment of the present disclosure.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

DETAILED DESCRIPTION

Embodiments of the present disclosure will be described below with reference to the figures. Like elements in the various figures are denoted by like reference numerals for consistency. In general, embodiments disclosed herein relate to apparatus and methods that employ beam shaping optics and beam stabilization for use in sperm sorting applications.

FIG. 1 depicts a partial schematic representation of an analytical instrument 110 according to an embodiment of the present disclosure. In some embodiments, the analytical instrument 110 facilitates sex sorting sperm into one or more enriched subpopulations of X- or Y-chromosome bearing sperm, checking sorted purity, or checking for a variety of stains or stain conditions. According to some embodiments, the analytical instrument 110 may comprise a flow cytometer 100. According to other embodiments, however, the analytical instrument 110 may comprise a microfluidic chip. In the non-limiting example shown in FIG. 1, the analytical instrument 110 is a flow cytometer 100 of the droplet generating type. Certain inventive features described with respect to the illustrated example have additional utility that is applicable to other devices and systems.

A flow cytometer 100, such as the one shown in FIG. 1, measures quantifiable differences in light emitted from, or reflected from, particles or cells in response to an excitation, such as by a laser 12. In accordance with embodiments describe herein, the flow cytometer 100 can differentiate X- and the Y-chromosome bearing sperm 16 based on DNA content. As used throughout, the term "sperm" may refer to the singular case and plural case as dictated by the context of its use.

The only commercially practiced sperm sorting technique relies on the differences in nuclear DNA content of X-chromosome bearing sperm and Y-chromosome bearing sperm. Detecting such a difference requires the use of a DNA selective dye (e.g., a fluorochrome such as Hoechst 33342) that stoichiometrically associated with the nuclear DNA of sperm. In bovids, for example, the X-chromosome bearing sperm has about 3.8% more nuclear DNA than the Y-chromosome bearing sperm. Thus, by detecting the amount of fluorescence emitted in properly oriented sperm by the associated fluorochrome in response to excitation with a laser 12, it is possible to differentiate between X-chromosome bearing sperm and Y-chromosome bearing sperm. Moreover, by detecting the amount of fluorescence emitted by the bound fluorochrome upon interrogation of the sperm by the laser 12, it is possible to check for any number of stains or stain conditions within the scope of the present disclosure.

A flow cytometer 100 suitable for such a technique includes fluidics capable of delivering oriented sperm individually to a precise location for excitation with the laser 12, as well as for facilitating the physical separation of selected sperm 16. The flow cytometer 100 includes a particle source or cell source 1 of sample fluid 19, which supplies at least one particle, or at least one cell, such as sperm that has been stained with a fluorochrome for analysis and/or for sorting. Sample fluid containing sperm are supplied from the sample source 1 and deposited within a flow channel 2. In FIG. 1, the depicted flow channel 2 may also be characterized as a nozzle, but other systems having closed channels may also benefit from certain inventive aspects of the instance disclosure. Sheath fluid 3 is likewise supplied from a sheath fluid source 4 and deposited within the flow channel 2. The respective inlets (unnumbered) for the sheath fluid 3 and the sample fluid 19 are arranged to allow a laminar flow of both fluids in a coaxial fluid stream 8. The flow channel 2 of the flow cytometer 100 creates a coaxial flow of a fluid stream 8, which includes an inner core stream 17 of sample fluid (sometimes referred to herein as just a "core stream"), and an outer stream 18 of the sheath fluid 3. The inner core stream 17 is illustrated containing sperm 16, which have paddle shaped sperm heads and extending tails. Further, the flow channel 2 allows the sperm 16 to mostly line up single file within the inner core stream 17, and to assume proper orientation for analysis and/or sorting. In particular, the illustrated flow channel 2, includes an orienting nozzle tip 34, which hydrodynamically biases sperm towards a uniform orientation as sperm exit the orifice 5. Examples of suitable flow cytometer systems for use with the present invention and in particular, suitable orienting nozzle tips for sorting sperm are described in more detail in International Patent Publications WO2001/40765, WO2001/085913, and WO 204/088283.

An oscillator control 7 may be establish pressure waves within the flow channel 2 by varying the frequency and amplitude of an oscillator 6. Those pressure waves are transmitted to the fluids exiting the flow channel 2 at the orifice 5 causing the fluid stream 8 to eventually and regularly forms droplets 9. Sperm 16 within the sample fluid 19 in the inner core stream 17 of the fluid stream 8 become entrain within the droplets as they form. While a droplet 9, particularly a droplet 9 targeted for sorting, may contain an individual sperm, it can be appreciate that a droplet 9 may also contain one or more sperm 16. In some embodiments, such as an embodiment employing an ablation laser, the oscillator 6 and the oscillator controller 7 may not be necessary, as there may not be a need to form droplets 9.

Still referring to FIG. 1, after the fluid stream 8 exits the orifice 5 of flow channel 2, sperm 16 within the inner core stream 17 are excited at an interrogation location 33 with a laser beam 26 produced by a 12. According to one or more embodiments, the laser 12 may be a pulsed laser, such as a Vanguard 355-350 (available from Spectra-Physics, Santa Clara, Calif.), or a continuous wave laser, such as a smaller footprint Genesis CX-355 laser (available from Coherent Inc., Santa Clara Calif.), or any device that delivers electromagnetic radiation to biological or non-biological particles at a prescribed wavelength and power. As shown in FIG. 1, the laser 12 produces electromagnetic radiation in the form of a laser beam 26. While only one laser 12 is shown in FIG. 1, additional lasers associated with additional flow channels, with each additional laser producing an additional laser beam, is within the scope of the present disclosure. For example, one or more embodiments of the present disclosure include a multichannel analytical instrument having two or more flow channels, two or more lasers associated with the two or more flow channels, and beam shaping optics associated with each flow channel. According to one or more embodiments of the present disclosure, the wavelength of the laser beam 26 is any wavelength that is appropriate for activating fluorescence in the light emission material bound to the nuclear DNA of the particle or cell of interest, such as sperm 16. For example, the wavelength may be between about 350 nm and 360 nm, or at about 355 nm in the case of sperm. However, in some embodiments, any wavelength within the range of 330 nm to 365 nm is within the scope of this disclosure.

According to one or more embodiments of the present disclosure any output power that does not damage or adversely affect the fertility of the sperm 16 may be employed. In some embodiments, the power of the laser beam 26 delivered to the sperm is as low as possible while maintaining a satisfactory sorting resolution between X- and Y-chromosome subpopulations. For example, some laser power ranges within the scope of the disclosure may include: 350 mW or less, 300 mW or less, 250 mW or less, 200 mW or less, 175 mW or less, 150 mW or less, 100 mW or less, 90 mW or less, 80 mW or less, 70 mW or less, 60 mW or less, 50 mW or less, 40 mW or less, 30 mW or less, 25 mW or less, 20 mW or less, or 10 mW or less. It may be appreciated that the lasers themselves may operate at even higher powers and that optics, such as filters, splitters, beam stops and the like, may be used to adjust the power actually delivered to sperm being sorted.

Still referring to FIG. 1, the laser beam 26 as output from the laser 12 may have a Gaussian beam profile. The Gaussian beam profile, as output from the laser 12, may be generally circular and may measure 0.9 mm in the horizontal direction and 1.1 mm in the vertical direction. Further, the Gaussian beam profile, often referred to as $TEM_{00}$ mode is generally most intense at a center point and uniformly less intense radially outward. Such circular beam spots are not suitable for sorting sperm without further modification, and even slightly elliptical beam spots suffer from similar problems. Namely, these beam spots expose sperm traveling down the center of the beam profile to a greater total laser power flux as compared to sperm on the periphery of the core stream and correspondingly closer to the edge of the beam. This great variation in total laser power experienced by the sperm passing within the inner core stream may result in decreased resolution between X- and Y-chromosome subpopulations and is generally undesirable for sperm sorting application.

Beam shaping optics may be used to manipulate the shape of a beam spot by, for example, manipulating the aspect ratio, or the vertical and horizontal aspects of the beam spot to address the issues of greatly varied laser power exposure experienced by the sperm and coincident excitation of fluorochrome bound to multiple DNAs. International Publication No. WO 01/85913 and U.S. Pat. No. 7,371,517, which are incorporated by reference herein in their entirety, describe embodiments that employ beam shaping optics to increase the area and reduce the height of a conventional irradiation beam pattern. Previous beam shaping optics sought to rectify this deficiency in sperm sorting with a highly stretched beam profile, such as a 160 μm beam width and 20 μm beam height. As is set forth in more detail below, these beam dimensions work well at low event rates (e.g. 20,000 events per second and less) in some configurations, but are very sensitive, become difficult to align, and generally lose quality very quickly as the event rate are increased or at increased beam paths, such as at the second flow channel in a multichannel system utilizing a shared laser. Accordingly, embodiments of the present disclosure modify the laser beam 26 as output from the laser 12 for interrogating sperm 16 in the fluid stream 8.

As shown in FIG. 1, the flow cytometer 100 or analytical instrument 110 may include beam shaping optics 20. In some embodiments, the beam shaping optics 20 may contain a pair of crossed cylindrical lenses. The lenses are positioned with respect to each other such that one of the lenses is a front lens and the other lens is a rear lens. The power of the lenses in combination with the distance separating the lenses may create differing elliptical beam patterns with respect to shaping the laser beam 26. According to some embodiments of this disclosure, the beam shaping optics 20 are configured to produce a beam pattern at the interrogation location 33 having certain characteristics relative to the inner core stream 17 of the fluid stream 8. According to some embodiments of this disclosure, the beam shaping optics 20 are configured to produce a beam pattern at the interrogation location 33 having specified absolute dimensions. According to some embodiments of this disclosure, the beam shaping optics 20 are configured to produce a beam pattern at the interrogation location 33 that performs at substantially the same level of resolution when the flow cytometer is operating at a variety of event rates, and at a variety of differing inner core stream sizes.

The beam shaping optics 20 may be located near fluid stream 8 for focusing the laser beam 26 at the interrogation location 33 on the fluid stream 8. A beam path 27 may comprise the path traversed by the laser beam between the laser 12 itself and the beam shaping optics 20. It may be appreciated that while FIG. 1 depicts a straight beam path, periscopes, mirrors, dichroic mirrors, filters and other optical elements may be employed for directing the laser beam 26 to the beam shaping optics 20. In some embodiments, the beam path 27 is as short as possible. For example, the beam path 27 may be between 2 inches and 18 inches in length, in other embodiments the beam path may be between 2 inches and 10 inches. Both the beam shaping optics 26 and the short beam path 27 individually provide improved sorting resolution and consistency for sperm sorting applications in a flow cytometer, and when combined may interact synergistically for even greater improvements.

According to one or more embodiments of the present disclosure, the beam shaping optics 20 may comprise a front lens and a rear lens with the rear lens positioned an appropriate distance away from a base point on the front lens. In some embodiments, the spacing between the rear lens and the base point on the front lens may be in a range of 50 mm to 60 mm. Further, in some embodiments the rear lens is a 100 mm focal point and the front lens is a 40 mm focal point and may have a power in a range of 18 µm/1 mm=0.018× for the 40 mm lens and 0.12 mm/1 mm=0.12× for the 100 mm lens. In this way, the beam shaping optics 20 may modify the width and/or the height of the laser beam 26 such that the resulting shaped beam 22 has the desired beam width and/or beam height at the interrogation location. Those of skill in the art can appreciate different lasers with differing initial beam shapes may require different lens strengths and distances to achieve a desired beam width. Such additional configurations are within the scope of this disclosure.

As previously mentioned, the beam shaping optics 20 may modify the width of the laser beam 26. In some embodiments, the modified width is greater than the Gaussian beam profile of the laser beam 26, but less than an elliptical beam profile having a width of 160 µm. In other embodiments, the beam shaping optics 20 shape the laser beam 26 to a width that is in a range of 110 µm or less, a width that is in a range of 70 µm to 110 µm, a width that is in a range of 70 µm to 90 µm, or a width that is in a range of 90 µm to 110 µm, or a width that is in the range of 110 µm to 130 µm.

Further, in some embodiments, the beam shaping optics 20 may modify the laser beam 26 relative to a dimension of the core stream of the fluid stream 8. For example, the flow cytometer 100 or analytical instrument 110 according to embodiments of the present disclosure may be configured such that the differential pressure between the core stream and the sheath fluid of the fluid stream 8 may be adjusted to change the processing speed of the flow cytometer 100. The differential pressure between the core stream and the sheath fluid of the fluid stream 8 is directly related to the processing speed of the flow cytometer 100 in terms of the number of events that are detected each second. As such, increasing the differential pressure between the core stream and the sheath fluid of the fluid stream 8 increases the processing speed of the flow cytometer 100. Moreover, this increase in differential pressure also increases the size of the core stream, such as the inner core stream width. That is, the size of the core stream increases as the processing speed of the flow cytometer 100 increases. For example, the size of the core stream at an event rate between 40,000 to 90,000 events per second is dramatically larger than the size of the core stream at an event rate between 10,000 to 20,000 events per second.

The inventor has discovered that the conventionally accepted beam width utilized in commercial applications of sperm sorting, namely a beam width of 160 µm, causes a great deal of the total laser energy flux to be wasted at the outer wings of the elliptically stretched Gaussian distribution of the beam. Due to this wasted energy, sperm on the outer boundaries of the inner core stream cannot be uniformly illuminated at these higher event rates as they are exposed to less overall laser energy while traversing the laser beam as compared to sperm in the middle of the laser beam. This increased variation in laser power experienced by the sperm in different positions reduces sorting resolution. Further, at higher event rates where the core stream becomes larger, these losses often become compounded. Such a loss in resolution results in a productivity loss, a purity loss, or both, depending on how regions and other sorting parameters are adjusted.

As used in many examples throughout this disclosure, event rates often serve as a proxy for the volumetric flow rate of sample through the flow channel, particularly as the event rate is synonymous with changes in core stream dimensions. In several figures and examples, the concentration of sperm nuclei was 200 million per ml, the nozzle which formed the coaxial stream had included an orienting nozzle tip having an orifice of 70 µm in diameter, and the sample pressure was set to a value of about 40 PSI. Those of skill in the art can appreciate that changing the concentration of sperm in the sample can vary the event rate without impacting the dimensions of the core stream, while changes to the orifice diameter and sample pressure may affect both the event rate and the volumetric throughput of sample (and correspondingly the dimensions of the core stream).

Returning to FIG. 1, sperm 16 will reflect or emit electromagnetic radiation 23 when excited with a laser 12 of an appropriate wavelength. In the case of sperm stained with a fluorochrome, sperm will fluoresce. As is known to those in the field, the flat paddle shape surface of sperm head emits fluorescence in proportion to the amount of nuclear DNA it contains. Additionally, the thin sides of the paddle shaped sperm head emit a very bright fluorescence, which is used to determine whether or not the sperm being excited is properly oriented.

A particle or cell characteristics are determined with a particle or cell sensing system 10, which forms a portion of the flow cytometer 100. In the case of sperm cell characteristics can include: orientation, viability, and a sex differentiation characteristics, such as the presence of any X- or Y-chromosome. FIG. 1, illustrates one such particle or cell sensing system 10 as a portion of the flow cytometer 100. The depicted particle or cell sensing system 10 includes at least one detector 11 that responds to the particles or cells contained within the fluid stream 8. For example, stained sperm may be excited by a laser 12 at an interrogation location 33, which causes the stain to emit or reflect electromagnetic radiation 23. The at least one detector 11 detects the fluorescence in response to the interrogation of the particles, cells, sperm, or the like and generates at least one signal based on the detected response. An analyzer 13 receives at least one signal from the at least one detector 11 to analyze any number of conditions, which are further described below, in accordance with embodiments of the present disclosure. The analyzer 13 may be a general purpose computer, processor, or the like with software for performing specific functions for the sorting or sperm, or may be a purpose build computer or processor incorporated with the flow cytometer.

Still referring to FIG. 1, in embodiments where the analytical instrument is a droplet generating flow cytometer, the analyzer 13 may be coupled to a droplet charger, such as a charge pin 34 that differentially charges sheath fluid 18 within the nozzle and fluid stream 8 up to and including newly forming droplets. In this manner, each droplet 9 may be charged based particle or cell characteristics determined in the analyzer 13. For example, droplets may be charged based on a detected sex differentiation characteristic of stained sperm 16 entrained within the droplet 9. In these embodiments a skewing element 14 facilitates sorting the differentially charged droplets into one or more subpopulations, such as viable X-chromosome bearing sperm and/or viable Y-chromosome bearing sperm. As an example, the skewing element 14 may include a pair of electrostatic deflection plates in a droplet generating flow cytometer that provide differentially charged droplets 9 with differing trajectories, such as into one or more collection containers 15, thereby separating the droplets 9 into enriched subpopulations of X- and Y-chromosome bearing sperm. In this way, the skewing element 14 generates a population of sperm having a skewed sex ratio of viable sperm.

In other embodiments, the analyzer 13 may be connected to a skewing element that includes an ablation laser for damaging or photo-ablating sperm selected based on their classification. Specifically, the ablation laser may be timed to kill, damage, or deactivate sperm 16 in the fluid stream 8 based upon a certain classification or characteristic. For example, if it is desired to generate a population of sperm having a skewed ratio of viable X-chromosome bearing sperm, then the ablation laser may be used to damage or kill Y-chromosome bearing sperm in the fluid stream 8. On the other hand, if it is desired to generate a population of sperm having a skewed ratio of viable Y-chromosome bearing sperm, then the ablation laser may be used to damage or kill X-chromosome bearing sperm in the fluid stream 8. In this way, laser ablation may be used as a technique to isolate, separate, select, classify or sort particles, cells, sperm or the like based upon particle or cell characteristics in accordance with one or more embodiments of the present disclosure.

The analytical instrument according to one or more embodiments of the present disclosure may not include a skewing element. In these embodiments, the analyzer 13 of the analytical instrument may be used to check sorted purity, to check for any number of stains or stain conditions, or to analyze any number of conditions or criteria with respect to a given sample of pre-stained sperm.

Further, as mentioned above, the analytical instrument according to one or more embodiments of the present disclosure may be a microfluidic chip. In these embodiments, the flow channel of the microfluidic chip may include at least one channel having cross-section dimensions in the range between about 1.0 µm and about 2000 µm. Further, the microfluidic chip may include a system of flow cytometer capillaries and a diverting mechanism to serve as a skewing element for generating a population of sperm having a skewed sex ratio of viable sperm. Further, U.S. Pat. Nos. 7,311,476; 9,057,676 and International Application No. PCT/US2013/031706 which are incorporated by reference herein in their entirety, describe embodiments of a microfluidic chip that may be used in accordance with one or more embodiments of the present disclosure.

While FIG. 1 only illustrates a single flow channel 2, the analytical instrument according to one or more embodiments of the present disclosure may comprise a multichannel analytical instrument that includes a plurality of additional flow channels. In such a multichannel analytical instrument, each additional flow channel may create an additional coaxial flow of a fluid stream having an additional inner core stream of the sample fluid and an additional outer stream of the sheath fluid. The additional flow channels may be accompanied by a duplication of the elements depicted in FIG. 1 and FIG. 2, or the additional flow channels may share components with the flow channel. As but one example of flow channels sharing resources, the flow channel and the additional flow channel may be supplied sheath fluid from a single sheath fluid source.

Turning now to FIG. 2, an enlarged three dimensional view of the interaction between the fluid stream 8 and the laser beam 26 is depicted at the interrogation location 33 alongside an indication of an X, Y and Z axis. Various components of a flow cytometer 100, including a flow channel 2, an orifice 5 of a nozzle included in the flow channel 2, a fluid stream 8, and a laser 12, which have been previously described with respect to FIG. 1. As non-limiting examples, International Publication No. WO 01/85913 and U.S. Pat. No. 7,371,517, which have been incorporated by reference herein in their entirety, describe embodiments of a flow cytometer that may be used in accordance with one or more embodiments of the present disclosure. Flow cytometer platforms from other manufactures may likewise benefit from and be used in accordance with one or more embodiments of the present disclosure.

As shown in FIG. 2, the fluid stream 8 includes an inner core stream 17, which contains the sperm 16, and an outer stream 18 of sheath fluid surrounding the inner core stream 17. The laser beam 26 is depicted traveling along the X axis to the interrogation location where the laser beam 26 interacts with sperm 16 within the inner core stream 17 being flowed along the Z axis. Sperm 16 in the fluid stream 8 are excited by the laser beam 26 as described above. As a consequence, properly oriented sperm will produce electromagnetic radiation in the form of forward fluorescence 23*a* from the flat paddle-like surface of the sperm head along the X axis. Oriented sperm additionally produce electromagnetic radiation from their narrow sides known as side fluorescence 23*b* along the Y axis.

A first detector 11*a*, such as a forward fluorescence detector, is placed in the forward position along the X axis to collector forward fluorescence 23*a*. Those of skill in the art can appreciate additional optics, such as a collection lens or objective, may focus forward fluorescence onto the first detector 11*a*. A second detector 11*b* is, known as a side fluorescence detector, is placed at a position 90 degrees relative to the first detector 11*a*, such as along the Y axis.

FIG. 3 illustrates a cross section of the fluid stream 8 at the interrogation location 33. Again, the fluid stream comprises an outer stream 18 of sheath 3 and an inner core stream 17 of sample fluid 19. The inner core stream 17 can be seen having a generally elliptical shape within the fluid stream 8. Suitable orienting nozzles, such as those described in International Patent Publications WO2001/40765, WO2001/085913, and WO 204/088283, or other suitable orienting nozzles produce generally elliptical or ribbon flows of sample fluid 19. However, embodiments of the present invention are not limited to a specific inner core stream geometry. Other geometries suitable for orienting sperm will similarly benefit from aspects of this disclosure. As depicted, the inner core stream 17 has a major axis which aligns with the Y axis. The major axis corresponds to the inner core stream width 30. The inner core stream 17 also has a minor axis along the X axis which corresponds to the inner core stream depth 31.

FIG. 4 depicts a cross sectional view of the laser beam 26 at the interrogation location 33 referencing the same coordinates system depicted in FIGS. 2 and 3. The depicted beam originates from a laser operating in a $TEM_{00}$ mode, or having a Gaussian beam profile, which has been stretched in one aspect and compressed in another aspect. It may be appreciated that beam dimensions (such as beam height and beam width) referenced throughout this disclosure relate to the distance between the diametrically opposed points on either side of a central beam peak power at which the beam power is $1/e^2$ (0.135) of the beam peak power, or 13.5% of the peak power of the Gaussian beam profile.

As depicted, the laser beam 26 has a beam width 36 along the Y axis and a beam height 37 along the Z axis. The geometry of the beam width 36 and the beam height 37 may be referred to throughout as a laser beam pattern. Once the laser beam 26 is shaped by the beam shaping optics 20, that portion of the laser beam 26 may be referred to as a modified laser beam. Additionally, the laser beam 26 has a center portion 38 at the interrogation location 33. The center portion 38 may comprise between an innermost half of the beam width and an innermost quarter of the beam width 36. In some embodiments the center portion 38 may comprise about an innermost third of the beam width.

Small variations in total laser energy experienced by stained sperm produce variations in the amount of fluorescence produced. Given the industry standard for sorted sperm purities is at least 85%, even a small variation may begin to obstruct the 3.8% nuclear DNA difference between X- and Y-chromosome bearing sperm, especially at high event rates such as 40,000 to 90,000 events per second (or even higher). Applicants surprisingly found that matching the center portion 38 of the beam width 36 to the inner core stream width provided unexpected improvements in resolution. Further, the inventor found certain absolute dimensions provided stable sorting at a variety of event rates. Beam shaping optics used in the prior art provided good resolution, but that resolution fell apart quickly if and when the inner core stream width was modified, such as to increase event rates and/or sorting speeds.

Such a modified beam profile is particularly useful at higher event rates, such as between 40,000 and 90,000 events per second. Indeed, the resulting sorting resolution between X- and Y-chromosome bearing sperm may be dramatically reduced if the inner core stream width 31 is wider than the center portion 38 of the beam width, as sperm traversing the beam spot on the outer edges of the inner core stream width 30. However, prior art beam shaping optics have also been too wide. For example, a beam width of 160 microns has a large center portion with a relatively even distribution of energy flux, but too much power is wasted outside the region of interest, (i.e. the inner core stream 17) and sorting resolution deteriorates at higher event rates.

Figure 5:
FIG. 5 shows a graphical representation of a measured first end point, middle point and a second end point in determining inner core stream widths at a number of event rates.
Figure 6:
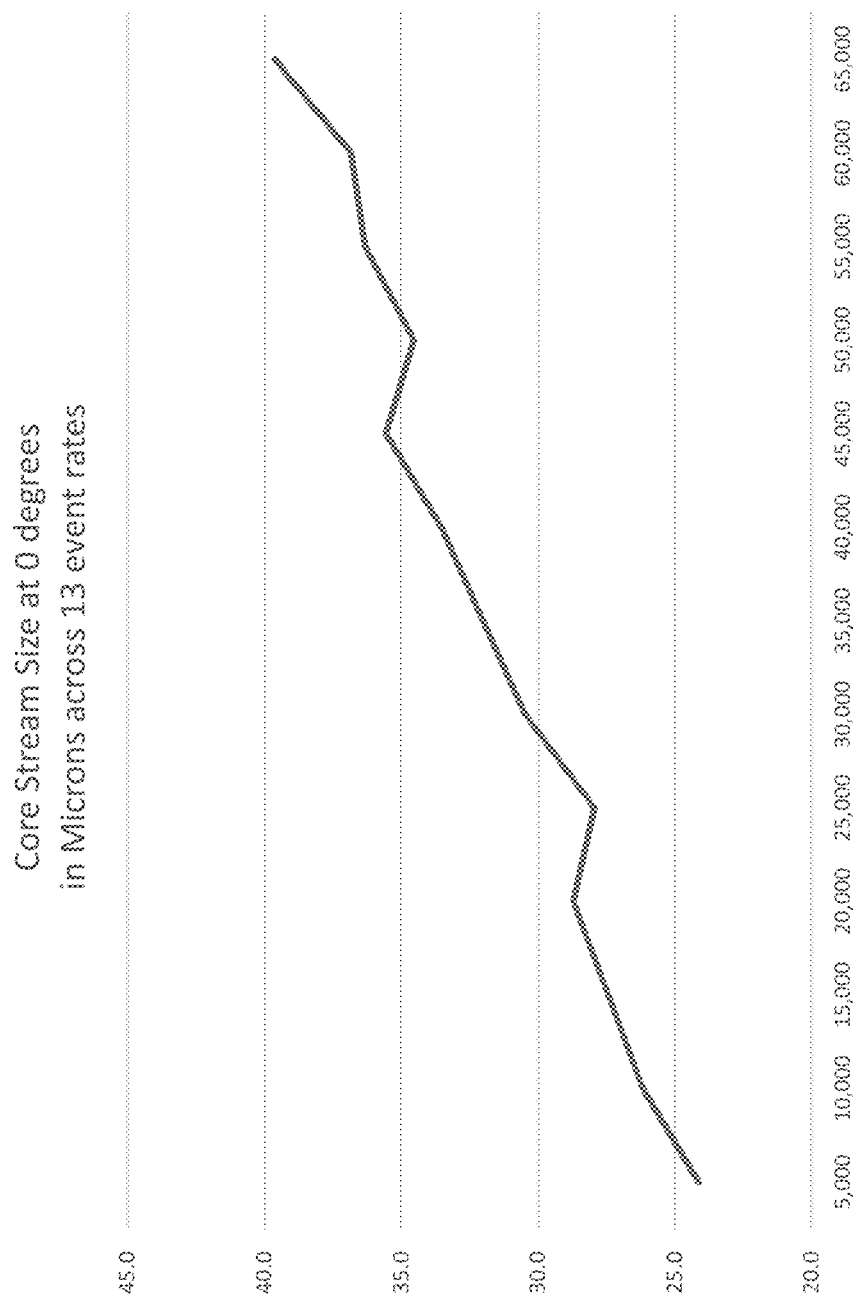
FIG. 6 shows a graphical representation of measured inner core stream widths at a number of event rates.

Referring now to FIGS. 5 and 6, Applicant was able to measure the effective inner core stream width in a sperm sorting flow cytometer by measuring the distance from center stained nuclei traveled during sorting any/or analysis in such a flow cytometer. Applicant generated fluid streams with an orienting nozzle tip having a 70 μm orifice at varying event rates by mounting a micrometer to the laser beam stage. A fluid stream having an inner core stream with stained sperm nuclei was generated in a flow cytometer through an orienting nozzle tip. An oscilloscope with a high gain was fed a signal from a PMT arranged to detect fluorescence from the inner core stream. First the center of the core stream was located by determining the laser position resulting in the highest signal, and the center location was noted as the "Middle of Core" and associated with the current reading on the micrometer. As can be seen in FIG. 5, the "Middle of Core" was consistently found to be at about 33.5 μm on the micrometer. The laser was then swept until a front edge of the core stream was found. The front edge of the core stream was verified both visually by viewing the position on the micrometer at which there was no longer a glow under a microscope and at which the oscilloscope no longer registered pulses and the distance on the micrometer was noted as the "Front of Core." The laser was then reset to the center of the core stream, and the back edge was found in with a similar sweep in the opposite direction and noted as the "Back of Core." The same methodology was performed at event rates from 5,000 events per second to 65,000 events per second, as can be seen in FIGS. 5 and 6. Specifically, the relative front, back and middle positions as indicated by the micrometer are shown in FIG. 5. FIG. 6 illustrates the difference between the position of the front and back edges, or the width of the core stream. As can be seen in FIG. 6, between 5,000 and 65,000 events per second, at a concentration of 200 million cells per second, there appears to be a linear increase in the inner core stream width from about 24 μm to 40 μm.

According to one or more embodiments of the present disclosure, beam shaping optics may "substantially" match the center portion of the beam width to an inner core stream width 30, such an inner core stream width facing the laser. As used throughout this disclosure, substantially matching the center portion of the beam width to an inner core stream width may be expressed in relative terms, or by specific measurements. For example, matching the center portion of the beam width to an inner core stream width can comprise matching the inner core stream width 30 to the inner most half of the beam width, matching the inner core stream width 30 to the inner most third of the beam width, matching the inner core stream width 30 to the inner most quarter of the beam width, or matching the inner core stream width 30 to between the inner most quarter and a half of the beam width. As but a few examples of a substantially matched laser beam widths and inner core streams, at high event rates of at least 40,000 events per second, the beam shaping optics may provide a beam width in a range of 90 μm to 130 μm at the interrogation location 33. According to additional embodiments of the present disclosure, substantially matched laser beam widths and inner core streams at lower event rates of 10,000 to 25,000 events per second, include beam shaping optics that provide a beam width in a range of 70 μm to 130 μm. In other embodiments, the beam shaping optics 20 shape the laser beam 26 to have a beam width that is in a range of about 70 μm to about 90 μm, about 90 μm to about 110 μm, or about 110 μm to about 130 μm. In some embodiments, a width of the laser beam that "substantially" matches the inner core stream width 30 facing the laser means a laser beam width that is within a range of about 2 to 4 times the inner core stream width 30 facing the laser. In other embodiments, a width of the laser beam that "substantially" matches the inner core stream width 30 facing the laser means a laser beam width that is within a range of about 1.5 to 4.5 times the inner core stream width 30 facing the laser. By substantially matching a width of the laser beam 26 with the inner core stream width 30 facing the laser, less energy is wasted, and the dramatic fall off within the edges of the wider core stream can be reduced. Moreover, the beam shaping optics 20 according to embodiments of the present disclosure allow the ability for the flow cytometer 100 or analytical instrument 110 to shift from small core streams (i.e., lower event rates) to large core streams (i.e., higher event rates) with a minimal loss in resolution on a single machine utilizing a single beam shaping optics set-up.

According to one or more embodiments, the beam shaping optics 20 may also adjust the beam height of the laser beam 26. For example, beam shaping optics 20 reduce the beam height of the laser beam 26 to a height that is less than the 35 μm Gaussian beam profile. In some embodiments, the Gaussian beam profile of the laser beam 26 is reduced to a height that is less than 20 μm. In some embodiments the Gaussian beam profile of the laser beam 26 is reduced to a height in a range of 18 μm to 20 μm. In still other embodiments, the Gaussian beam profile of the laser beam 26 is reduced to a height that is 18.5 μm.

By using the beam shaping optics 20 to reduce the beam height of the laser beam 26, the coincidence of multiple sperm heads being within the shaped laser beam 26 during the same measured event is greatly reduced. Stated another way, the laser excitation of bound light emission material in multiple sperm heads that are within the laser beam 26 at the same time is reduced. This results in improved precision of the flow cytometer 100 or analytical instrument according to one or more embodiments of the present disclosure as a mean difference between light emissive events that distinguish between X-chromosome bearing sperm and Y-chromosome bearing sperm, or that correspond to different stains or stain conditions, is increased.

According to one or more embodiments of the present disclosure, the beam shaping optics 20 may produce a laser beam at the interrogation location having a beam width to beam height ratio that is between about 7:1 and about 3:1; between about 6:1 and about 4:1; between about 7:1 and about 6:1; between about 6:1 and about 5:1; between about 5:1 and about 4:1; or between about 4:1 and about 3:1.

According to one or more embodiments of the present disclosure, the beam shaping optics 20 may produce a laser beam at the interrogation location that performs substantially the same with fluid core stream having inner core widths between 24 μm and 40 μm. In another embodiment, the beam shaping optics 20 may produce a laser beam at the interrogation location that performs substantially the same at event rates between 5,000 events per second and 65,000 events per second. In the context or performance on the same fluid stream at different core stream widths, the phrase "substantially similar performance" may be understood as determined by measuring a PVR of nuclei across said core stream widths within 15% of each other, within 14% of each other, within 13% of each other, within 12% of each other, within 11% of each other, within 11% of each other, within 10% of each other, within 9% of each other, within 8% of each other, within 7% of each other, within 6% of each other, within 5% of each other, within 4% of each other, within 3% of each other, within 2% of each other, or even within 1% of each other, while all PVRs for a well aligned machine remain above 85%.

According to one or more embodiments of the present disclosure, the beam shaping optics 20 may shape the laser beam 26 to provide excellent uniformity by concentrating more energy within the inner core stream 17, which increases the uniformity of energy flux received by sperm at all locations within the inner core stream 17. Further, the modified beam profile, according to embodiments of the present disclosure, provides the versatility of being able to shift between low and high event rates on a single machine without adversely affecting the sorting resolution of the sample. The beam shaping optics 20 further advantageously allows comparable sorting resolution results to be achieved, with a lower powered laser than the lasers currently used in flow cytometry applications. Relatedly, such improvements in resolution may allow for shortened staining times and reduced amounts of stain, both of which can be detrimental to the viability of a sorted sperm in artificial insemination.

In particular, prior sperm sorting flow cytometers utilized a single laser which was split two ways, or even three ways, diverting some portion of the beam power to multiple flow channels. Such configurations often required at least a beam path of 25 inches to the closest flow channel, 50 inches to a second flow channel, and as much as 65 inches to the third flow channel. While filters and splitters are designed to provide each flow channel with an equivalent beam, in reality the longest beam path is the most sensitive and the most difficult to align. Furthermore, resolution and sorting speeds are typically worse on the flow channel having the longest beam path.

Accordingly, certain embodiments of the present disclosure seek to reduce as far as possible the beam path 27 and provide similar, or the same, laser 12 and beam shaping optics 20 with each fluid stream 18 in a multichannel instrument. In this way, it can be assured that each fluid stream in a multichannel instrument is exposed to a uniform power and beam profile. In contrast to prior multichannel systems, substantially identical performance can be achieved in each channel. Some embodiments may incorporate a small footprint continuous wave laser, such as the Coherent Genesis CW-355. Such a small laser can be set on a stage and aligned directly with the interrogation location. In some embodiments, optical elements such as prisms, mirrors, dichroic filters and the like may be incorporated to direct the laser beam 26 to the interrogation location 33 with a minimal beam path. Other embodiments may incorporate a pulsed laser, such as a Vanguard 350-355 (Spectra Physics). The Vanguard 350-355 has a significantly larger footprint, including a total length of nearly 3 feet. As such, embodiments of the present disclosure include the construction of a platform in direct alignment with the beam shaping optics for directly illuminating the flow channel at the interrogation location. In other embodiments, the platform may be on another plane and may incorporate optics, such as a periscope, mirrors, prisms and the like to direct the laser beam to the beam shaping optics for illuminating the flow channel at the interrogation location. Regardless of the lasers implemented, the shortened beam path 27 in combination with providing a laser for each flow channel having minimal, but identical or equivalent optics, provides great improvements in the overall performance of a multichannel sperm sorter, such as a Genesis II or a Genesis III. Other multichannel instruments incorporating multiple nozzles on a single platform may similarly be improved.

Referring back to FIG. 1, a beam path 27 is illustrated. As previously described, the beam path may be between 2 and 18 inches in some embodiments. In other embodiments, the beam path may be as short as is possible or as short as is practical. Both the beam shaping optics described in certain embodiments of this disclosure and a shortened beam path provide significant improvements in the sperm sorting process individually, and perhaps also provide a synergy when used in conjunction. By way of an example, beam shaping optics currently used in sperm sorting have a beam width of 160 microns. As will be demonstrated, such a beam width is suboptimal in the application of sperm sorting. However, the smaller beam widths may be more difficult to align, and these difficulties can be compounded when longer beam paths are utilized.

According to one or more embodiments of the present disclosure, the beam path 27 may be less than about 18 inches in length, less than about 17 inches in length, less than about 16 inches in length, less than about 15 inches in length, less than about 14 inches in length, less than about 13 inches in length, less than about 12 inches in length, less than about 11 inches in length, less than about 10 inches in length, less than about 9 inches in length, less than about 8 inches in length, less than about 7 inches in length, less than about 6 inches in length, less than about 5 inches in length, less than about 4 inches in length, less than about 3 inches in length, or less than about 2 inches in length.

Further embodiments including a short beam path, include a multichannel system with multiple lasers and multiple short beam. Referring back to FIG. 3, the front view of beam shaping optics 20 according to an embodiment of the present disclosure is shown. A beam path 27 is shown along which the laser beam 26 traverses between the laser 12 and the beam shaping optics 20. While only one beam path is shown in FIG. 3 additional beam paths between additional lasers and associated additional beam shaping optics are within the scope of embodiments of the present disclosure. For example, there may be two or more beam paths between two or more lasers and associated two or more beam shaping optics within the scope of the present disclosure. In such embodiments, the additional beam paths may not overlap or intersect from each laser to each associated flow channel.

Further, in embodiments where a multichannel analytical instrument includes more than one beam path, each beam path may be the same length. In embodiments of flow cytometers having two flow channels, two lasers associated with the two flow channels, and a beam path from each laser to the associated flow channel, the combined beam path length for the two lasers is less than 36 inches, or each beam path may be less than 18 inches. In embodiments where a multichannel analytical instrument includes three flow channels, three lasers associated with the three flow channels, and a beam path from each laser to the associated flow channel, the combined beam path length for the three lasers is less than 54 inches, or each beam path may be less than 18 inches.

Existing multichannel sperm sorting flow cytometer systems include a single laser that is split with a beam splitter, propagating two or three beams, less an insignificant amount of losses from absorption of the splitting component, towards two or three flow channels. This arrangement requires anywhere from 25 to 50 inches of beam path between the laser output and the beam shaping optics, which focus the beam on the particles (e.g., sperm) in the core stream. In fact, other commercial sperm sorting flow cytometer systems incorporate a laser that is split three ways, and the longest beam path on those commercial flow cytometer systems requires up to 65 inches between the laser and the beam shaping optics. As can be appreciated, stability issues created at 25 to 50 inches are much more pronounced at 65 inches. Such issues with instability may be compounded by the fact that the beam slightly expands as it travels. The beam entering beam shaping optics from a 25 inch beam path will vary from the beam on the 65 inch beam path. Further, the UV wavelength used to sex sort sperm is susceptible to thermal drift, meaning air currents, such as from air conditioning vents or technician movement around the instrument, can affect beam stability. Additionally, vibrations or other minor physical contact with the flow cytometer can upset the rather sensitive alignment of a narrow beam profile, especially with the longer beam paths. In addition to the beam path length itself, longer beam paths require steering mirrors or other optical elements, which introduce additional opportunities for instability and require calibration when lasers are replaced.

Indeed, such long beam path lengths may contribute to poor beam stability in commercial flow cytometers. By shortening the length of the beam path in accordance with one or more embodiments of the present disclosure, a much more stable flow cytometer or analytical instrument may be achieved. Accordingly, one or more embodiments of the present disclosure include multiple beam paths each of which has a beam path length: less than about 18 inches in length, less than about 17 inches in length, less than about 16 inches in length, less than about 15 inches in length, less than about 14 inches in length, less than about 13 inches in length, less than about 12 inches in length, less than about 11 inches in length, less than about 10 inches in length, less than about 9 inches in length, less than about 8 inches in length, less than about 7 inches in length, less than about 6 inches in length, less than about 5 inches in length, less than about 4 inches in length, less than about 3 inches in length, or less than about 2 inches in length.

As described above, a continuous wave laser may be used as the laser in the flow cytometer or analytical instrument according to one or more embodiments of the present disclosure. Generally, those of ordinary skill in the art have thought continuous wave lasers to have particular disadvantages in flow cytometry applications. With respect to sperm, it is understood that irradiation may result in lower fertility of the sperm. As understood, traditional continuous wave lasers were large, power-hungry, water cooled, high failure, low lifetime, required daily alignment, and provided a broadband wavelength of 333 nm to 363 nm. These factors contributed to a paradigm shift to move away from the use of traditional continuous wave lasers to pulsed lasers, which were cost-effective, smaller in size, economical, air cooled, had an internally fixed alignment cavity and provided a single wavelength system. The high peak power of the pulsed laser allowed a shift to the use of a single laser to supply split laser beams to multichannel instruments. Further, the single wavelength pulsed lasers were very efficient at saturating the DNA binding dyes with very high peak powers. However, the inventor has discovered beam shaping optics, which may reduce the power requirement for sorting sperm.

This disclosure contemplates a multichannel sperm sorting system with any number of lasers individually associated with flow channels. As one example, a Genesis III sperm sorting system (Cytonome/ST, Boston Mass.) can be modified to include three lasers for each of three flow channels. In one embodiment, small footprint lasers can be placed with a beam path between 2 and 10 inches to the respective beam shaping optics. In another embodiment, the Genesis III can be modified to include a single platform, or three individual platforms for holding three larger footprint lasers in a position that provides a short beam path with each flow channel. The larger footprint lasers may require a periscope, or other optics to deliver the beam to the beam shaping optics. As such, the beam paths for larger footprint lasers may be between 6 inches and 12 inches.

Other embodiments contemplate a Genesis II could be modified in a similar manner so that two lasers can be directed to two flow channels in those multichannel systems. Regardless of the number of lasers and corresponding number beam paths, this disclosure provides improved beam shape matching and reduced beam paths that vastly improve sorting resolution at each flow channel and that additional provide a for substantially similar performance at each channel. In contrast, with previous split laser configurations, it is not possible to decrease the beam profile from conventional sperm sorting beam profiles, as any instabilities created from the long path lengths are amplified causing even greater instability and decreases in sorting performance. As such, conventional beam shaping optics with or without incorporating a beam splitter cannot perform well enough to use such lower laser powers and fall short of the improved signal quality realized by the short laser beam path and modified beam shaping optics.

Further, this disclosure contemplates that individual pulsed lasers may be associated with individual channels in a multichannel system. Such a system may benefit independently from the shortened beam path described herein and from the modified beam shaping optics as set forth herein. Such systems may also benefit synergistically from the combination of the shortened beam path and the modified beam shaping optics described herein. In particular, such an instrument may provide substantially the same performance at each channel of a flow cytometer, demonstrating a drastic improvement over the current systems that split a single laser over multiple flow channels and include beams paths as long as 65 inches. Furthermore, the beam shaping optics and the shortened beam path, which will be shown below to provide flexibility in beam power and event rate, benefit each channel equally, without additional loses or alignment issues from beam splitting optics.

According to one or more embodiments of the present disclosure, a method of generating a population of sperm having a skewed sex ratio of viable sperm may be performed using any of the analytical instruments or multichannel analytical instruments described herein.

For example, in one or more embodiments, the method may include creating a coaxial flow of a fluid stream that includes an inner core stream of a sample fluid having differing orthogonal dimensions transverse to the coaxial flow and an outer stream of a sheath fluid, modifying a laser beam to have a beam height and a beam width, substantially matching an inner core stream width facing the laser to a center portion of the beam width, interrogating the sperm in the core stream with the laser beam pattern, detecting a response to the interrogation of the sperm, generating at least one signal based on the detected response, and classifying a sex differentiation characteristic of the sperm based on the at least one signal.

In embodiments using a multichannel analytical instrument, the aforementioned method may employ, for example, first and second coaxial flows of a fluid stream, first and second inner core streams, first and second outer streams, first and second laser beams generated along first and second laser beam paths that do not overlap. In such embodiments, the method includes modifying the first laser beam and the second laser beam to each have a beam height and beam width, interrogating the sperm in the first inner core stream with the first modified beam and interrogating the sperm in the second inner core stream with the second modified laser beam, detecting a response to the interrogation of the sperm with the first modified beam and detecting a response to the interrogation of the sperm with the second modified laser beam, generating at least one first signal based on the detected response to the interrogation of the sperm with the first modified laser and generating at least one second signal based on the detected response to the interrogation of the sperm with the second modified laser beam, and classifying a sex differentiation characteristic of the sperm in the first inner core stream based on the at least one first signal and classifying a sex differentiation characteristic of the sperm in the second inner core stream based on the at least one second signal. In such methods the use of individual lasers and short beam paths that do not overlap can provide each fluid stream in a multichannel instrument with substantially identical performance. As used throughout, "substantially identical performance" means the shape and intensity of the modified laser beam is nearly identical at the interrogation location of each fluid stream when such fluid streams are interrogated with the same laser at the same power as a result of identical or equivalent beam shaping optics on each beam path in a multichannel instrument and that each beam performs similarly in terms of stability. In contrast, previous instruments utilized a single laser that was split and directed to each channel. Such optics include dichroic mirrors designed to reflect a portion of the beam energy and to transmit a portion of the beam energy. While such mirrors are selected and configured to theoretically supply each channel with identical beam profiles, it has been found that an increasing degree of divergence occurs in the beam traveling along the longest beam path. It has also been found that the beam traveling along the longest path is the least stable. Movement or vibrations, and even air currents from air conditioning vents, have a much greater impact on the beam traveling through the longest beam path. Substantially identical performance, with respect to multiple channels in an analytical system, may be empirically determined based on the sorting performance at each sorting head, assuming each sorting head is aligned and running comparable sample, by comparing ease of alignment, stability, PVR, or some combination thereof at each channel.

Figure 7:
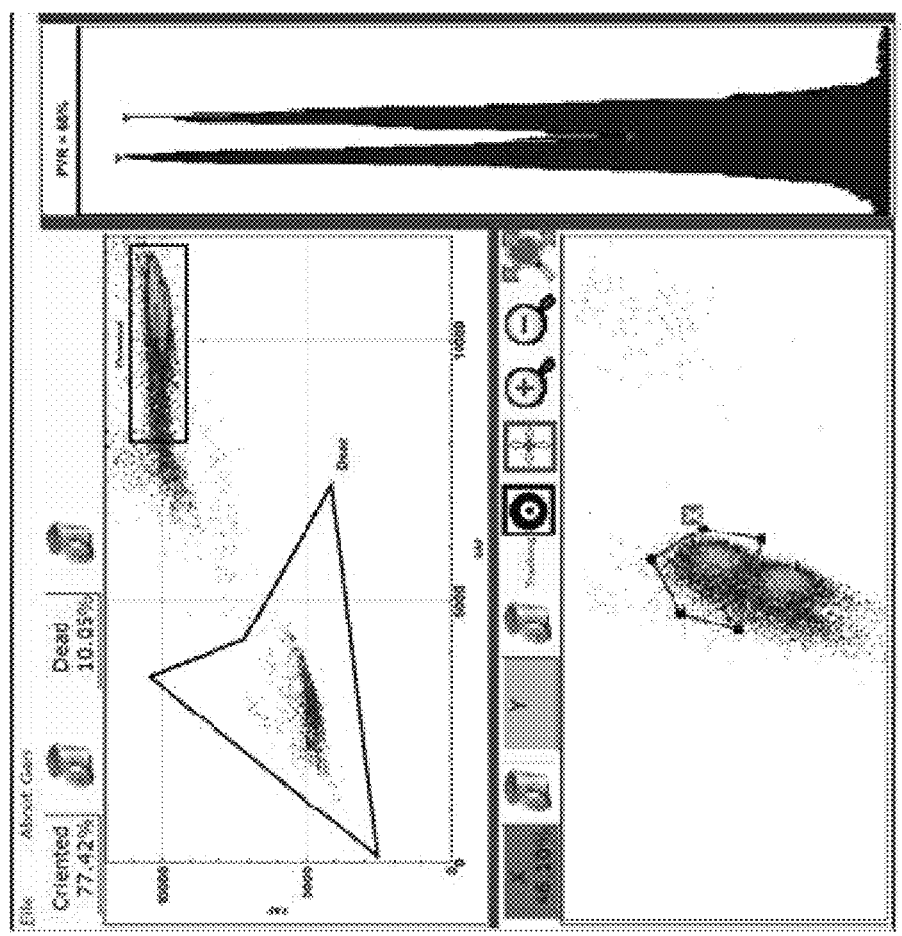
FIG. 7 shows examples of bivariate plots and a corresponding histogram of a resulting sorting resolution as visualized on a flow cytometer monitor.

FIG. 7 illustrates a generic example of bivariate plots and corresponding histograms produced during the operation of a sperm sorting flow cytometer and specifically illustrates the sorting resolution as visualized on a flow cytometer monitor during sorting. As previously mentioned, according to one or more embodiments, the analyzer 13 analyzes the forward fluorescence of the DNA selective light emission material as detected by the first detector 11a, and the side fluorescence of the DNA selective light emission material as detected by the second detector 11b. Accordingly, the top bivariate plot of FIG. 7 illustrates events as a function of peak forward fluorescence and peak side fluorescence. From this plot, the oriented sperm as well as the dead sperm are easily identifiable. Indeed, regions can be drawn around these populations of sperm and their numbers can be tracked as absolute numbers or as percentages. FIG. 7 illustrates two such regions drawn on the bivariate plot showing 77.42% of the sperm were properly oriented and 10.05% of the sperm were dead, based on the cells inside those regions. Only sperm within the oriented region are plotted in the second bivariate plot (peak vs. integrated area) at the bottom of the screen. In the second plot, the upper subpopulation of oriented sperm includes X-chromosome bearing sperm, and the lower subpopulation of oriented sperm includes Y-chromosome bearing sperm. From this second plot, a sort region may be drawn by an operator around the subpopulation of interest. As shown in FIG. 7, for example, the sort region "X" includes sperm that have been sorted as X-chromosome bearing sperm. According to one or more embodiments of the present disclosure, the flow cytometer or analytical instrument having a skewing element may sort the events falling in the specified sort region into a collection tube.

Still referring to FIG. 7, the flow cytometer or analytical instrument according to one or more embodiments of the present disclosure may include a population tracking software package that tracks the center of mass of certain populations of data. For example, as the two very close subpopulations in the bottom bivariate plot of FIG. 7 drift over time, population tracking software would attempt to keep the "X" sort region over the top population of cells. Non-limiting examples of suitable software tracking packages include the CyTrack™ software on Beckman Coulter's MoFlo™ flow cytometers or in the tracking software of Cytonome/ST's Genesis™ flow cytometers, as well as software described in International Application Number PCT/US2004/009646. Software may also be incorporated that generates sort regions based on user input, such as a desired purity. FIG. 7 represents an image generated from a Cytonome/ST Genesis™ flow cytometer. It can be seen that the number of events in the peaks, more specifically the average of two peaks, and the number of event in the valley are determined and an ongoing PVR is displayed during the operation of sorting. This PVR represents the amount of overlap between the presumptive X- and Y-chromosome bearing subpopulations. As such, PVR is discussed throughout this disclosure in the context of a measure of resolution.

Still referring to FIG. 7, the right side of the flow cytometer monitor shows a corresponding histogram of a resulting sorting resolution between X- and Y-chromosome bearing sperm subpopulations. Again, only sperm falling into the region labeled as oriented is displayed in the histogram. Specifically, the histogram illustrating two peaks show how well the subpopulations were resolved. In this example, the PVR is 66%. For reference a PVR of 100%, would indicate the white valley separating the X and Y subpopulations reaches the baseline and would represent a perfect resolution.

EXAMPLE 1

Figure 8:
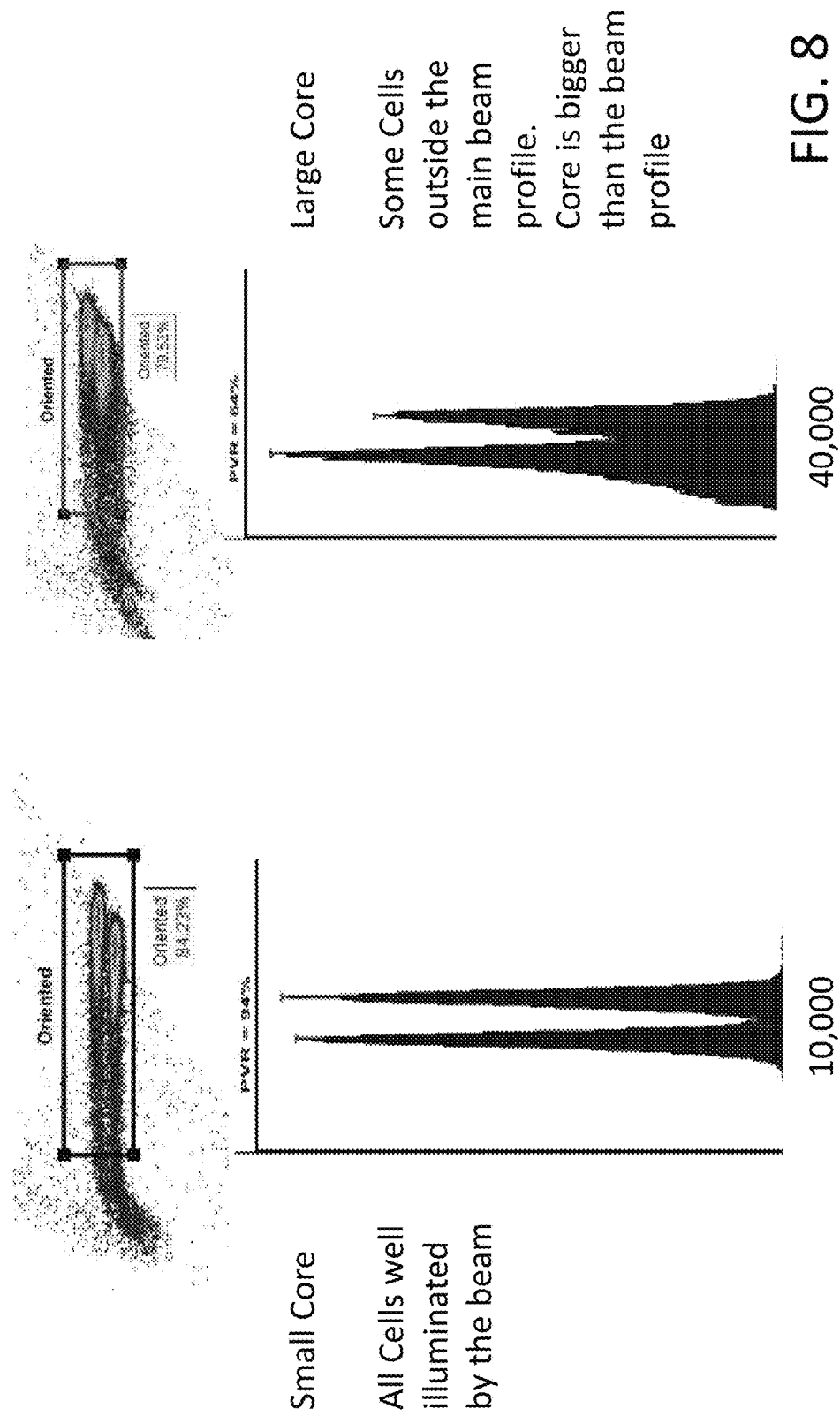
FIG. 8 shows a comparison between histograms of resulting sorting resolutions from use of a 70 μm width beam profile.
Figure 9:
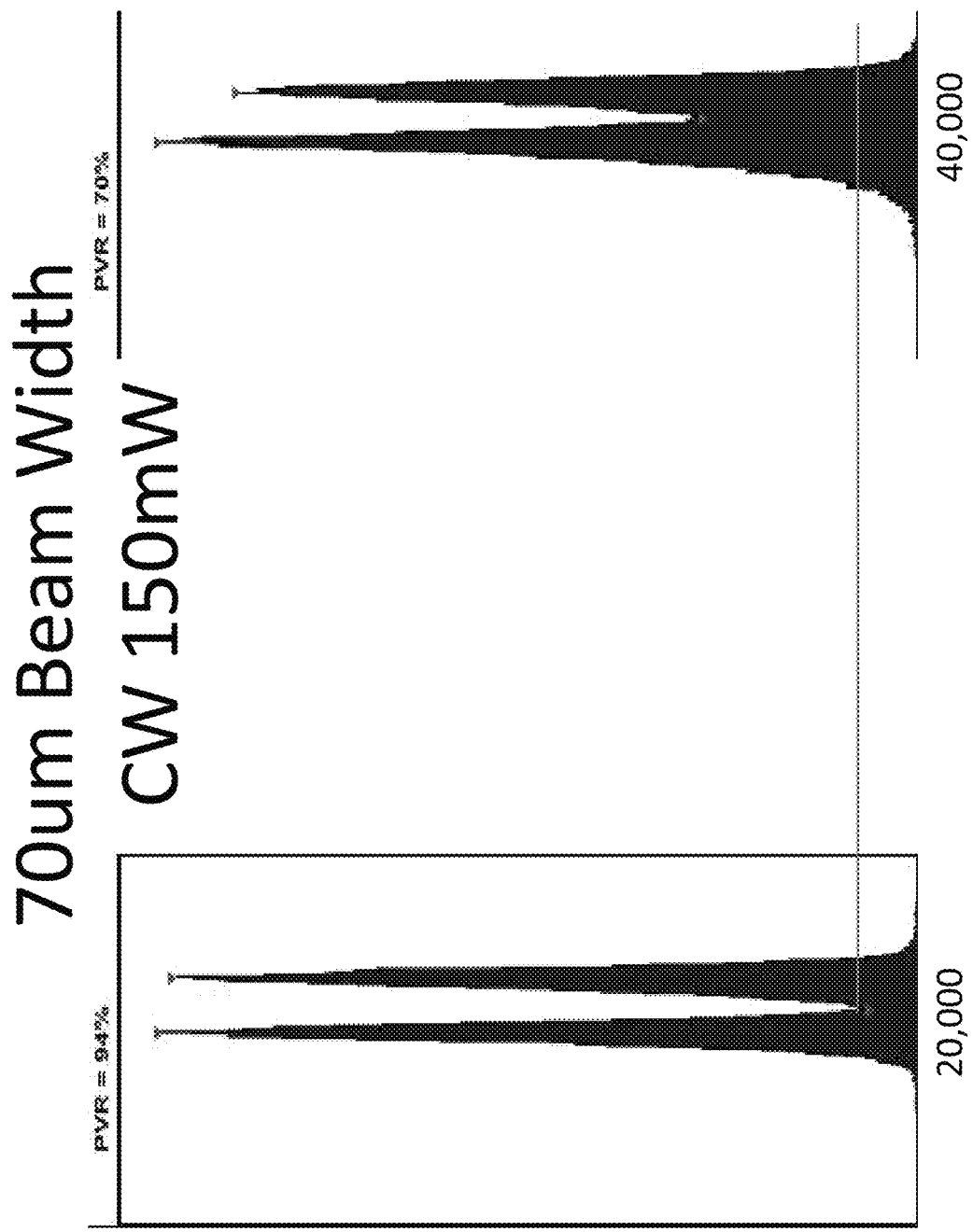
FIG. 9 shows a comparison between histograms of resulting sorting resolutions from use of a 70 μm width beam profile.

FIGS. 8 and 9 illustrate the results of experiments performed with beam shaping optics configured to modify the beam width of a Genesis CX-355 to have a beam width of 70 µm at the interrogation location of a MoFlo SX (Beckman Coulter, Miami Fla.) outfitted with a Genesis I digital upgrade (Cytonome/ST, Boston Mass.). Bovine nuclei were sorted at a concentration of 200 million nuclei per ml. While many flow cytometry applications can be calibrated and or tested with colored beads of various types, sperm sorting is unique in a number of respects and calibration is performed with sonicated sperm or sperm nuclei. Sperm nuclei provide better resolution than live sperm, but are unsuitable for use in artificial insemination because they are incapable of fertilization. Additionally, sperm nuclei are preferable for testing improved sorting techniques because they lack some of the variability and noise present in live sperm.

Referring now to FIG. 8, a comparison between histograms of resulting sorting resolutions from use of a 70 µm width beam profile is shown. Specifically, in this example, a continuous wave laser as used with an output power of 100 mW. The left histogram was obtained while the flow cytometer was operated at an event rate of 10,000 events per second, which is relatively slow. Because the event rate was relatively slow, the size of the corresponding core stream was relatively small. As a result, the majority of the sperm nuclei were well-illuminated by the laser beam having a width of 70 µm. Indeed, the core stream was illuminated so well that as shown in the top left bivariate plot of this example, 84.23% of the sperm nuclei were captured in the oriented region. Further, as shown in the histogram on the left, the PVR was 94%, indicating a very high sorting resolution between X- and Y-chromosome bearing sperm populations for the oriented sperm. This favorable sorting resolution occurred partly because at an event rate of 10,000 events per second, the core stream was relatively small, resulting in the inner core stream width facing the laser substantially matching a central portion of smaller beam width of 70 µm. For example, as determined by Applicant previously, an event rate of 10,000 events per second may correspond to an inner core stream width of about 26 µm. It may be appreciated that when the 70 µm beam is aligned with the core stream that an inner most portion of the beam which comprises just over one third of the total beam width has been matched to the core stream.

Still referring to FIG. 8, with respect to the histogram depicted on the right, the flow cytometer operated at an event rate of 40,000 events per second, which is relatively fast. Because the event rate was relatively fast, the size of the corresponding inner core stream was relatively large, as compared to the inner core stream at 10,000 events per second. As discussed with respect to FIG. 7, Applicant has determined the inner the core stream width at 40,000 events per second to be about 34 µm. The 70 µm beam width was mismatched for this relatively large inner core stream width. That is, the inner core stream width was larger than uniform center portion of the laser beam profile. As a result, an increasing number of sperm were not illuminated uniformly because they fell outside the substantially uniform and sufficiently powerful portion of the beam profile. Indeed, as shown in the top left bivariate plot of this example, only 79.53% of the sperm were captured in the oriented region. Further, as can be seen in the histogram on the right, the PVR was only 64% and the peaks were not very well defined, indicating a poor sorting resolution between X- and Y-chromosome bearing sperm subpopulations. Considering that a smaller percentage of nuclei were even in the histogram, it can be understood that losses in resolution can quickly compound in the sperm sorting application. A comparison between the histogram on the left with the histogram on the right demonstrates that when an inner core stream width substantially matches within a central portion of the beam width, in accordance with one or more embodiments of the present disclosure, less energy is wasted and a better sorting resolution between X- and Y-chromosome bearing sperm subpopulations is achieved.

FIG. 9 illustrates two histograms representative of sorting resolutions under similar conditions as FIG. 8. Specifically, the histograms were obtained in the same analytical instrument, but the continuous wave laser supplied a laser beam with an output power of 150 mW, as opposed to 100 mW. In the histogram on the left, the flow cytometer operated at an event rate of 20,000 events per second, which is relatively slow. As described previously, the slow event rate resulted in an inner core stream width, which was relatively small. As illustrated in FIG. 6, the inner core stream width at an event rate of 20,000 events per second is expected to be about 29 µm. The histogram on the left of FIG. 9 shows the PVR was 94%, indicating a very high sorting resolution between X- and Y-chromosome bearing sperm populations. It may be appreciated, there was no loss in performance in moving from 10,000 events per second to 20,000 events per second. This is because an event rate of 20,000 events per second is still relatively slow such that the corresponding inner core stream width was still substantially matched to the center portion of the beam width. Moreover, increasing the output power of the laser beam from 100 mW as shown in FIG. 8 to 150 mW as shown in FIG. 9 potentially compensated for any small loss in PVR that may have occurred at 20,000 events per second.

Still referring to FIG. 9, with respect to the resulting histogram on the right, the flow cytometer or analytical instrument operated at an event rate of 40,000 events per second, which is relatively fast. Because the event rate was relatively fast, the size of the corresponding core stream was relatively large. Specifically, Applicants believe this event rate provides an inner core stream width of about 33 µm. Reviewing the relatively poor PVR, it can be understood that the 70 µm beam width was mismatched for this relatively large inner core stream width. That is, the uniform center portion of the beam width was smaller than the inner core stream width resulting in sperm on the boundaries of the inner core stream receiving significantly different laser exposure as compared to those in the center portion of the inner core stream. Indeed, as shown in the histogram on the right of FIG. 9, while the PVR slightly improved from use of the continuous wave laser having a higher output power of 150 mW (as compared with the 100 mW continuous wave laser used in the example of FIG. 8), the PVR was still only 70% and the peaks were not very well defined, indicating a poor sorting resolution between X- and Y-chromosome bearing sperm subpopulations. A comparison between the histogram on the left with those on the right shows that when the width of the beam profile substantially matches the inner core stream width facing the laser, in accordance with one or more embodiments of the present disclosure, less energy is wasted and a better sorting resolution between X- and Y-chromosome bearing sperm subpopulations is achieved.

EXAMPLE 2

Referring now to FIGS. 10-25, Applicant performed another experiment with beam shaping optics configured to modify the beam width of a Genesis CX-355 (available from Coherent) to have a beam widths of 80 µm, 90 µm, 100 µm, and 110 µm at the interrogation location of a MoFlo SX sperm sorted (Beckman Coulter, Miami Fla.) outfitted with a Genesis I digital upgrade (Cytonome/ST, Boston Mass.). For each configuration and beam width, the laser was powered at 100 mw, 150 mw, 200 mw, and 250 mw. Again, each condition was tested at two event rates and bovine nuclei were sorted at a concentration of 200 million nuclei per ml.

Figure 10:
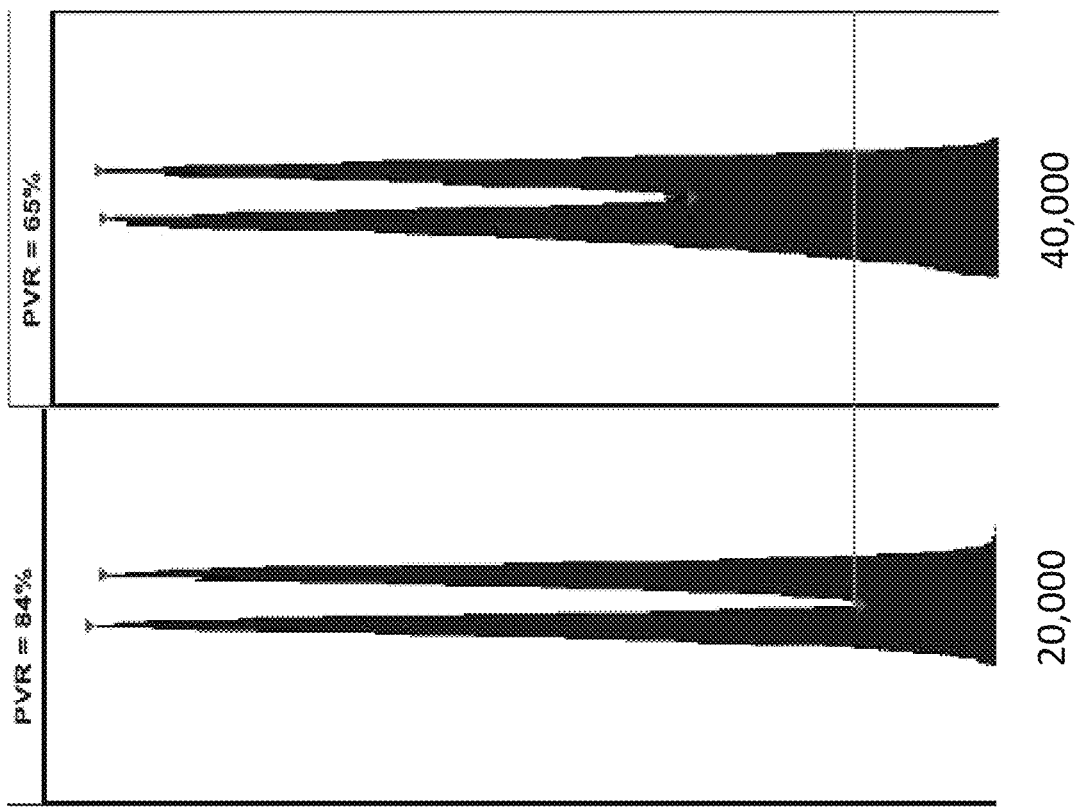
FIG. 10 shows a comparison between histograms of resulting sorting resolutions from use of an 80 μm width beam profile.

FIG. 10 illustrates a comparison of histograms generated at two different event rates with a 80 µm width beam profile. In this example, the continuous wave laser supplied laser beam having an output power of 100 mW. The histogram on the left illustrates the flow cytometer operated at an event rate of 20,000 events per second, which is relatively slow. Because the event rate was relatively slow, the size of the corresponding core stream was relatively small. As illustrated in FIG. 6, the inner core stream width at an event rate of 20,000 events per second is expected to be about 29 µm. The PVR of the left histogram was 76%, indicating only a moderate sorting resolution between X- and Y-chromosome bearing sperm populations. While an inner core stream width facing the laser at an event rate of 20,000 events per second may substantially match the center portion of an 80 µm beam width, the results represented by the left histogram of FIG. 10 suggest that the output power of 100 mW for the continuous wave laser used in this example may have been too low. With reference to the previous experiment illustrated in FIGS. 8 and 9, it may be appreciated that alignment of a flow cytometer is increasingly difficult at smaller beam widths. FIGS. 10-25 illustrate a clear trend, but it may be the case the instrument was extremely well aligned in the previous example.

Still referring to FIG. 10, the histogram on the right illustrates results obtained from the same flow cytometer operated at an event rate of 40,000 events per second, which is relatively fast. Because the event rate was relatively fast, the size of the corresponding core stream was relatively large, and in particular is expected to be about 33 µm. The middle portion of the 80 µm beam width was not substantially matched to the relatively large inner core stream width. That is, the inner core stream width facing the laser was too large for the uniform center portion of the beam profile. As a result, some of the sperm that were properly oriented still were not well-illuminated because they fell outside of the portion of the beam profile with sufficiently uniform laser energy flux. Indeed, as shown in the histogram on the right of FIG. 10, the PVR was only 63% (13% less than the PVR at 20,000 events per second) and the peaks were not very well defined, indicating a poor sorting resolution between X- and Y-chromosome bearing sperm subpopulations.

Figure 11:
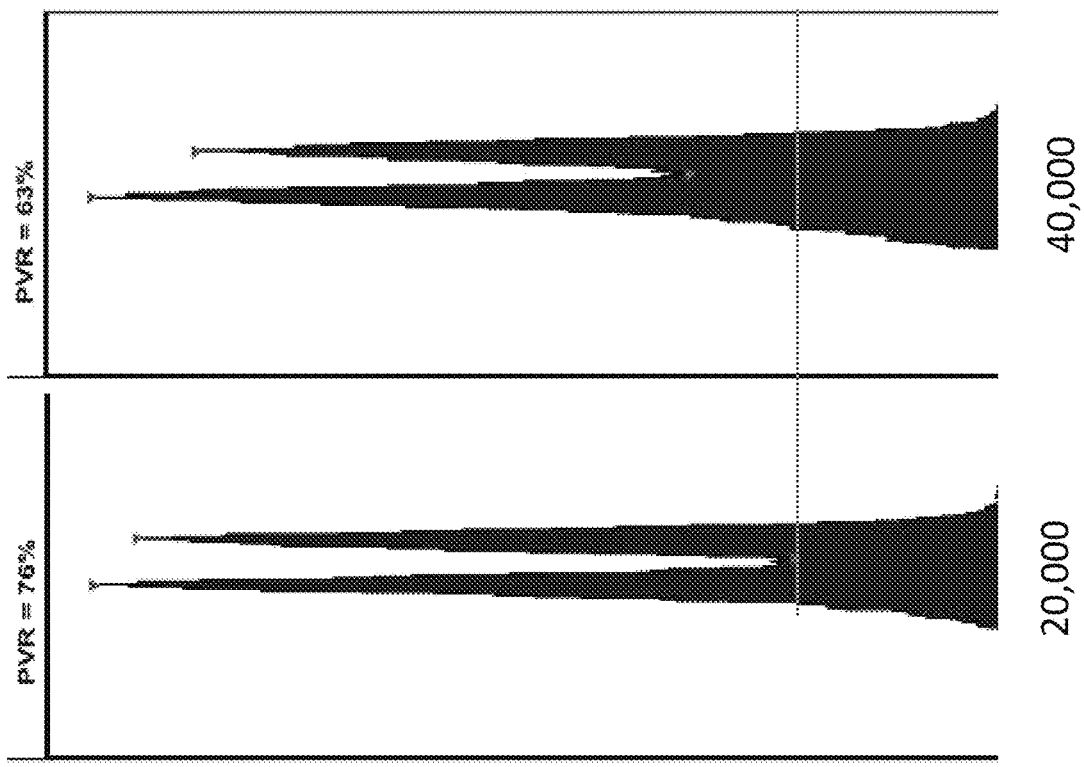
FIG. 11 shows a comparison between histograms of resulting sorting resolutions from use of an 80 μm width beam profile.
Figure 12:
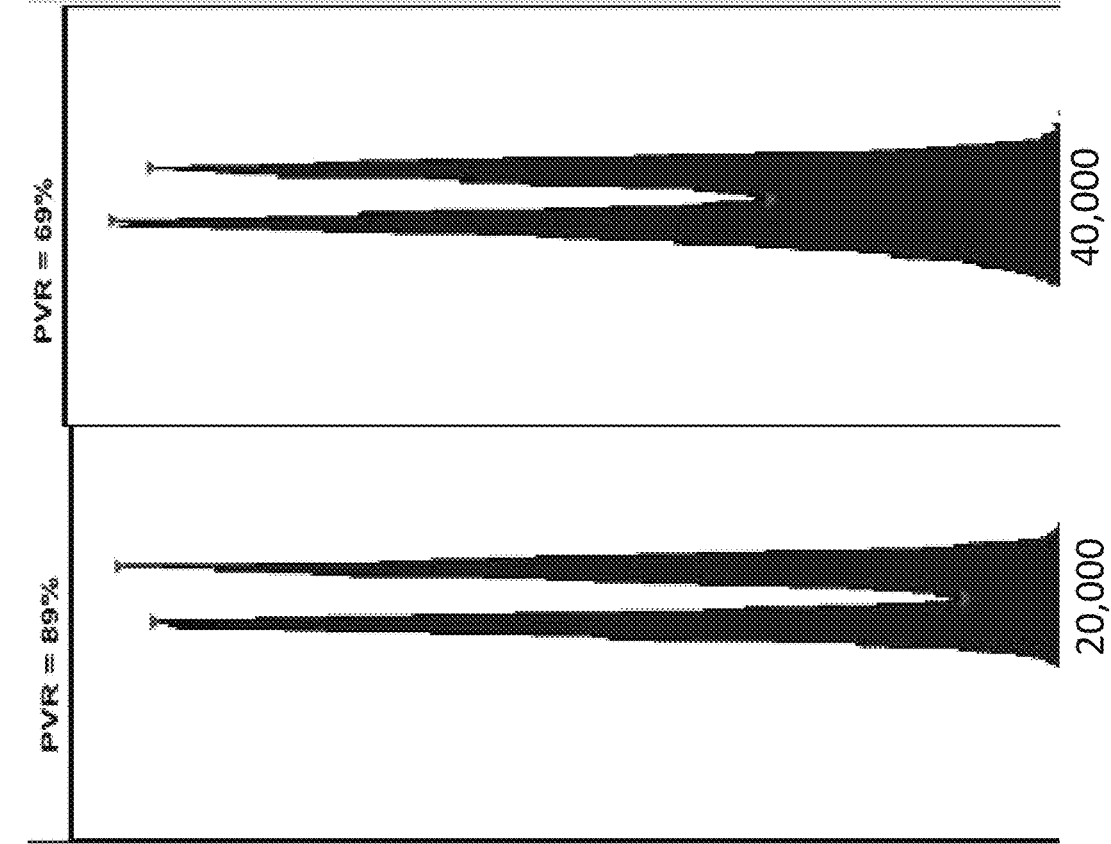
FIG. 12 shows a comparison between histograms of resulting sorting resolutions from use of an 80 μm width beam profile.
Figure 13:
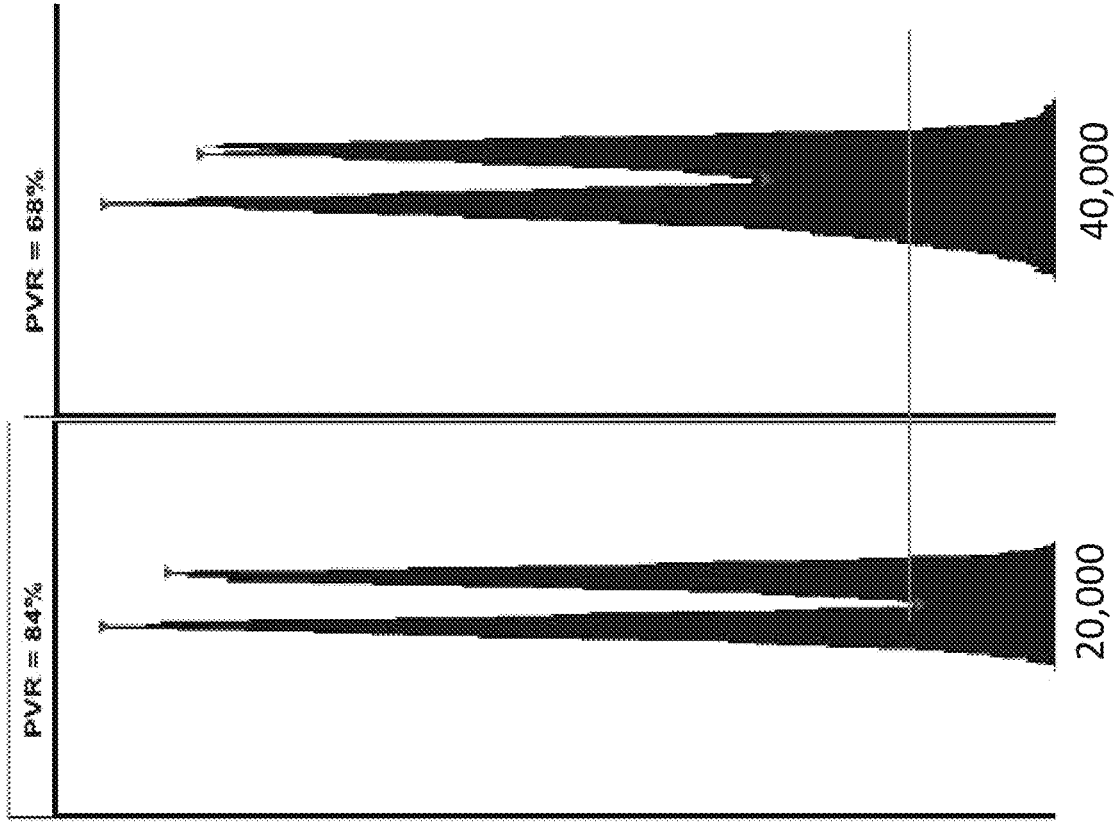
FIG. 13 shows a comparison between histograms of resulting sorting resolutions from use of an 80 μm width beam profile.

Referring now to FIGS. 11-13, a comparison between histograms of resulting sorting resolutions from use of an 80 µm width beam profile are shown. Specifically, FIGS. 11-13 show that increasing the output power of the continuous wave laser affects the resulting sorting resolutions when an 80 µm width beam profile is used.

The histograms generated in FIG. 11 were produced in response to a continuous wave laser having an output power of 150 mW. As further shown by the histogram on the left, increasing the output power of the continuous wave laser from 100 mW as shown in FIG. 10 to 150 mW as shown in FIG. 11 results in a higher PVR of 84% at an event rate of 20,000 events per second, and a slightly higher PVR of 65% at an event rate of 40,000 events per second. With respect to the results on the right of FIG. 11, however, the relatively fast event rate of 40,000 events per second produced a corresponding core stream that was relatively wide. The inner core stream width facing the laser was too large for and not substantially matched to the center portion of the beam profile. As a result, the PVR only improved to 65% when power was increased to 150 mW used, showing that increasing the laser power will have only a minimal improvement on the resulting sorting resolution if the beam profile width is mismatched from the core stream size. Indeed, FIGS. 12 and 13 exemplify the same.

The histograms generated in FIG. 12 were produced in response to a continuous wave laser having an output power of 200 mW. As further shown, increasing the output power of the continuous wave laser from 150 mW as shown in FIG. 12 to 200 mW as shown in FIG. 12 results in the same PVR of 84% at an event rate of 20,000 events per second, and a slightly higher PVR of 68% at an event rate of 40,000 events per second. With respect to the results on the right of FIG. 12, however, the relatively fast event rate of 40,000 events per second produced a corresponding core stream that was relatively large in size. And again, the inner core stream width facing the laser was too large for, and not substantially matched to, the center portion of the beam profile. As a result, the PVR only improved to 68% when a continuous wave laser having an output power of 200 mW was used, again demonstrating that increasing the laser power can only marginally improve sorting resolution if the center portion of the beam width is not matched to the core stream size.

FIG. 13 illustrates two histograms generated from a flow cytometer utilizing a continuous wave laser having an output power of 250 mW. As further shown, increasing the output power of the continuous wave laser from 200 mW as shown in FIG. 12 to 250 mW as shown in FIG. 13 results in an improved PVR of 89% at an event rate of 20,000 events per second, and a slightly higher PVR of 69% at an event rate of 40,000 events per second. With respect to the results on the right of FIG. 13, however, the relatively fast event rate of 40,000 events per second produced a corresponding core stream that was relatively large in size. Again, the inner core stream width facing the laser was too large for, and not substantially matched to, the center portion of the beam profile and as a result, the PVR only improved to 69% when a continuous wave laser having an output power of 250 mW was used.

Referring now to FIG. 14, a comparison between histograms representing sorting resolutions resulting from use of a 90 µm width beam profile in a flow cytometer is shown. In this example, a continuous wave laser provided output power of 100 mW was used. The results illustrated in the histogram on the left resulted from the flow cytometer being operated at an event rate of 20,000 events per second, which is relatively slow. Again, Applicant expects such event rates to correspond to an inner core stream width of 29 µm. As shown in the histogram on the left, the PVR was 91%, indicating a good sorting resolution between X- and Y-chromosome bearing sperm populations. This result suggests that the inner core stream width facing the laser, when the event rate is 20,000 events per second, substantially matches the center portion of the 90 µm beam width. As also shown by the histogram on the left of FIG. 14, a high sorting resolution may be achieved, even with a lower powered continuous wave laser, at low event rates of 20,000 events per second when the beam profile has a width of 90 µm.

Still referring to FIG. 14, the histogram depicted on the right was generated an event rate of 40,000 events per second, which is relatively fast. Because the event rate was relatively fast, the size of the corresponding core stream was relatively large. Again, the core stream generated at such an event rate is expected to have an inner core stream width of 33 µm. The center portion of the 90 µm beam width was only slightly mismatched for this relatively large inner core stream width facing the laser. As shown in the histogram on the right of FIG. 14, the PVR was 79%, indicating a fair sorting resolution between X- and Y-chromosome bearing sperm subpopulations. A comparison between the histogram on the left with the histogram on the right shows that when the width of the beam profile substantially matches the inner core stream width facing the laser (as indicated by results on the left), in accordance with one or more embodiments of the present disclosure, less energy is wasted, more sperm can be included in the oriented region, and a better sorting resolution between X- and Y-chromosome bearing sperm subpopulations is achieved. As compared to 80 µm, the beam width of 90 µm demonstrates an improved convergence of the PVRs at 20,000 events per second and 40,000 events per second.

Figure 16:
FIG. 16 shows a comparison between histograms of resulting sorting resolutions from use of a 90 μm width beam profile.
Figure 17:
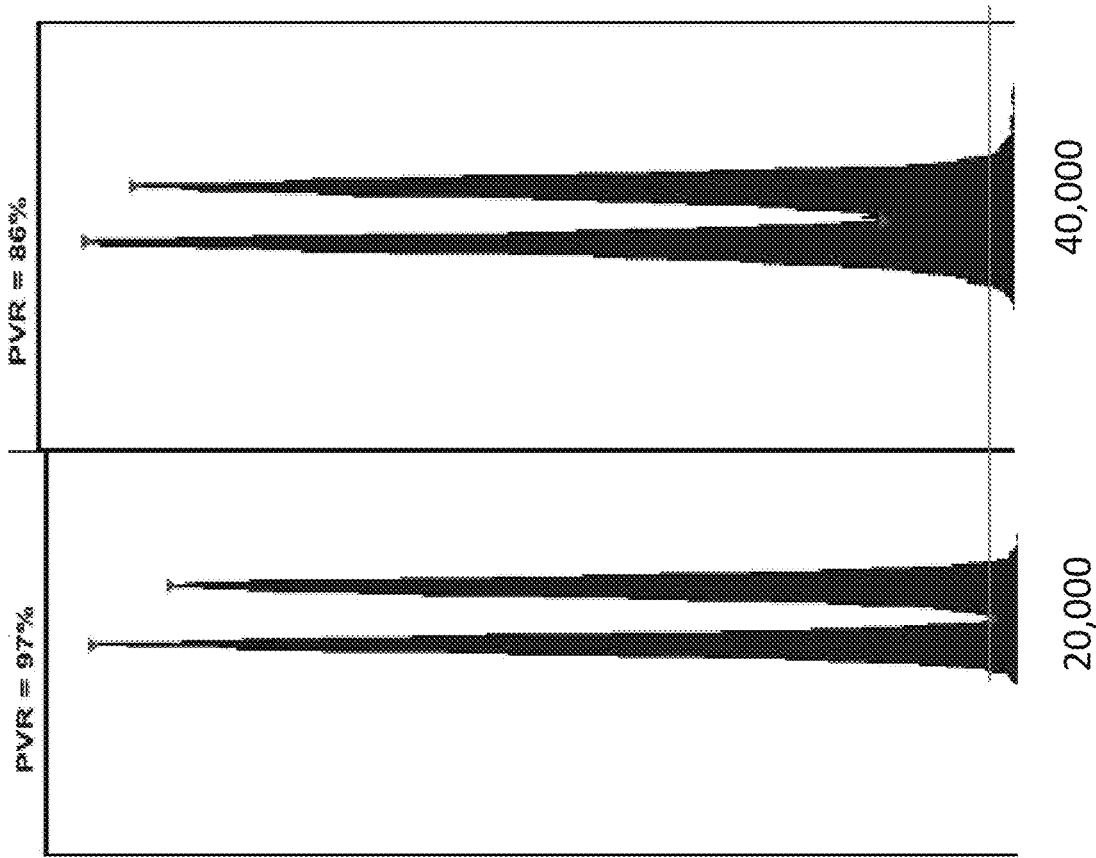
FIG. 17 shows a comparison between histograms of resulting sorting resolutions from use of a 90 μm width beam profile.

Referring now to FIGS. 15-17, a comparison between histograms of resulting sorting resolutions from use of a 90 µm width beam profile are shown. Specifically, FIGS. 15-17 show how increasing the output power of the continuous wave laser affects the resulting sorting resolutions when a 90 µm width beam profile is used.

FIG. 15 depicts two histograms generated from a flow cytometer utilizing a continuous wave laser having an output power of 150 mW. As can be understood from this figure, increasing the output power of the continuous wave laser from 100 mW (as shown in FIG. 14) to 150 mW (as shown in FIG. 15) results in the same PVR of 91% at an event rate of 20,000 events per second, and a slightly higher PVR of 82% at an event rate of 40,000 events per second. The 90 µm beam width was only slightly mismatched for the relatively large inner core stream width produced at 40,000 events per second. As a result, the PVR improved to 82% when a continuous wave laser having an output power of 150 mW was used, showing that increasing the laser power will have only a minimal improvement on the resulting sorting resolution if the center portion of the beam profile width is slightly mismatched from the inner core stream width.

FIG. 16 depicts two histograms generated from a flow cytometer utilizing a continuous wave laser having an output power of 200 mW. As can be understood from this figure, increasing the output power of the continuous wave laser from 150 mW (shown in FIG. 15) to 200 mW (shown in FIG. 16) results in an improved PVR of 97% at an event rate of 20,000 events per second, and an improved PVR of 86% at an event rate of 40,000 events per second. From FIG. 15, it can be seen that the increased output power of the continuous wave laser at 200 mW at least partially compensated for the slight mismatch between the center portion of the 90 µm beam width and the relatively large inner core stream.

FIG. 17 depicts two histograms generated from a flow cytometer utilizing a continuous wave laser having an output power of 250 mW. As can be understood from this figure, increasing the output power of the continuous wave laser from 200 mW (shown in FIG. 16) to 250 mW (shown in FIG. 17) results in a substantially similar PVR of 96% at an event rate of 20,000 events per second, and an improved PVR of 92% at an event rate of 40,000 events per second. Again, any slight mismatch between the center portion of the 90 µm beam width and the relatively large inner core stream width is largely compensated for by the increased output power of the continuous wave laser at 250 mW.

Figure 18:
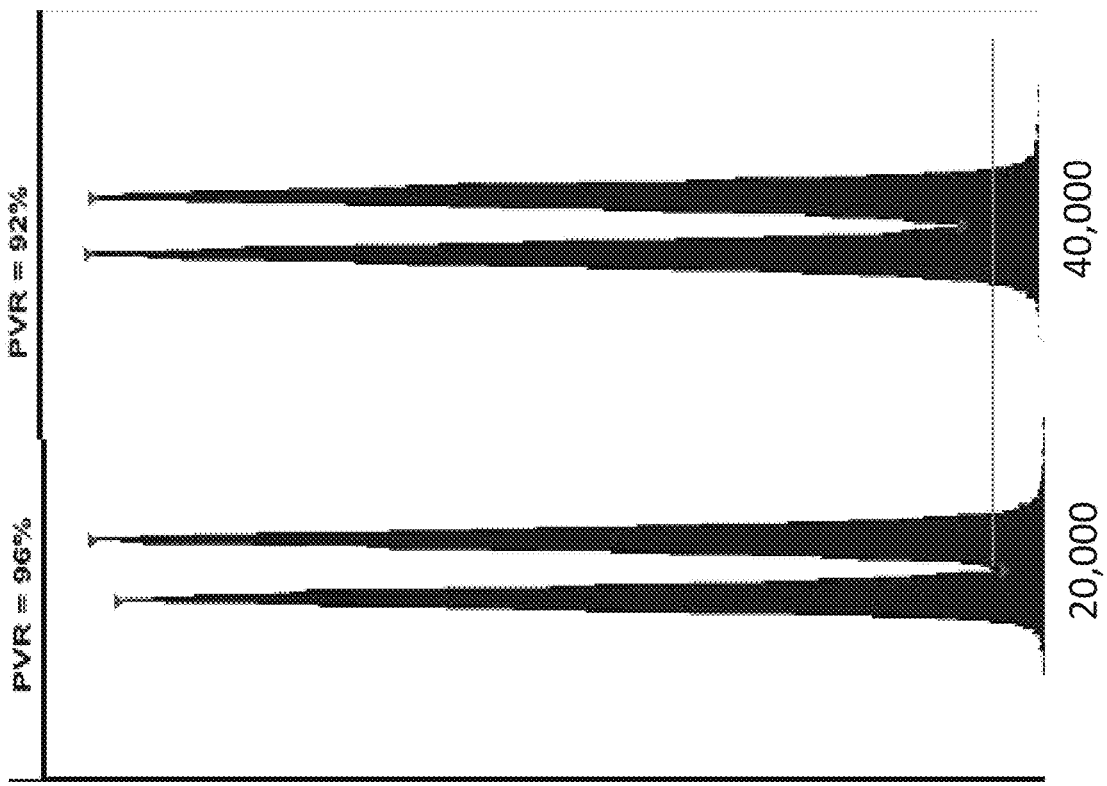
FIG. 18 shows a comparison between histograms of resulting sorting resolutions from use of a 100 μm width beam profile.

FIG. 18, a comparison between histograms representing sorting resolutions resulting from use of a 100 µm width beam profile is shown. Specifically, in this example, a continuous wave laser having an output power of 100 mW was used. The histogram on the left shows the resolution of a flow cytometer operated at an event rate of 20,000 events per second, which is relatively slow. Because the event rate was relatively slow, the size of the corresponding core stream was relatively small. The histogram on the left indicates a PVR of 91%, representing a good sorting resolution between X- and Y-chromosome bearing sperm subpopulations. This result suggests that the inner core stream width facing the laser when the event rate is 20,000 events per second substantially matches with the center portion of 100 µm beam width. As also shown by the histogram on the left of FIG. 18, a high sorting resolution may be achieved, even with a lower powered continuous wave laser, at low event rates of 20,000 events per second when the beam profile has a width of 100 µm.

FIG. 18 depicts a histogram on the right that results from a flow cytometer operated at an event rate of 40,000 events per second, which is relatively fast. Because the event rate was relatively fast, the size of the corresponding core stream was relatively large. However, the center portion of the 100 µm beam width substantially matched the relatively large inner core stream width facing the laser. Indeed, as shown in the histogram on the right of FIG. 18, the PVR was 89%, indicating a high sorting resolution between X- and Y-chromosome bearing sperm subpopulations. As shown by the histogram in FIG. 18, when the width of the beam profile substantially matches the inner core stream width facing the laser, in accordance with one or more embodiments of the present disclosure, less energy is wasted, more sperm are captured in the oriented region, and a better sorting resolution between X- and Y-chromosome bearing subpopulations is achieved. FIG. 18, also illustrates that when the beam width profile is 100 µm, very little PVR was lost when the event rate was increased from 20,000 events per second to 40,000 events per second. Additionally, the beam width of 100 demonstrates, at all powers, a significant convergence of the PVRs at 20,000 events per second and 40,000 events per second.

Figure 19:
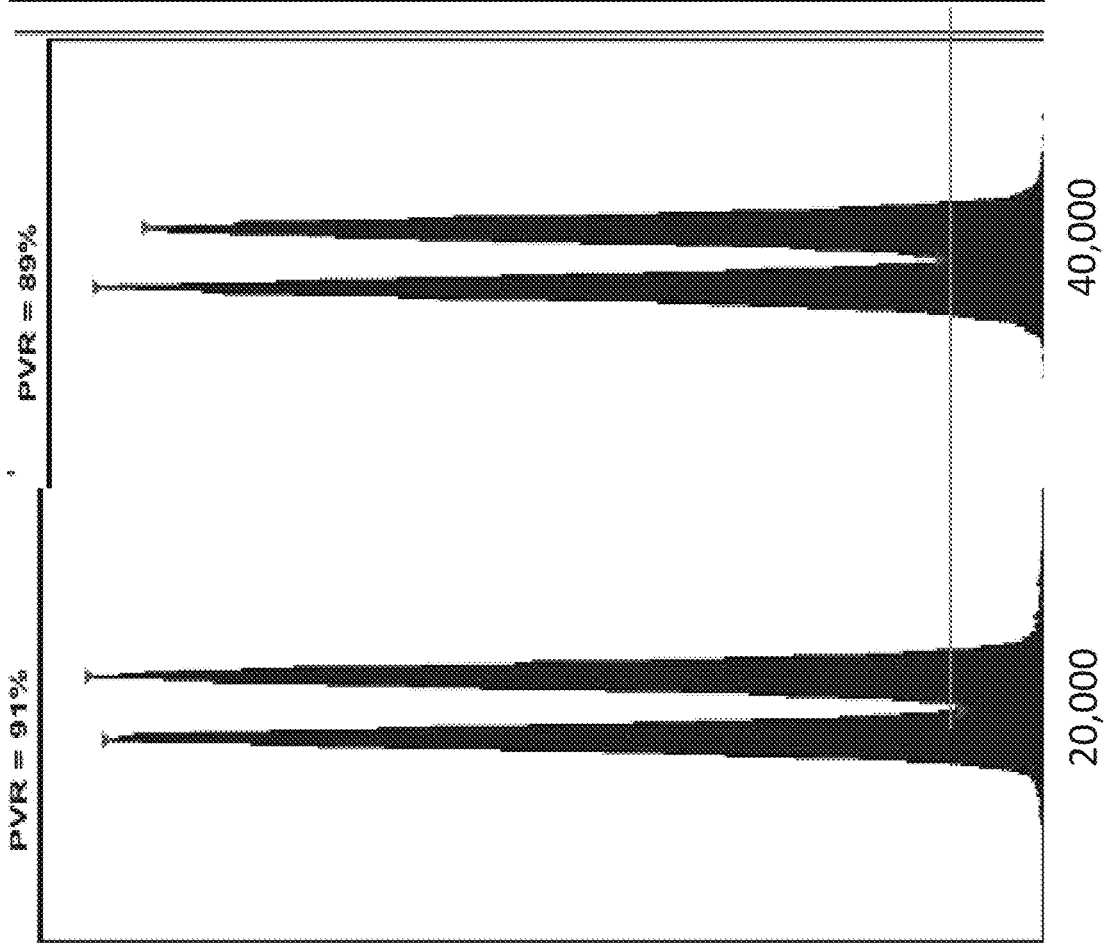
FIG. 19 shows a comparison between histograms of resulting sorting resolutions from use of a 100 μm width beam profile.

Referring now to FIGS. 19-21, a comparison between histograms of resulting sorting resolutions from use of a 100 µm width beam profile are shown. Specifically, FIGS. 19-21 illustrate how increasing the output power of the continuous wave laser affects the resulting sorting resolutions when a 100 µm width beam profile is used.

In FIG. 19 a continuous wave laser having an output power of 150 mW was used. With reference to FIG. 18, it can be understood that increasing the output power of the continuous wave laser from 100 mW (as shown in FIG. 18) to 150 mW (as shown in FIG. 19) resulted in a higher PVR of 96% at an event rate of 20,000 events per second, and a slightly higher PVR of 92% at an event rate of 40,000 events per second. With respect to the results on the right of FIG. 19, the relatively fast event rate of 40,000 events per second produced a corresponding core stream that was relatively large in size. However, the center portion of the 100 µm beam width substantially matched the relatively large inner core stream width facing the laser. Here, the PVR improved from 89% to 92% when a continuous wave laser having an output power of 150 mW was used, showing that increasing the laser power may slightly improve the resulting sorting resolution when the beam profile width substantially matches the inner core stream width facing the laser.

As shown in FIG. 20, a continuous wave laser having an output power of 200 mW was used. FIG. 20 demonstrates that increasing the output power of the continuous wave laser from 150 mW (as shown in FIG. 19) to 200 mW (as shown in FIG. 20) resulted in a slightly smaller PVR of 94% at an event rate of 20,000 events per second, and a slightly smaller PVR of 91% at an event rate of 40,000 events per second. Even though the PVR was slightly reduced when the output power of the continuous wave laser was increased to 200 mW in this example, a PVR of 94% at 20,000 events per second and a PVR of 91% at 40,000 events per second each indicate a high sorting resolution between X- and Y-chromosome bearing sperm subpopulations. While it may be the case that the flow cytometer was aligned slightly better during the portion of the experiment in which FIG. 19 was captured, the trend of FIGS. 18-21 illustrates diminishing returns on increasing the laser power when the center portion of the beam width is well matched to the inner core stream width. Furthermore, increasing the laser power of the continuous wave laser from 150 mW to 200 mW when the beam profile has a width of 100 µm may be unnecessary. Indeed, increasing the laser power did not improve the PVR, and setting the output power of the continuous wave laser to be as low as possible (without compromising the resulting sorting resolution) may preserve the health and fertility of the X- and Y-chromosome bearing sperm subpopulations. As well as increase the life of the laser decreasing down time and cost of the product by requiring laser replacement less frequently. In addition, allowing for lower cost, lower power lasers to be used.

As shown in FIG. 21, a continuous wave laser having an output power of 250 mW was used. As further shown, increasing the output power of the continuous wave laser from 200 mW (as shown in FIG. 20) to 250 mW (as shown in FIG. 21) resulted in a slightly smaller PVR of 93% at an event rate of 20,000 events per second, and an unchanged PVR of 91% at an event rate of 40,000 events per second. Even though the PVR was either slightly reduced or unchanged when the output power of the continuous wave laser was increased to 250 mW in this example, a PVR of 93% at 20,000 events per second and a PVR of 91% at 40,000 events per second each indicate a good sorting resolution between X- and Y-chromosome bearing sperm subpopulations. Further, increasing the laser power of the continuous wave laser from 200 mW (or even 150 mW) to 250 mW when the beam profile has a width of 100 µm may be unnecessary for the same reasons previously indicated.

FIG. 22 illustrates two histograms comparing sorting resolutions resulting from use of a 110 µm width beam profile. Specifically, in this example, a continuous wave laser output power supplied to the interrogation location was 100 mW. The histogram on the left was generated by a flow cytometer operated at an event rate of 20,000 events per second, which is relatively slow resulting in a smaller inner core stream width. The histogram on the left has a PVR of 94%, indicating a very high sorting resolution between X- and Y-chromosome bearing sperm subpopulations. This result suggests that the center portion of the 110 µm beam width substantially matches the inner core stream width facing the laser at the event rate 20,000 events per second. The histogram on the left of FIG. 22 also shows that a very high sorting resolution may be achieved, even with a lower powered continuous wave laser, at low event rates of 20,000 events per second when the beam profile has a width of 110 µm.

Still referring to FIG. 22, the resulting histogram on the right was generated in a flow cytometer operated at an event rate of 40,000 events per second, which is relatively fast resulting in a larger inner core stream width. However, the substantially uniform center portion of the 110 µm beam width substantially matched the relatively large inner core stream width facing the laser. Indeed, as shown in the histogram on the right of FIG. 22, the PVR was 86%, indicating a very good sorting resolution between X- and Y-chromosome bearing sperm subpopulations. As also shown by the histogram in FIG. 22, when the beam width profile is 110 µm, not much PVR is lost when the event rate is increased from 20,000 events per second to 40,000 events per second. FIG. 22 illustrates that a beam profile with a beam width of 110 µm provides an excellent option for sorting sperm at a variety of beam widths.

Referring now to FIGS. 22-25, a comparison between histogram of resulting sorting resolutions from use of a 110 µm width beam profile are shown. FIGS. 22-25 demonstrate how increasing the output power of the continuous wave laser affects the resulting sorting resolutions when a 110 µm width beam profile is used.

FIG. 23 shows the results of increasing the continuous wave laser power to 150 mW. At 150 mW the same PVR of 94% was measured at an event rate of 20,000 events per second as at 100 mW in FIG. 22. At 150 mW a higher PVR of 92% was measured at an event rate of 40,000 events per second. With respect to the results on the right in FIG. 23, the relatively fast event rate of 40,000 events per second produced a corresponding core stream that was relatively large in size. However, the center portion of the 110 µm beam width substantially matched the relatively large inner core stream width facing the laser. Here, the PVR improved from 86% to 92% when a continuous wave laser having an output power of 150 mW was used, showing that increasing the laser power when the beam profile has a width of 110 µm may achieve an even further improved sorting resolution.

FIG. 24 shows the results of further increasing the power of the continuous wave laser delivered to the interrogation location to 200 mW. At an event rate of 20,000 the histogram on the left shows the measured PVR of 97% events per second, which is even high than the results at 150 mW. At an event rate of 40,000 events per second the histogram on the left shows the measured PVR of 95%, which is also an improvement over 150 mW. Each PVR measured at 20,000 events per second and at 40,000 events per second each indicates a very high sorting resolution between X- and Y-chromosome bearing sperm subpopulations. This example demonstrates that increasing the laser power of the continuous wave laser from 150 mW to 200 mW when the beam profile has a width of 110 µm may achieve an even closer sorting resolution.

FIG. 25 shows the results of further increasing the power of the continuous wave laser delivered to the interrogation location to 250 mW. As further shown, increasing the output power of the continuous wave laser from 200 mW (as shown in FIG. 24) to 250 mW (as shown in FIG. 25) resulted in an unchanged PVR of 97% at an event rate of 20,000 events per second, and a slightly higher PVR of 96% at an event rate of 40,000 events per second. A PVR of 97% at 20,000 events per second and a PVR of 96% at 40,000 events per second each indicate a very high sorting resolution between X- and Y-chromosome bearing sperm subpopulations. As further shown by this example, increasing the laser power of the continuous wave laser from 200 mW to 250 mW when the beam profile has a width of 110 µm may achieve an even further improved sorting resolution.

FIGS. 22-24 demonstrate that a 110 µm beam width provides exceptional results, even at higher event rates of 40,000 events per second. That is, the center portion of a 110 µm beam width is substantially matched to the inner core stream width as event rates of both 20,000 and 40,000 events per second. Very little PVR is lost when the event rate is increased from 20,000 events per second to 40,000 events per second. Moreover, once the laser beam is modified to have a 110 µm beam width, the flow cytometer or analytical instrument easily and quickly achieves proper alignment, resulting in better performance and stability. That is, when a 110 µm beam width is used, the resulting sorting resolutions between X- and Y-chromosome bearing sperm subpopulations using the flow cytometer or analytical instrument are consistently favorable.

As previously mentioned with respect to the results shown in FIGS. 22-25, increasing the laser power of a continuous wave laser when the beam profile has a width of 110 µm may achieve even better results. Previously, those in the field of sperm sorting would not have sought to use continuous wave beam powers as high as 200 mw and higher. Early work with sperm sorting relied on water cooled Ion tube continuous wave lasers which provided broadband power, and raising the power of those lasers was shown to damage sperm resulting in poor fertility. Additionally, these broad band lasers needed to run at much higher current levels to get enough light to effectively resolve X and Y bearing sperm populations causing them to have relatively short lifetimes. These earlier broadband continuous wave lasers would last only a few thousand hours before requiring remanufacture as compared to newer DPSS (diode pumped solid state) lasers lasting in the 10's of thousands of hours. For at least this reason, and for reasons further explained below, pulsed lasers have been conventionally preferred for flow cytometry and sorting applications, and particularly for sorting sperm.

Although the flow cytometer used for the comparisons shown in FIGS. 8-25 operated at event rates of either 10,000 events per second, 20,000 events per second, or 40,000 events per second, it is also within the scope of the present disclosure for the analytical instrument to operate at an event rate between about 10,000 and about 20,000 events per second; between about 20,000 and about 30,000 events per second; between about 30,000 and about 40,000 events per second; between about 40,000 and about 50,000 events per second; between about 50,000 and about 60,000 events per second; between about 60,000 and about 70,000 events per second; between about 70,000 events per second and about 80,000 events per second; and between about 80,000 events per second and about 90,000 events per second.

FIGS. 26-28 provide three tables prepared in connection with the experiment which generated FIGS. 8-25. Referring now to FIG. 26, laser beam stability results were recorded by flow cytometer operators as a numerical range from 1 (unstable) to 10 (stable). The beam shaping optics of the continuous wave laser were first set to 70 µm, and the laser power was first set to 100 mW. Then, the sample to be sorted was placed on the sorter, and the sample was processed at 40,000 events per second. The results of this test were recorded in the chart as shown. Thereafter, the laser power was increased to 150 mW, then to 200 mW, and finally to 250 mW while the beam shaping optics of the continuous wave laser remained set at 70 µm, and all results were recorded in the chart. Then, these steps were repeated with the beam shaping optics of the continuous wave laser being set to 80 µm, 90 µm, 100 µm, and 110 µm, and all of these results were recorded in the chart as well.

As shown by the table in FIG. 26, any beam width size in the range of 70 µm to 110 µm has exceptional stability at higher continuous wave laser powers of 200 mW and 250 mW. As further shown by the results, beam profile widths in the range of 100 µm to 110 µm have exceptional stability at any continuous wave laser power in the range of 100 mW to 250 mW, even at lower the powers of 100 mW and 150 mW. As further shown by the results, a beam profile width of 90 µm has very good to exceptional stability at continuous wave laser powers in the range of 100 mW to 250 mW.

Referring now to FIG. 27, ease of alignment results from testing a continuous wave laser at various laser powers and various beam profile widths are shown. Operators familiar with aligning sperm sorters recorded numerical scores ranging from 1 (difficult alignment) to 10 (easy alignment) during this experiment. Specifically, the ease of alignment results are with respect to the ease of aligning a nuclei sample with a continuous wave laser. In this ease of alignment test, the beam shaping optics of the continuous wave laser were first set to 70 µm, and the laser power was first set to 100 mW. Then, the sample to be sorted was placed on the sorter, and the sample was processed at 40,000 events per second. The results of this test were recorded in the chart as shown. Thereafter, the laser power was increased to 150 mW, then to 200 mW, and finally to 250 mW while the beam shaping optics of the continuous wave laser remained set at 70 µm, and all results were recorded in the chart shown in FIG. 27. Then, these steps were repeated with the beam shaping optics of the continuous wave laser being set to 80 µm, 90 µm, 100 µm, and 110 µm, and all of these results were recorded in the chart as well.

As shown by the results of FIG. 27, the ease of alignment generally increases as the continuous wave laser power increases across all beam profile widths in the range of 70 to 110 µm. As further shown, beam profile widths in the range of 90 µm to 110 µm exhibit the best ease of alignment overall, regardless of the continuous laser power.

Referring now to FIG. 28, the PVR results recorded in each of FIGS. 9-25 at different event rates from testing a continuous wave laser at various laser powers and various beam profile widths are shown. In this test, the beam shaping optics of the continuous wave laser were first set to 80 µm, and the laser power was first set to 100 mW. Then, the sample to be sorted was placed on the sorter, the sample was processed at 20,000 events per second, and the PVR results were recorded in the chart. Then, the sample was processed at 40,000 events per second at these continuous wave laser settings, and the PVR results were recorded in the chart. Thereafter, the laser power was increased to 150 mW, then to 200 mW, and finally to 250 mW while the beam shaping optics of the continuous wave laser remained set at 80 µm, and all PVR results at event rates of 20,000 events per second and 40,000 events per second were recorded in the chart. Then, these steps were repeated with the beam shaping optics of the continuous wave laser being set to 90 µm, 100 µm, and 110 µm, and all of the PVR results at event rates of 20,000 events per second and 40,000 events per second were recorded in the chart as well. As shown, the PVR results are numerical, with numbers approaching 100 indicating a more favorable PVR result.

As shown by the PVR results of FIG. 28, beam profile widths in the range of 90 µm to 110 µm generally exhibit a high PVR at slower event rates of 20,000 events per second. At higher event rates of 40,000 events per second beam profile widths in the range of 100 µm to 110 µm performed the best with respect to PVR. As further shown, with a few exceptions or outliers, the PVR generally improved as the continuous wave laser beam power was increased. Viewing the trends in FIG. 28, generally, it appears the testing performed at 80 µm may not have been performed in an ideal alignment. Indeed, FIG. 27 shows that operators regarded 80 µm as somewhat difficult to align (scoring it as 4). It is also possible performance drops off drastically at beam widths approaching the diameter of the outer stream (70 µm nozzle tips were used, meaning the diameter of the outer stream is about 70 µm as well).

EXAMPLE 3

A third experiment sought to determine how low the power could be set on the continuous wave laser while still achieving acceptable sperm sorting resolution with a beam width of 110 µm. Again, a Genesis CX-355 laser was utilized for interrogating sperm nuclei at the interrogation location of a MoFlo SX (Beckman Coulter, Miami Fla.) outfitted with a Genesis I digital upgrade (Cytonome/ST, Boston Mass.). Bovine nuclei were supplied in sample at a concentration of 200 million nuclei per ml.

Figure 29:
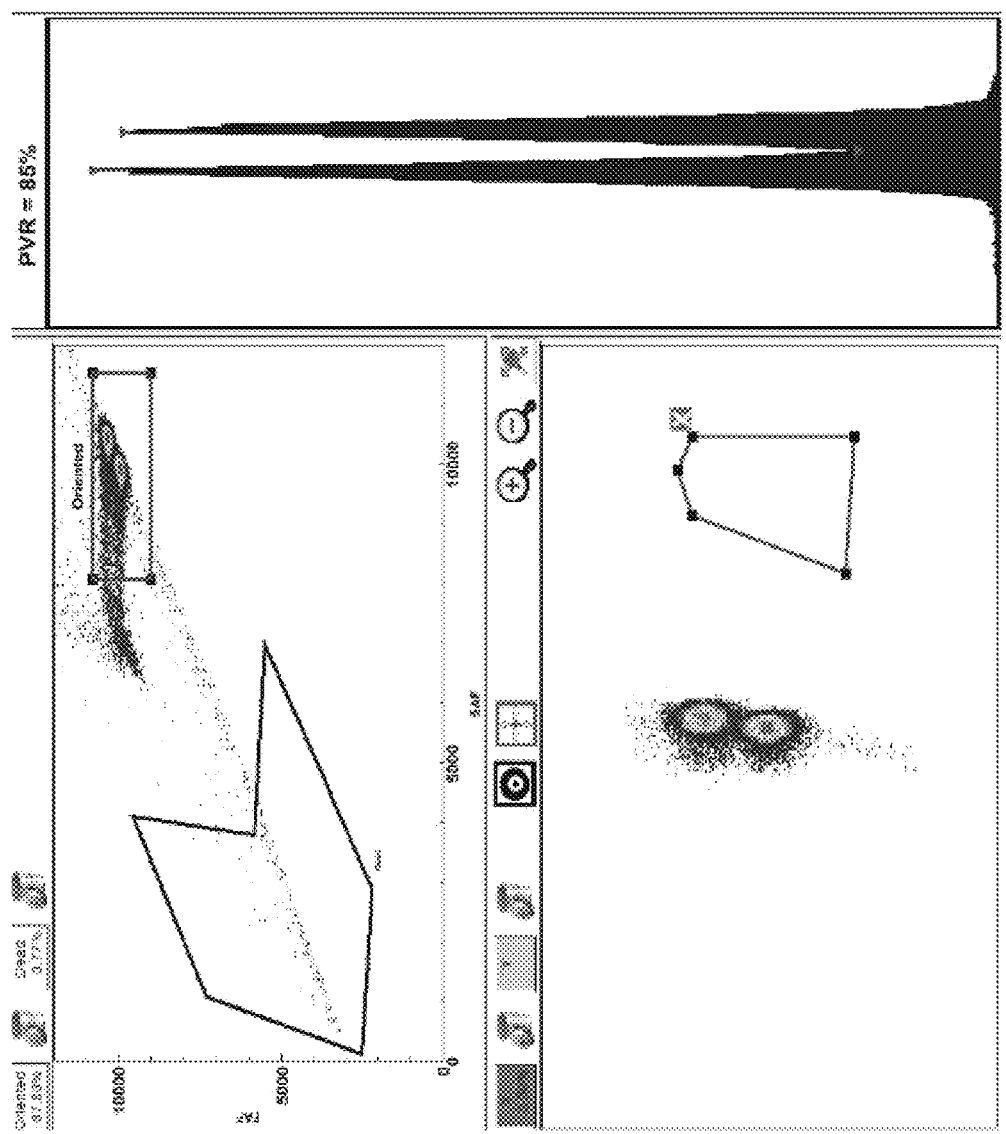
FIG. 29 shows examples of bivariate plots and corresponding histogram of a resulting sorting resolution as visualized on a flow cytometer monitor from use of a 110 μm width beam profile and a 10 mW continuous wave laser.

Referring now to FIG. 29, bivariate plots and a corresponding histogram quantifying resulting sorting resolution, as visualized on a flow cytometer monitor utilizing a 110 µm width beam profile and a 10 mW continuous wave laser are shown. As previously mentioned, according to one or more embodiments of the present disclosure, the analyzer 13 analyzes the forward fluorescence of the DNA selective light emission material as detected by the first detector 11a, and the side fluorescence of the DNA selective light emission material as detected by the second detector 11b. Accordingly, the top bivariate plot of FIG. 29 illustrates peak forward fluorescence and peak side fluorescence at an event rate of 10,000 events per second. From this plot, sperm nuclei which are oriented and suitable for sorting are easily identifiable. As shown, 87.88% of the sperm nuclei were captured in the oriented region. While a dead region is illustrated it may be appreciated that sperm nuclei are not stained with a dead quenching dye. Only the oriented sperm are plotted in the second bivariate plot at the bottom of the screen. In the second plot, oriented subpopulations of X- and Y-chromosome bearing sperm are shown. From this second plot, a sort region may be drawn by an operator around the subpopulation of interest. As shown in the example of FIG. 29, however, the sort region has not been drawn around either of the subpopulations.

Still referring to FIG. 29, the flow cytometer or analytical instrument according to one or more embodiments of the present disclosure may include a software package, such as the previously described population tracking software for example, which tracks the center of mass of certain populations of data. For example, as the two very close subpopulations in the bottom bivariate plot of FIG. 29 drift over time, population tracking software would attempt to keep the "X" region over the top subpopulations of X chromosome bearing sperm.

Still referring to FIG. 29, the right side of the flow cytometer monitor image shows corresponding a histogram indicating a resolution between X- and Y-chromosome bearing sperm subpopulations from use of a continuous wave laser having an output power of 10 mW and an event rate of 10,000 events per second. In this example, the PVR was 85%, which is a very good sorting resolution between X- and Y-chromosome bearing sperm subpopulations.

Still referring to FIG. 29, the results shown in the flow cytometer monitor of this example are both surprising and unexpected. An output power of only 10 mW means that the continuous wave laser used in this example was outputting very little power. Further, the flow cytometer or analytical instrument operated at an event rate of 10,000 events per second, which is relatively slow. Because the event rate was relatively slow, the size of the corresponding core stream was relatively small. As a result, the majority of the sperm nuclei were well-illuminated by the laser beam having a width of 110 µm and were able to be included in the oriented region. What is surprising is that, when the laser beam has a width of 110 µm, a PVR of 85% may be achieved, indicating a very good sorting resolution between X- and Y-chromosome bearing sperm subpopulations, even if the output power of the continuous wave laser is only 10 mW. While the resulting PVR of this example was due in part to the slow event rate of 10,000 events per second, these results cannot be achieved with a 160 µm beam profile width at such a low laser output power level. Accordingly, these results show that at low event rates, very little laser power is needed to achieve a favorable sorting resolution between X- and Y-chromosome bearing sperm subpopulations when the laser beam has a width of 110 µm. Significantly, because less laser power is needed, continuous wave lasers having a smaller footprint and much higher lifetimes may be used, and the health and fertility of the X- and Y-chromosome bearing sperm subpopulations may be preserved and/or improved.

Figure 30:
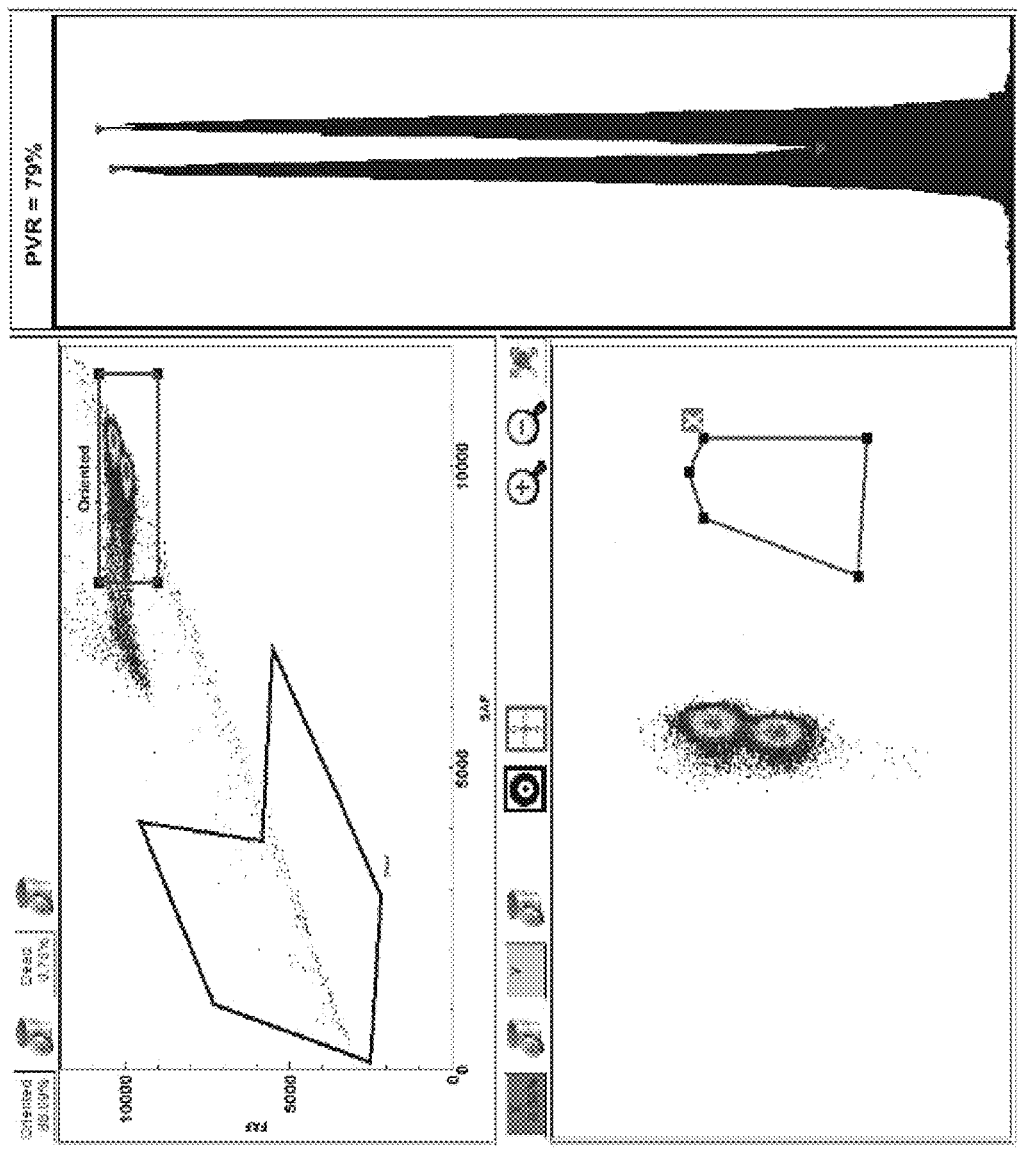
FIG. 30 shows examples of bivariate plots and corresponding histogram of a resulting sorting resolution as visualized on a flow cytometer monitor from use of a 110 μm width beam profile and a 10 mW continuous wave laser.

FIG. 30 shows bivariate plots and corresponding a histogram generated on a flow cytometer monitor utilizing a 110 µm width beam profile and a 10 mW continuous wave laser at an event rate of 20,000 events per second. The top bivariate plot of FIG. 30 illustrates peak forward fluorescence and peak side fluorescence. From this plot, the oriented sperm are easily identifiable. As shown, 88.09% of the sperm were included in the oriented sperm region. A comparison between this plot of FIG. 30 and the corresponding plot of FIG. 29 shows that about the same percentage of sperm had the proper orientation when the event rate was increased from 10,000 events per second to 20,000 events per second. That is, increasing the event rate did not adversely impact the number of sperm nuclei collected in the oriented region. Only events in the oriented region are plotted in the second bivariate plot at the bottom of the screen. In the second plot, subpopulations of X- and Y-chromosome bearing sperm nuclei are shown. From this second plot, a sort region may be drawn by an operator around the subpopulation of interest. As shown in the example of FIG. 30, however, the sort region has not been drawn around either of the subpopulations. As previously described, a population tracking software package may be used in accordance with one or more embodiments of the present disclosure to attempt to keep the "X" Region over the top population of cells as the two very close subpopulations in the bottom bivariate plot of FIG. 30 drift over time.

Still referring to FIG. 30, the right side of the flow cytometer monitor shows corresponding histogram quantifying the sorting resolution between X- and Y-chromosome bearing sperm subpopulations from use of a 110 µm width beam profile, and a continuous wave laser having an output power of 10 mW at an event rate of 20,000 events per second. In this example, the PVR was 79%, indicating that some PVR was lost when the event rate was increased from 10,000 events per second, as shown in FIG. 29, to 20,000 events per second, as shown in FIG. 30. These results show that as the event rate was increased to 20,000 events per second, the inner core stream width facing the laser did not substantially match with the beam profile width used.

Figure 31:
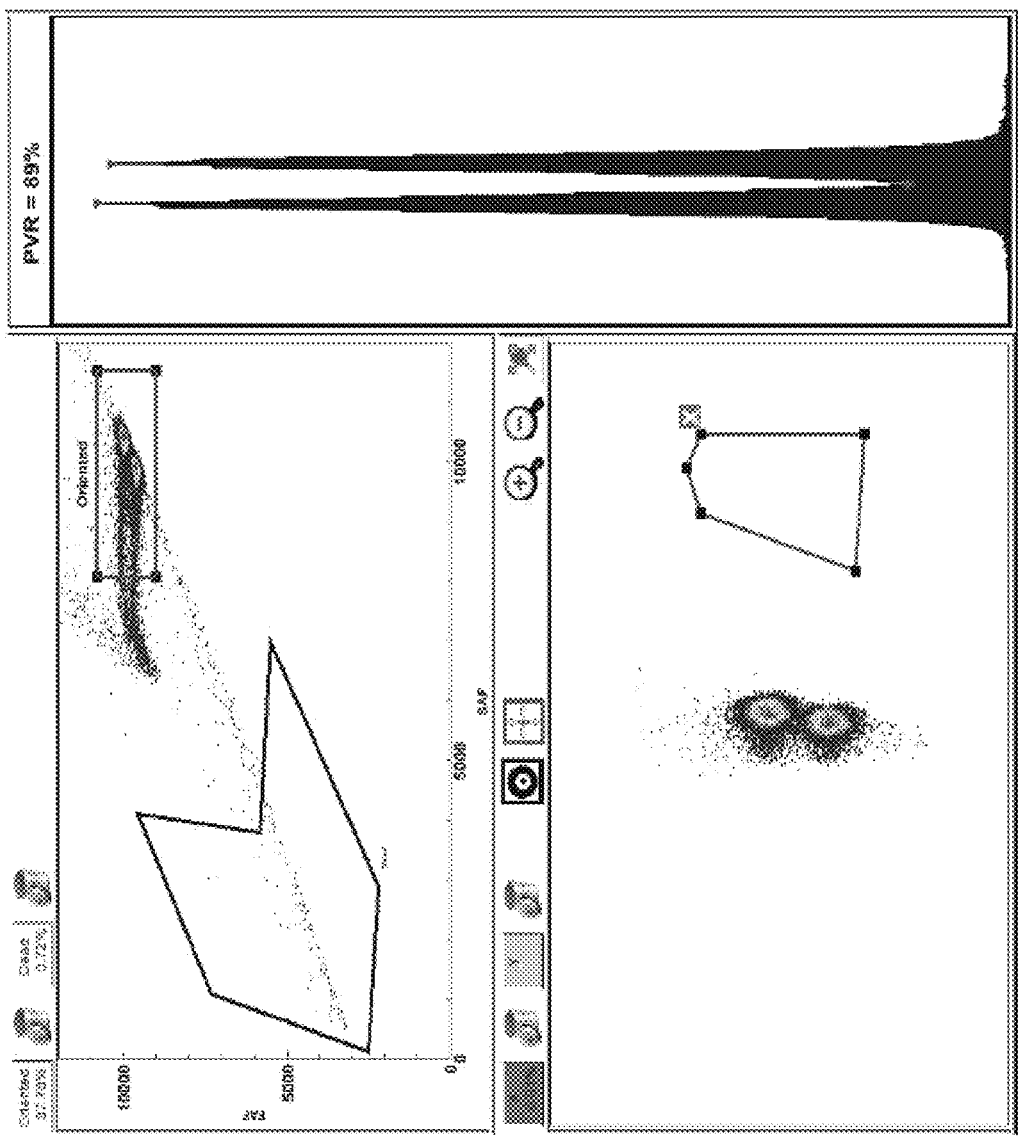
FIG. 31 shows examples of bivariate plots and corresponding histogram of a resulting sorting resolution as visualized on a flow cytometer monitor from use of a 110 μm width beam profile and a 25 mW continuous wave laser.

Referring now to FIG. 31, bivariate plots and a corresponding histogram generated on a flow cytometer monitor utilizing a 110 µm width beam profile and a 25 mW continuous wave laser are shown. The top bivariate plot of FIG. 31 illustrates peak forward fluorescence and peak side fluorescence at an event rate of 10,000 events per second. From this plot, the oriented sperm are easily identifiable. As shown, 87.78% of the sperm nuclei were included in the oriented region. Only events included in the oriented region are plotted in the second bivariate plot at the bottom of the screen. In the second bivariate plot, subpopulations of X- and Y-chromosome bearing sperm are shown as two very close clusters of events. From this second plot, a sort region may be drawn by an operator around the subpopulation of interest. As shown in the example of FIG. 31, however, the sort region has not been drawn around either of the subpopulations. As previously described, a population tracking software package may be used in accordance with one or more embodiments of the present disclosure to attempt to keep the "X" subpopulation over the top population of cells as the two very close subpopulations in the bottom bivariate plot of FIG. 31 drift over time.

Still referring to FIG. 31, the right side of the flow cytometer monitor shows a corresponding histogram which quantifies the sorting resolution between X- and Y-chromosome bearing sperm nuclei subpopulations from use of a 110 µm width beam profile and a continuous wave laser having an output power of 25 mW at an event rate of 10,000 events per second. In this example, the PVR was 89%, which is a very good sorting resolution between X- and Y-chromosome bearing sperm subpopulations. Furthermore, a slight increase in the power from 10 mW to 25 mW was able to improve resolution a little at an event rate of 10,000 events per second.

Still referring to FIG. 31, the results shown in the flow cytometer monitor of this example are both surprising and unexpected. 25 mW is well below typical laser powers for sorting sperm, which generally use as much as about 175 mW of laser power at a beam width of 160 µm. However, because the center portion of the 110 µm beam width is substantially matched to the inner core stream width at an event rate of 10,000 events per second improved results are seen. What is surprising is that, when the laser beam has a width of 110 µm, a PVR of 89% may be achieved, indicating a very good sorting resolution between X- and Y-chromosome bearing sperm subpopulations, even if the output power of the continuous wave laser is only 25 mW. While the resulting PVR of this example was due in part to the slow event rate of 10,000 events per second and the slightly increased laser power from 10 mW, as shown in FIG. 29, to 25 mW, as shown in FIG. 31, these results cannot be achieved with a 160 µm beam profile width at such a low laser output power level. Accordingly, these results show that at low event rates, magnitudes less laser power is needed to achieve a favorable sorting resolution between X- and Y-chromosome bearing sperm subpopulations when the laser beam has a width of 110 µm. Significantly, because less laser power is needed, continuous wave lasers having a smaller footprint may be used, and the health and fertility of the X- and Y-chromosome bearing sperm subpopulations may be preserved or in fact improved by using less stain on the sperm samples during staining.

Figure 32:
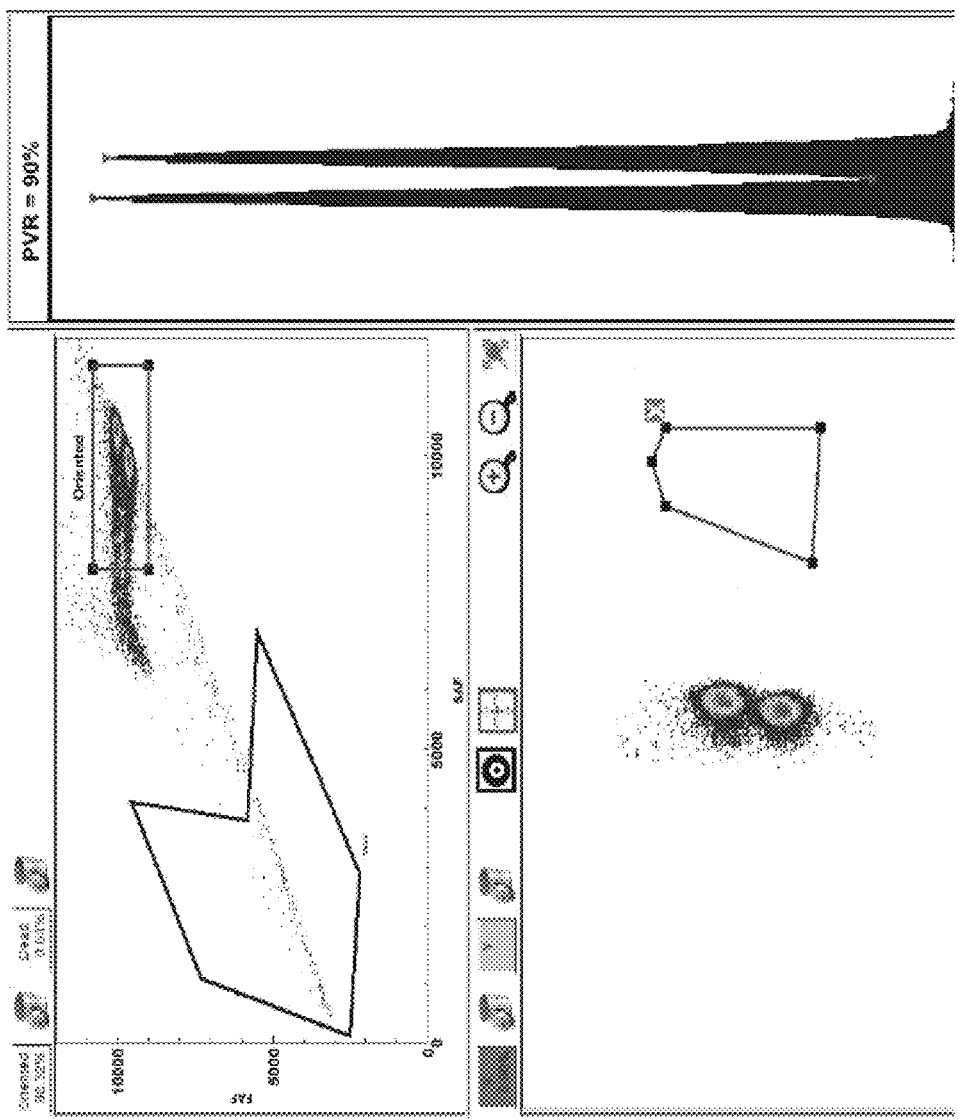
FIG. 32 shows examples of bivariate plots and corresponding histogram of a resulting sorting resolution as visualized on a flow cytometer monitor from use of a 110 μm width beam profile and a 25 mW continuous wave laser.

FIG. 32 shows bivariate plots and a corresponding histogram quantifying a sorting resolution as visualized on a flow cytometer monitor utilizing a 110 µm width beam profile and a 25 mW continuous wave laser are shown. Again, the top bivariate plot of FIG. 32 illustrates the peak forward fluorescence and the peak side fluorescence of detected events operating at an event rate of 20,000 events per second. From this plot, the oriented sperm are easily identifiable. As shown, 88.32% of the sperm nuclei were captured in the oriented region. A comparison between this plot of FIG. 32 and the corresponding plot of FIG. 31 shows that the resolution permitted the same percentage of sperm nuclei to be captured in the oriented region when the event rate was increased from 10,000 events per second to 20,000 events per second. That is, increasing the event rate did not adversely affect instruments resolution. Only sperm nuclei in the oriented region of the first bivariate plot are included in the second bivariate plot at the bottom of the screen. In the second plot, subpopulations of X- and Y-chromosome bearing sperm are shown. From this second plot, a sort region may be drawn by an operator around the subpopulation of interest. As shown in the example of FIG. 32, however, the sort region has not been drawn around either of the subpopulations. As previously described, a population tracking package may be used in accordance with one or more embodiments of the present disclosure to attempt to keep the "X" subpopulation over the top population of cells as the two very close subpopulations in the bottom bivariate plot of FIG. 32 drift over time.

Still referring to FIG. 32, the right side of the flow cytometer monitor shows a histogram representing the sorting resolution between subpopulations of X- and Y-chromosome bearing sperm nuclei in a flow cytometer using a continuous wave laser with an output power of 25 mW and an event rate of 20,000 events per second. In this example, the PVR was 90%, indicating a high sorting resolution between X- and Y-chromosome bearing sperm nuclei. These results also indicate that no PVR was lost when the event rate was increased from 10,000 events per second (as shown in FIG. 31) to 20,000 events per second (as shown in FIG. 32). When compared to FIG. 30, as previously described, these results show that slightly increasing the laser output power from 10 mW to 25 mW significantly improves the PVR at the faster event rate of 20,000 events per second. As understood by those having ordinary skill in the art, a laser output power of 25 mW is still very low. Accordingly, these results show that at event rates of 20,000 events per second, a very low amount of laser power is needed to achieve a favorable sorting resolution between X- and Y-chromosome bearing sperm subpopulations when the laser beam has a width of 110 µm. Significantly, because less laser power is needed, continuous wave lasers having a smaller footprint may be used, and the health and fertility of the X- and Y-chromosome bearing sperm subpopulations may be preserved or in fact improved.

EXAMPLE 4

Beam stability can be greatly improved with a reduced beam path as compared to conventional flow cytometers, and as exemplified in this Example 4, this improvement results in better sorting resolution, as well as better sorting speeds and efficiency. Referring now to FIGS. 33-37, various results are illustrated that highlight these benefits. Briefly, in this experiment live bovine sperm was sorted on two sperm sorting systems. The first sperm sorting system was a MoFlo SX (Beckman Coulter, Miami Fla.) modified with the Genesis I digital upgrade (Cytonome/ST, Boston Mass.) including a continuous wave Coherent Genesis CX-355 laser. The second sperm sorter was also a MoFlo SX modified with the Genesis I digital upgrade, but served as a control system for comparison and utilized a Vanguard 350-355 pulsed laser with conventional beam shaping optics and a conventional beam path of 35 inches.

In the experiment, sperm originating from a single bull were stained, and the stained live sample was divided into two aliquots. One aliquot sorted in the first system with the Coherent Genesis CX-355 continuous wave laser. The beam path was established at 6 inches and the sperm was sorted at an event rate of 40,000 event per second until a target of 90 million cells having a 90% purity of X-chromosome bearing sperm was reached. As previously described the beam width of 110 µm has a center portion which is substantially matched to an inner core stream of a flow cytometer operating at an event rate of 40,000 events per second. Accordingly, the first system may be referred to throughout this example as the modified sperm sorting system.

Figure 33:
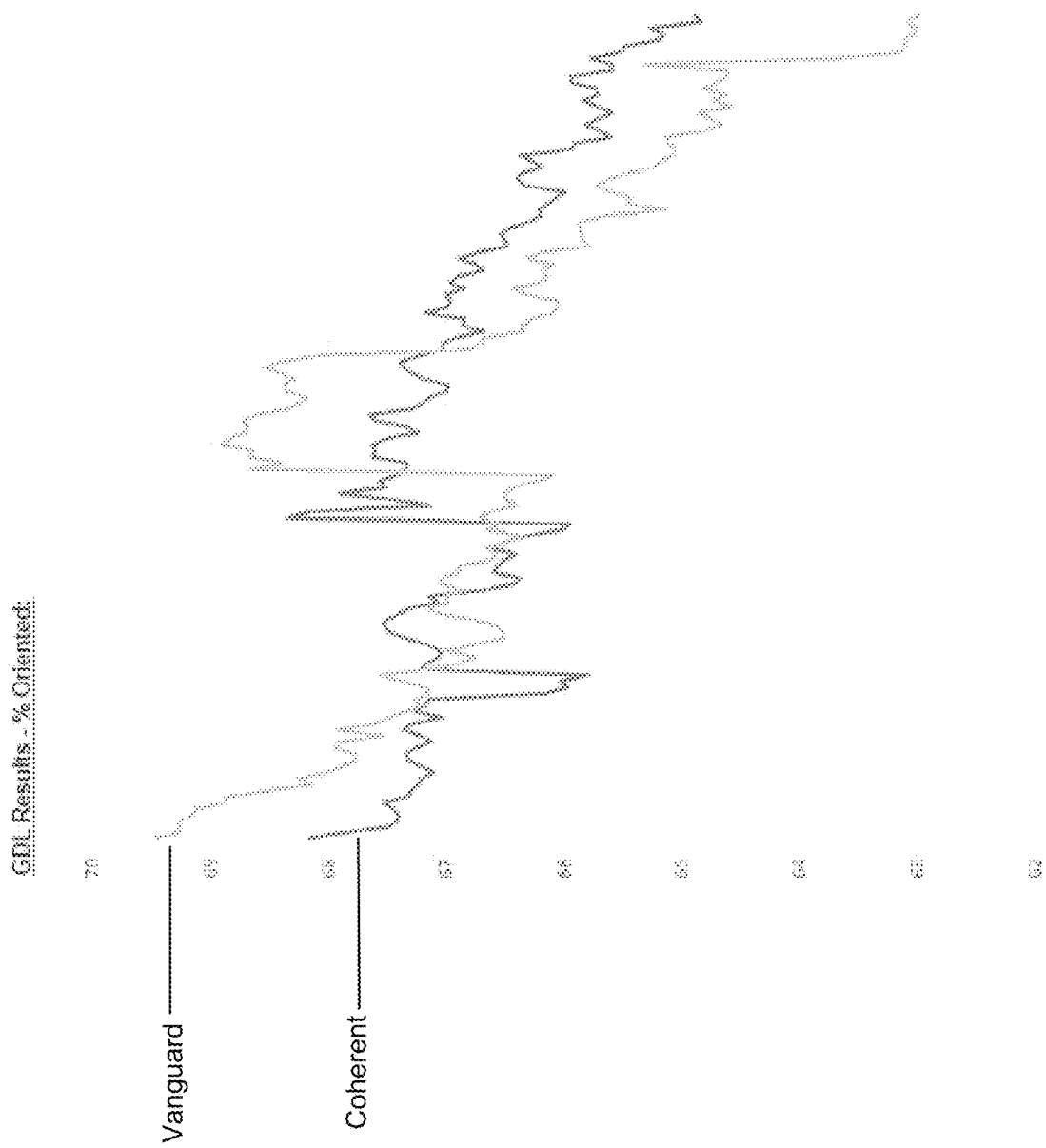
FIG. 33 shows a plot that compares percentages of sperm oriented resulting from use of a Coherent Genesis continuous wave laser or a Vanguard pulsed laser in a sorting system.

FIG. 33 shows a plot comparing percentages of sperm within the oriented region of the flow cytometer monitor resulting from use of a Coherent Genesis with the shortened beam path and continuous wave laser to the control having the Vanguard pulsed laser. Over the course of the four hour experiment the control including the Vanguard pulsed laser had instances where a higher percentage of sperm were captured in the oriented region and instances where a lower percentage of sperm were captured in the oriented region as compared to the modified sorting system including the Coherent Genesis continuous wave laser. Compared to the results of the control system with the Vanguard pulsed laser, the percentages of sperm in the oriented region resulting from use of the modified sorting system including the Coherent Genesis continuous wave laser remained more stable during the course of the four hour experiment. Indeed, the percentage of sperm in the oriented region ranged from about 64.8% to about 68.2% in the modified system with the Coherent Genesis continuous wave laser, while the percentage of sperm in the oriented region ranged from about 63% to about 69.5% for the control sorting system including the Vanguard pulsed laser.

Figure 34:
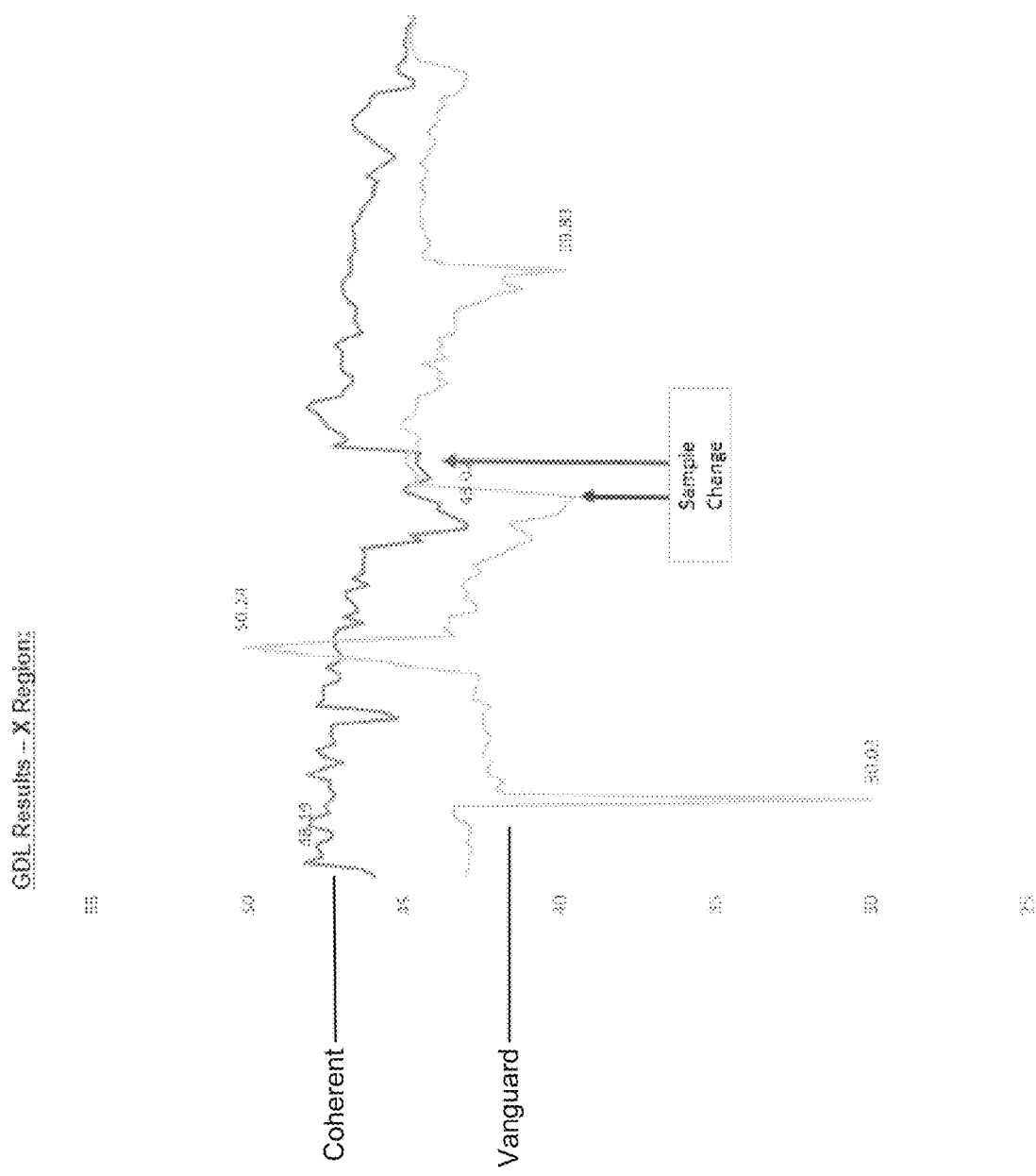
FIG. 34 shows a plot that compares amounts of sperm within an "X" sort region resulting from use of a Coherent Genesis continuous wave laser or a Vanguard pulsed laser in a sorting system.

FIG. 34 shows a plot that compares amounts of sperm within an "X" sort region resulting in the modified sorting system with Coherent Genesis continuous wave laser or the control system with the Vanguard pulsed laser. Only sperm from the oriented regions are included within the "X" sort region. The modified sorting system including the Coherent Genesis continuous wave laser remained much more stable during the course of the four hour experiment than the sorting system including the Vanguard pulsed laser with respect to the "X" sort region results. Early during the sorting comparison, a reading of 30.02 is illustrated in the control system data providing the lowest "X" sort region in the experiment and further indicating that the control system fell out of alignment. Misalignment so early during the four hour experiment is indicative of the instability of the control sorting system having conventional beam shaping optics and a conventional beam path. About half way through both sets of data each flow cytometer system was supplied with new stained sample for sorting.

Figure 35:
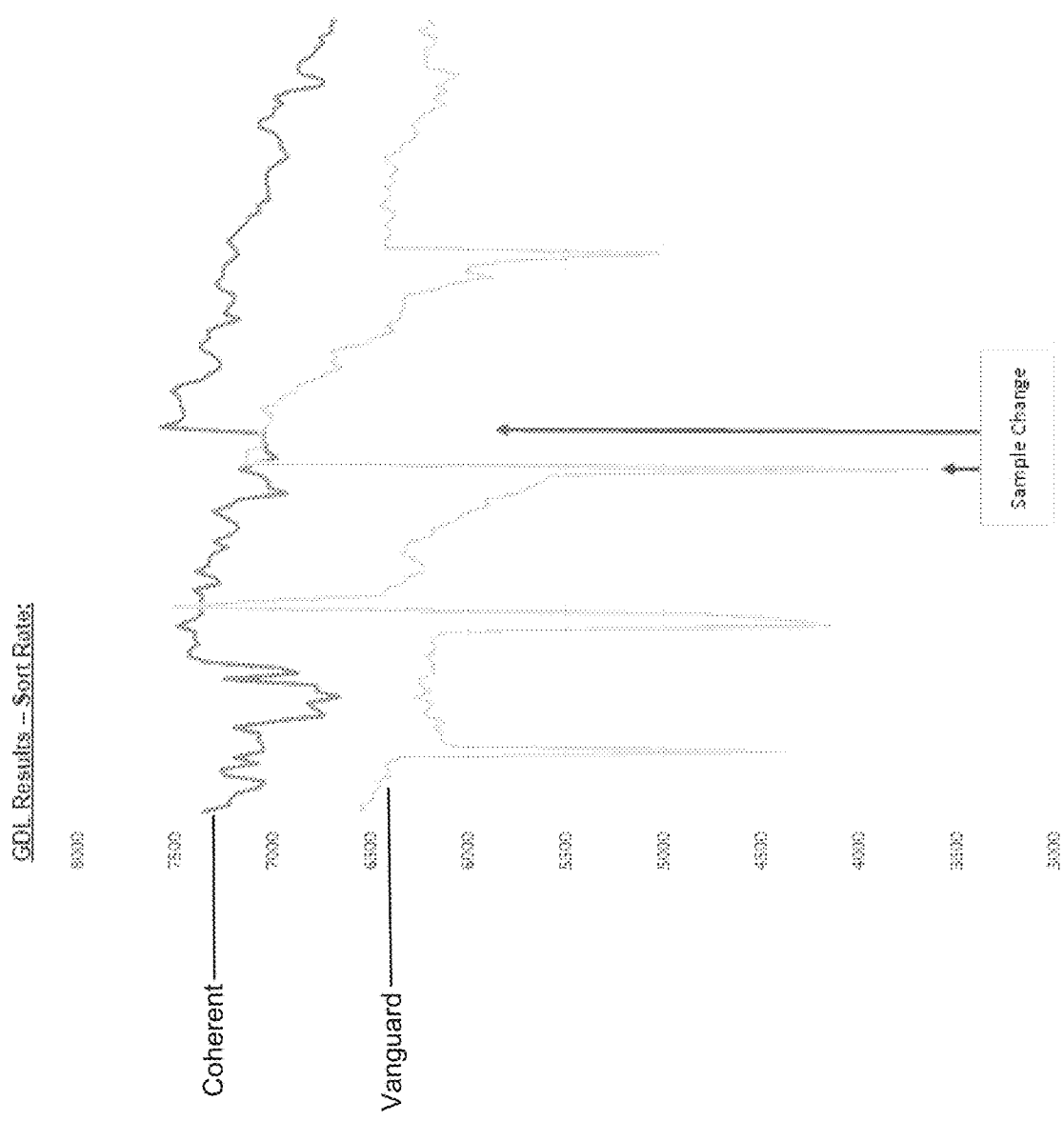
FIG. 35 shows a plot that compares sort rates of sperm resulting from use of a Coherent Genesis continuous wave laser or a Vanguard pulsed laser in a sorting system.

Referring now to FIG. 35, a plot compares sort rates of sperm resulting from use of a modified sperm sorting system with the Coherent Genesis continuous wave laser or the control system with the Vanguard pulsed laser. As shown, the modified sorting system including the Coherent Genesis continuous wave laser remained much more stable during the course of the four hour experiment than the control sorting system including the Vanguard pulsed laser with respect to the sort rate results. Indeed, the three troughs (exclusive of the sample change) indicate points where the modified sorting system including the Vanguard pulsed laser was out of alignment and required operator intervention in order to continue the experiment. Such operator intervention is indicative of the instability of the control sorting system including the conventional beam shaping optics and the conventional beam path. The modified sorting system including the Coherent Genesis continuous wave laser had an average sort rate of 7081 events per second, which was higher and more stable than the average sort rate of the control sorting system including the Vanguard pulsed laser, which was only 6191 events per second.

Figure 36:
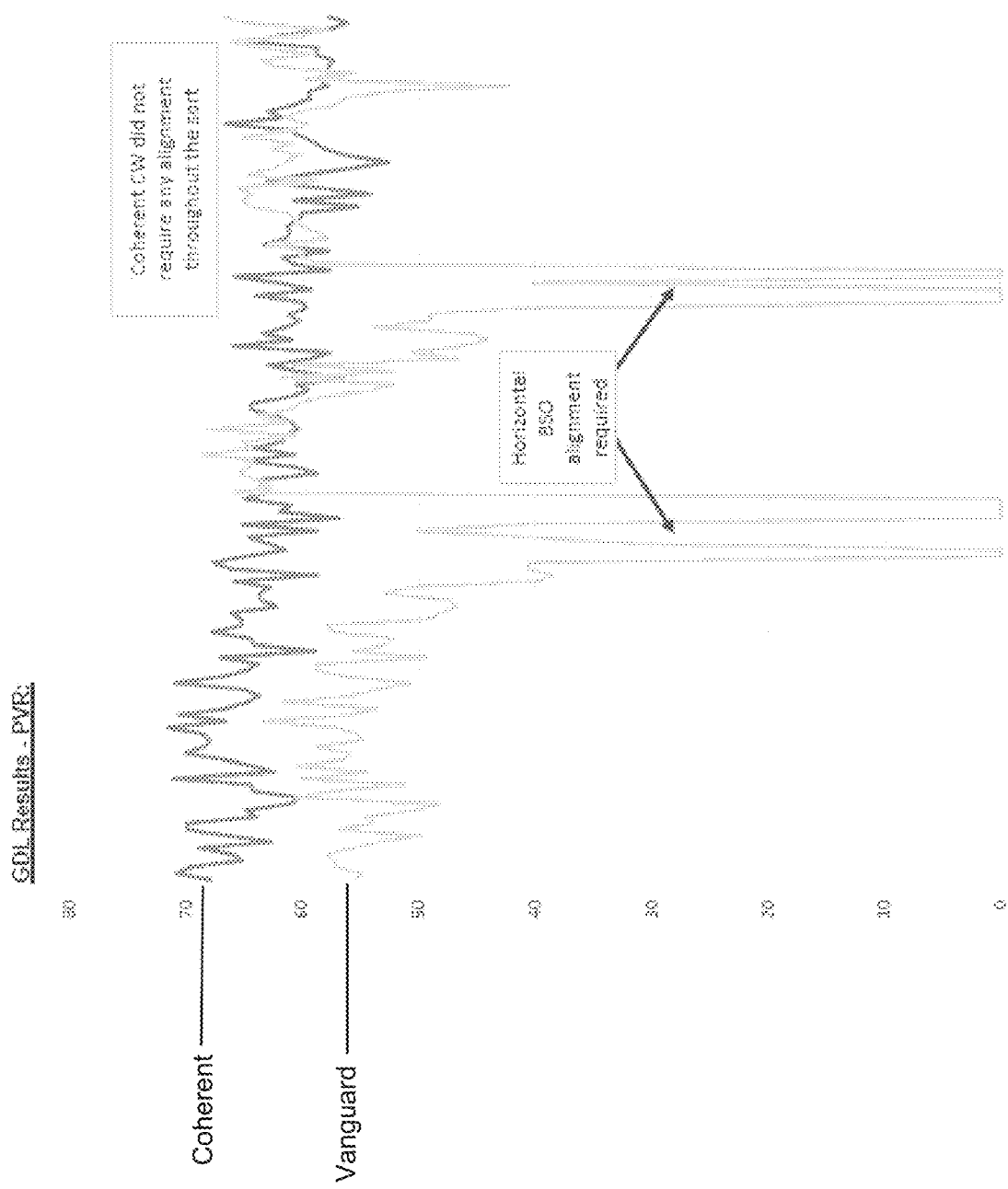
FIG. 36 shows a plot that compares PVR results from use of a Coherent Genesis continuous wave laser or a Vanguard pulsed laser in a sorting system.

FIG. 36 illustrates a plot that compares PVR results from the modified sorting system to the control sorting system. As shown, the modified sorting system including the Coherent Genesis continuous wave laser provided higher and much more stable PVR results during the course of the four hour experiment than the control sorting system including the Vanguard pulsed laser. That is, even though the PVR was constantly moving, the modified sorting system still provided a better resolution between the subpopulations of X-chromosome bearing sperm and Y-chromosome bearing sperm. As shown, modified sorting system remained generally stable throughout the experiment, and did not require any alignment or adjustments from the operator during the four hours. In contrast, however, the control sorting system required operator intervention on four instances when the alignment of the machine needed adjustment during the course of the four hour experiment. The four adjustments are indicated where the modified sorting system hit the baseline.

Figure 37:
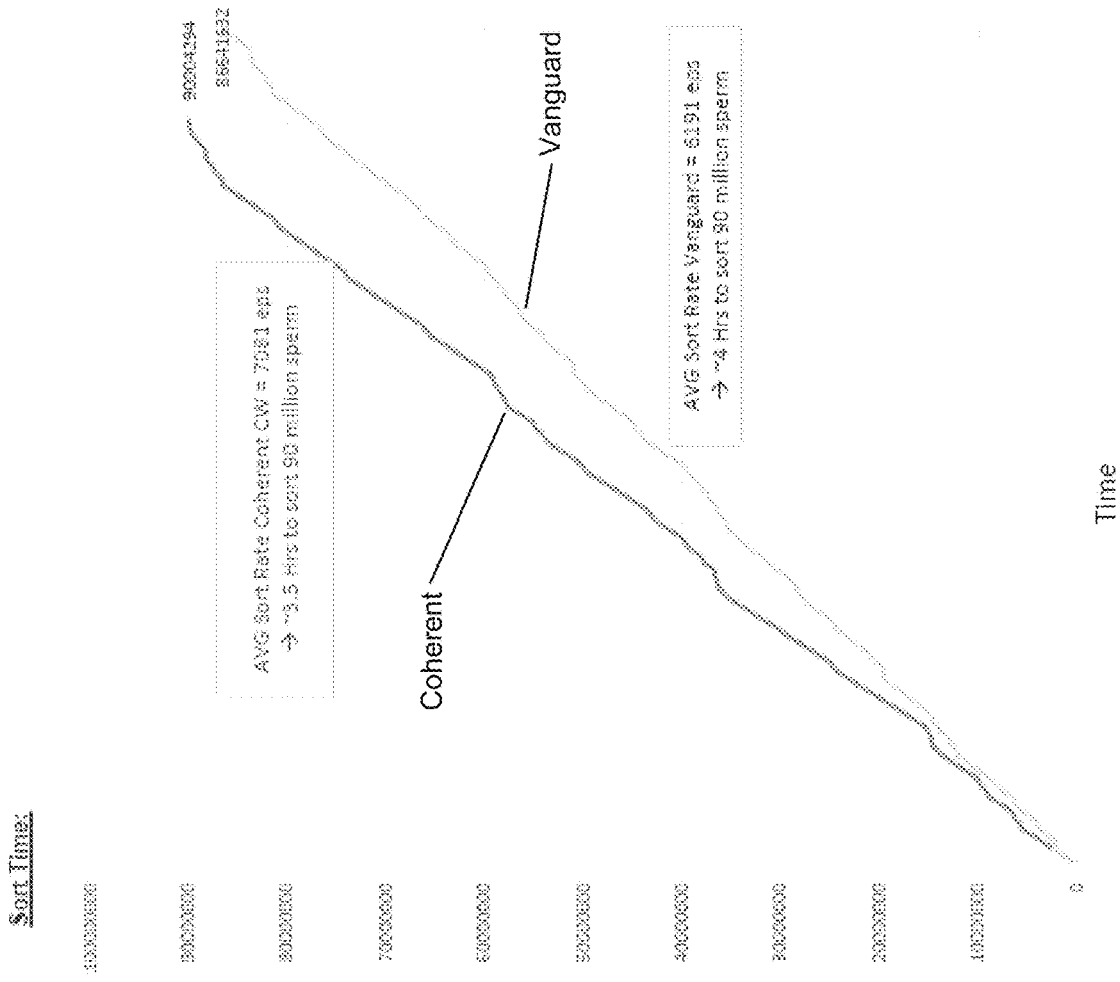
FIG. 37 shows a plot that compares sort times resulting from use of a Coherent Genesis continuous wave laser or a Vanguard pulsed laser in a sorting system.

Referring now to FIG. 37, a plot is illustrated that compares sort times resulting from use of the modified sorting system with the control sorting system. As shown, the average sort rate for the modified sorting system was 7081 events per second, and it took about 3.5 hours for the modified sorting system to sort 90 million sperm. As further shown, the average sort rate for the control sorting system was 6191 events per second, and the control sorting system was unable to sort 90 million sperm in four hours, although the sorting system came close. These results show that better performance and productivity may be achieved from use of a sorting system including a short beam path which improves beam stability and beam shaping optics having a beam width implementing beam shaping optics and shorter beam paths in accordance with one or more embodiments of the present disclosure, a more stable and more efficient sorting system may be realized.

Referring now to FIG. 38, a table that compares quality control results of pre- and post-frozen sperm that were previously sorted by a sorting system including a Coherent Genesis continuous wave laser or a Vanguard pulsed laser is shown. Specifically, these are the quality control results of sperm that were previously sorted by the four hour experiment described above with respect to FIGS. 33-37. The post-freeze results are a great indicator of the viability of the sexed sperm. Also, the sexed sperm that survive freezing are the strongest and are of the highest quality. As shown, a sorting system including a Coherent Genesis continuous wave laser produces sexed sperm that are of a quality post-freeze that is comparable to that produced by a sorting system including a Vanguard pulsed laser. Specifically, not much visual motility, viability, or PIA ("primary intact acrosome," which is indicative of the sperm's ability to fertilize), if any, is lost when a continuous wave laser is used instead of a pulsed laser in sperm sorting applications. This shows that sorting systems according to one or more embodiments of the present disclosure that include skewing systems and continuous wave lasers are capable of producing sexed sperm of good quality, and contrary to the above-described current school of thought, continuous wave lasers, at least when used in accordance with embodiments of the present disclosure, are not destroying sperm or adversely affecting sperm health and fertility.

EXAMPLE 5

Figure 39:
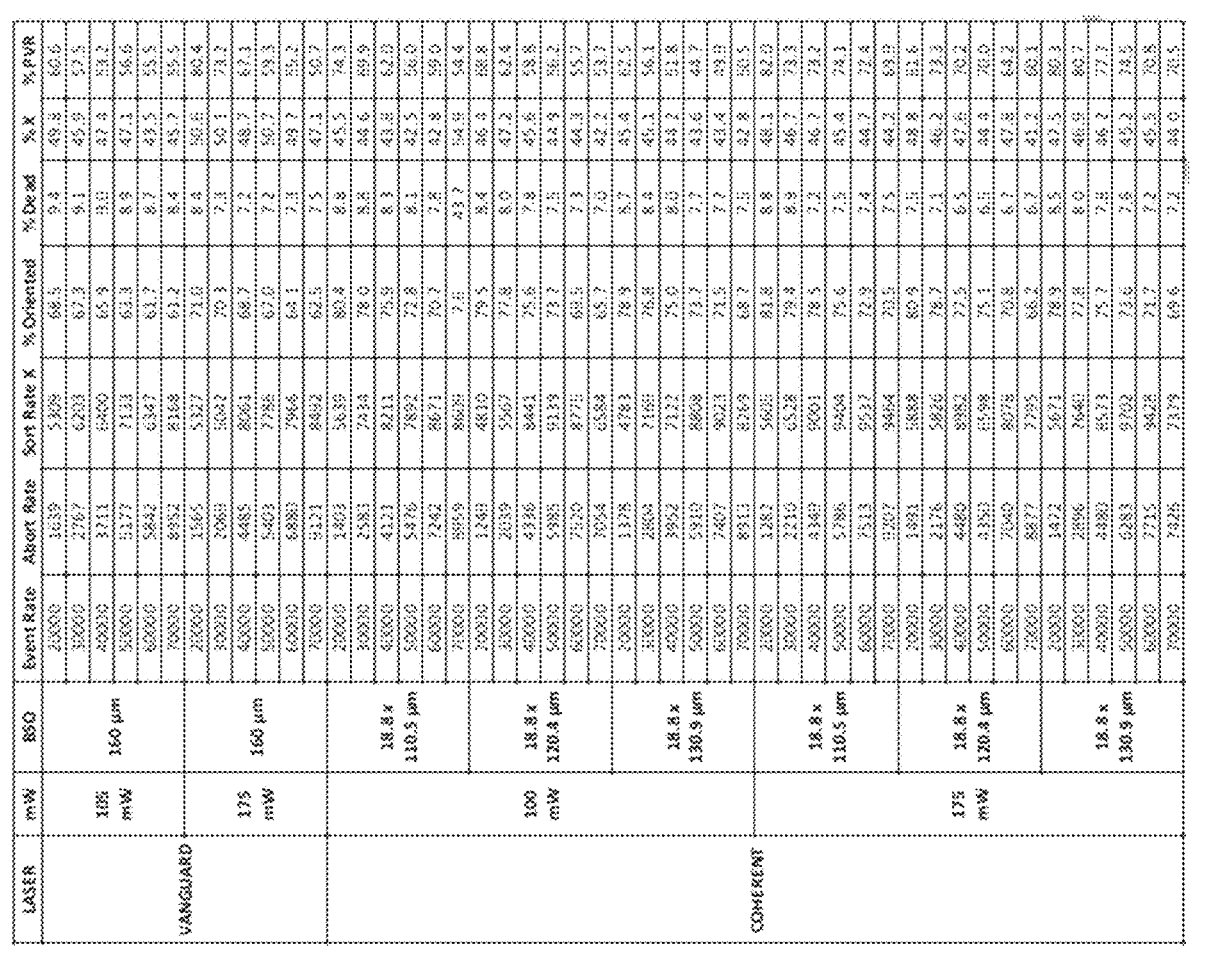
Figure 40:
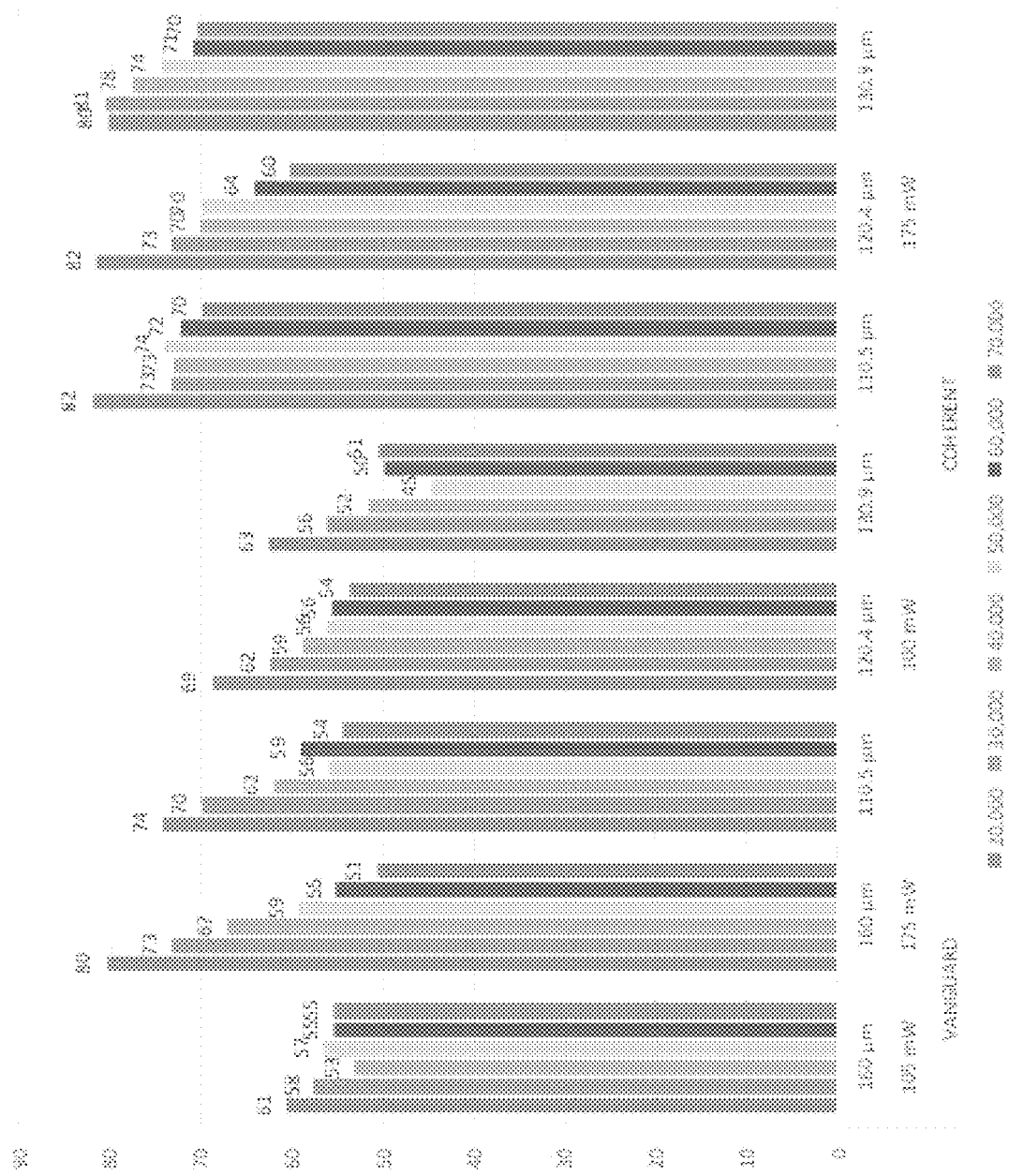
FIG. 40 shows a bar chart that compares PVR results from use of a Vanguard pulsed laser and a Coherent Genesis continuous wave laser in a sorting system across increasing event rates.

FIGS. 39-40, illustrate various results, including PVRs, obtained from an experiment comparing the sperm sorting performance of a conventional type of sorting system including a Vanguard 350-355 pulsed laser and a modified sorting system including a Coherent Genesis CX-355 continuous wave laser are shown. In the experiment, sperm originating from a single bull were stained, and the stained live sample was divided into two aliquots. One aliquot was placed on a sorting system comprising a MoFlo SX (Beckman Coulter, Miami Fla.) outfitted with a Genesis I digital upgrade (Cytonome/ST, Boston Mass.) and a Vanguard 350-355 pulsed laser. The beam path of the Vanguard was 35 inches. The other aliquot was placed on a Genesis II sorting (Cytonome/ST, Boston Mass.) that included a Coherent Genesis CX-355 continuous wave laser with a beam path of 8 inches. The goal was to monitor and record the resulting PVR of each sample in response to the different lasers at various laser powers and beam widths across a range of increasing event rates. FIG. 39 provides a table of values obtained during this experiment at a number of event rates, and powers in both systems. FIG. 40 provides a graphical representation of the PVRs obtained under each condition and correspond to the values in FIG. 39. Certain trends may be more apparent in FIG. 40, particularly understanding that each cluster of bars starts at the lowest tested event rate and progresses to the highest tested event rate.

The sorting system including the Vanguard pulsed laser was initially tested at a laser power of 105 mW with beam width set to 160 µm. At these settings, the aliquot sample was sorted for three minutes at each of the increasing event rates of 20,000 events per second, 30,000 events per second, 40,000 events per second, 50,000 events per second, 60,000 events per second, and 70,000 events per second. Next, the laser power of the sorting system was increased to 175 mW, while the beam width remained at 160 µm. At this setting, the sample was sorted for three minutes at each of the increasing event rates of 20,000 events per second, 30,000 events per second, 40,000 events per second, 50,000 events per second, 60,000 events per second, and 70,000 events per second. The results from each of these trials were recorded, as shown in FIGS. 39-40.

As shown in FIGS. 39-40, the sorting system including the Vanguard pulsed laser does not achieve acceptable PVR results at the low laser power of 105 mW. Indeed, the PVR was only in the range of 53-61 percent across event rates of 20,000 to 70,000 events per second when the power of Vanguard pulsed laser was at 105 mW. As further shown, this sorting system did, however, perform well at low event rates when the laser power was increased to 175 mW before dropping off dramatically as event rates were increased up to 70,000 events per second. Indeed, the PVR was at 80 when the event rate was 20,000 events per second but was only at 51 when the event rate was increased to 70,000 events per second.

The sorting system including the Coherent Genesis continuous wave laser was tested at a laser power of 100 mW, with a beam width set to 110.5 µm. At this setting, the aliquot sample was sorted for three minutes at each of the increasing event rates of 20,000 events per second, 30,000 events per second, 40,000 events per second, 50,000 events per second, 60,000 events per second, and 70,000 events per second. Next, the beam width was increased to 120.4 µm while the laser power remained set at 100 mW. At this setting, the aliquot sample was sorted for three minutes at each of the increasing event rates of 20,000 events per second, 30,000 events per second, 40,000 events per second, 50,000 events per second, 60,000 events per second, and 70,000 events per second. Next, the beam width was increased to 130.9 µm while the laser power remained set at 100 mW. At this setting, the aliquot sample was sorted for three minutes at each of the increasing event rates of 20,000 events per second, 30,000 events per second, 40,000 events per second, 50,000 events per second, 60,000 events per second, and 70,000 events per second. The results from each of these trials were recorded, as shown in FIGS. 39-40.

Next, the laser power of the sorting system including the Coherent Genesis continuous wave laser was increased to 175 mW, and the beam width was set at 110.5 µm. At this setting, the sample was sorted for three minutes at each of the increasing event rates of 20,000 events per second, 30,000 events per second, 40,000 events per second, 50,000 events per second, 60,000 events per second, and 70,000 events per second. Next, the beam width was increased to 120.4 µm while the laser power remained set at 175 mW. At this setting, the aliquot sample was sorted for three minutes at each of the increasing event rates of 20,000 events per second, 30,000 events per second, 40,000 events per second, 50,000 events per second, 60,000 events per second, and 70,000 events per second. Next, the beam width was increased to 130.9 µm while the laser power remained set at 175 mW. At this setting, the aliquot sample was sorted for three minutes at each of the increasing event rates of 20,000 events per second, 30,000 events per second, 40,000 events per second, 50,000 events per second, 60,000 events per second, and 70,000 events per second. The results from each of these trials were recorded, as shown in FIGS. 39-40.

As shown in FIGS. 39-40, even at the lower laser power level of 100 mW, the sorting system including the Coherent Genesis continuous wave laser was generally more stable than the sorting system including the Vanguard pulsed laser at all beam widths across increasing event rates. The beam shaping optics of the system incorporating the Genesis laser better matched the center portion of the beam width to the core stream width at a number of event rates. Additionally, the shortened beam path of 8 inches allowed for the more closely matched beam widths to be aligned with improved stability and thus improved results over a range of widths. As further shown regarding the sorting system including the Coherent Genesis continuous wave laser, the smaller beam width of 110.5 μm performed better than the larger beam widths at lower event rates of, for example, 20,000 events per second and 30,000 events per second.

FIGS. 39-40 also depict the results at the laser power level of 175 mW in the sorting system including the Coherent Genesis continuous wave laser. FIGS. 39-40 illustrate that the improved stability and particularly good resolutions were further benefited at the increased power at all beam widths across and all event rates. Indeed, insofar as a core stream width of the sample fluid increases as the event rate increases during sorting, the sorting system including the Coherent Genesis continuous wave laser set at a power level of 175 mW provided PVR results showing improved resolution over a broader range of core stream widths. The advantages of the 175 mW power level are particularly evident with respect to the beam width of 130.9 μm, or about 130 μm. As shown in FIGS. 39-40, with respect to the larger continuous wave laser beam width of 130.9 μm, the PVR results noticeably improve when the power level is increased from 100 mW to 175 mW across all event rates.

As further shown in FIGS. 39-40, the beam width of 120.4 μm, or about 120 μm, of the Coherent Genesis continuous wave laser provides excellent resolution at all event rates, as well as at a variety of laser power levels. Regarding the trials using the Coherent Genesis continuous wave laser having the beam width of 120.4 μm and the laser power of 175 mW, the inventor suspects that the sample may have run low insofar as the PVR results are less than comparable to the 110.5 μm and the 130.9 μm beam width trials. Nonetheless, these results support improved resolution with respect to beam widths in a range of about 110 μm to about 130 μm over a broader range of event rates, and correspondingly over a broader range of core stream widths.

Although the analytical instrument used to produce the PVR results shown in FIGS. 39-40 operated at event rates of either 20,000 events per second; 30,000 events per second; 40,000 events per second; 50,000 events per second; 60,000 events per second; or 70,000 events per second, it is also within the scope of the present disclosure for the analytical instrument to operate at an event rate between about 10,000 and about 20,000 events per second; between about 20,000 and about 30,000 events per second; between about 30,000 and about 40,000 events per second; between about 40,000 and about 50,000 events per second; between about 50,000 and about 60,000 events per second; between about 60,000 and about 70,000 events per second; between about 70,000 events per second and about 80,000 events per second; and between about 80,000 events per second and about 90,000 events per second.

Referring to FIG. 40, for larger trends it can be seen that in standard sorting configuration, the Vanguard at a beam width of 160 μm and a beam power of 175 mW performs drastically differently at different event rates. As the event rates increase, and the core stream width correspondingly increases, the PVRs, or sorting resolution decreases. When the power was reduced on the Vanguard to 105 mW, it can be seen that PVRs were poor at all event rates. In contrast, the modified system having incorporating the continuous wave laser and a beam width between about 110.5 μm and about 130.9 μm demonstrated excellent stability at 175 mW. At the lower power of 105 mW, the modified sorting system demonstrated improvements over the conventional sorting system operated at 110.5 μm at 120.4 μm, showing that the beam width better matched to the inner core steam width provides improved flexibility.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present disclosure, the term "a" or "an" entity refers to one or more of that entity; for example, "a fluid stream" refers to one or more of the fluid streams. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation in part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation in part application thereof or any reissue or extension thereon.

The claims set forth in this specification are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

What is claimed is:

1. A flow cytometer instrument for sperm comprising:
a flow channel that receives a sheath fluid and a sample fluid having at least one sperm to be analyzed and that creates a coaxial flow of a fluid stream having an inner core stream of the sample fluid and an outer stream of the sheath fluid, wherein the inner core stream comprises an elliptical shape with a minor axis and a major axis;
a laser that produces a laser beam;
beam shaping optics that shape the laser beam to have a beam width and a beam height at an interrogation location, wherein the beam width at the interrogation location comprises between 70 and 130 microns and no more than a center portion comprising a center half of the beam width overlaps the major axis of an inner core stream width facing the laser;
a beam path along which the laser beam traverses between the laser and the beam shaping optics;
at least one detector that generates a signal in response to electromagnetic radiation from the interrogation location; and
an analyzer that receives the signal from the at least one detector.

2. The flow cytometer instrument of claim 1, wherein the inner core stream has differing orthogonal dimensions transverse to the coaxial flow of the fluid stream, said differing orthogonal dimensions comprising the inner core stream width and an inner core stream depth.

3. The flow cytometer instrument of claim 1, wherein a beam width to beam height ratio is: between about 7:1 and about 3:1; between about 6:1 and about 4:1; between about 7:1 and about 6:1; between about 6:1 and about 5:1; between about 5:1 and about 4:1; or between about 4:1 and about 3:1.

4. The flow cytometer instrument of claim 1, wherein the beam shaping optics shape the laser beam to a beam width that is in a range of about 70 μm to about 90 μm, about 90 μm to about 110 μm, or about 110 μm to about 130 μm.

5. The flow cytometer instrument of claim 1, wherein the beam shaping optics provide substantially similar performance at event rates between 5,000 events per second and 65,000 events per second.

6. The flow cytometer instrument of claim 1, wherein the flow cytometer instrument operates at an event rate selected from the group consisting of: between about 10,000 and about 20,000 events per second; between about 20,000 and about 30,000 events per second; between about 30,000 and about 40,000 events per second; between about 40,000 and about 50,000 events per second; between about 50,000 and about 60,000 events per second; between about 60,000 and about 70,000 events per second; between about 70,000 events per second and about 80,000 events per second; and between about 80,000 events per second and about 90,000 events per second.

7. The flow cytometer instrument of claim 1, further comprising:
a plurality of additional flow channels, each additional flow channel creating an additional coaxial flow of a fluid stream having additional inner core stream of the sample fluid and an additional outer stream of the sheath fluid;
an additional laser associated with each additional flow channel that produces an additional laser beam;
additional beam shaping optics associated with each additional flow channel that shape each additional laser beam to have a beam width that substantially matches a width of the additional inner core stream facing the additional laser with which the additional beam shaping optics are associated; and
an additional beam path between each additional laser and each associated beam shaping optics,
wherein each additional beam path has a length that is less than 18 inches.

8. The flow cytometer instrument of claim 1, wherein the laser is a continuous wave laser that emits a single wavelength of electromagnetic radiation.

9. The flow cytometer instrument of claim 1, wherein the flow channel comprises a nozzle of the flow cytometer instrument.

10. The flow cytometer instrument of claim 1, wherein the at least one sperm to be analyzed is a sperm stained with a DNA selective light emission material, and wherein the DNA selective light emission material fluoresces in response to interrogation with the laser beam.

11. The flow cytometer instrument of claim 1, wherein the center portion of the beam width comprises between a center half of the beam width and a center quarter of the beam width.

12. The flow cytometer instrument of claim 1, wherein the center portion of the beam width comprises an inner most half of the beam width, an inner most third of the beam width, or an inner most quarter of the beam width.

13. The flow cytometer instrument of claim 1, wherein the beam path is less than 18 inches.

14. The flow cytometer instrument of claim 1, wherein the beam shaping optics shape the laser beam to a beam height that is in a range of 15 μm to 19 μm.

15. A method of generating a population of sperm having a skewed sex ratio of viable sperm in a flow cytometer instrument, comprising:
creating a coaxial flow of a fluid stream comprising:
an inner core stream of a sample fluid having an elliptical shape differing orthogonal dimensions transverse to the coaxial flow including a minor axis and a major axis, the sample fluid containing sperm; and
an outer stream of a sheath fluid;
modifying a laser beam from a laser into a laser beam pattern having a beam height and a beam width, wherein the beam width comprises between 70 and 130 microns;
substantially matching an inner core stream width facing the laser to a center portion of the beam width such that no more than a portion comprising a center half of the beam width overlaps the inner core stream width facing the laser;
interrogating the sperm in the inner core stream with the laser beam pattern;
detecting a response to the interrogation of the sperm;
generating at least one signal based on the detected response;
classifying a sex differentiation characteristic of the sperm based on the at least one signal; and
differentially collecting sperm or photo-ablating sperm based on the sex differentiation characteristic.

16. The method of claim 15, wherein the differing orthogonal dimensions comprise the inner core stream width and an inner core stream depth.

17. The method of claim 15, wherein a beam width to beam height ratio is: between about 7:1 and about 3:1, between about 6:1 and about 4:1; between about 7:1 and about 6:1; between about 6:1 and about 5:1; between about 5:1 and about 4:1; or between about 4:1 and about 3:1.

18. The method of claim 15, wherein the beam width is in a range of about 70 μm to about 90 μm, about 90 μm to about 110 μm, or about 110 μm to about 130 μm.

19. The method of claim 15, wherein beam shaping optics modify the laser beam to substantially match the center portion of the beam width to the inner core stream.

20. The method of claim 19, wherein the center portion of the beam width comprises between a center half of the beam width and a center quarter of the beam width.

21. The method of claim 19, wherein the center portion of the beam width comprises an inner most half of the beam width, an inner most third of the beam width, or an inner most quarter of the beam width.

22. The method of claim 21, wherein the flow cytometer instrument operates at an event rate selected from the group consisting of: between about 10,000 and about 20,000 events per second; between about 20,000 and about 30,000 events per second; between about 30,000 and about 40,000 events per second; between about 40,000 and about 50,000 events per second; between about 50,000 and about 60,000 events per second; between about 60,000 and about 70,000 events per second; between about 70,000 events per second and about 80,000 events per second; and between about 80,000 events per second and about 90,000 events per second.

23. The method of claim 15, wherein the laser beam is a continuous wave laser beam emitted at a single wavelength.

24. The method of claim 15, wherein the step of substantially matching an inner core stream width facing the laser to a center portion of the beam width provides substantially similar performance in classifying a sex differentiation characteristic of the sperm at event rates between 5,000 events per second and 65,000 events per second.

25. A multichannel flow cytometer instrument comprising:
two or more flow channels, each flow channel receiving a sheath fluid and a sample fluid having at least one sperm to be analyzed that creates a coaxial flow of a fluid stream having an inner core stream of the sample fluid and an outer stream of the sheath fluid;
a laser producing a laser beam associated with each flow channel;
beam shaping optics associated with each flow channel that shape the laser beam to a width that is in a range of 70 μm to 130 μm, the beam shaping optics producing a uniform beam shape from the laser associated with each flow channel, wherein the uniform beam shape at each flow channel provides substantially identical performance at each flow channel and wherein no more than a portion comprising the center half of the beam width overlaps the inner core stream width facing the laser;
a beam path from each laser to the associated flow channel, wherein there is no overlap in the beam paths;
at least one detector that generates a signal in response to at least one interrogated sperm; and
an analyzer that receives the signal from the at least one detector.

26. The multichannel flow cytometer instrument of claim 25, wherein each beam path is substantially the same length.

27. The multichannel flow cytometer instrument of claim 25, wherein the laser associated with each flow channel further comprises: two lasers associated with two flow channels and wherein a combined beam path length for both lasers is less than 36 inches.

28. The multichannel flow cytometer instrument of claim 25, wherein the laser associated with each flow channel further comprises: three lasers associated with three flow channels and wherein a combined beam path length for the three lasers is less than 54 inches.

29. The multichannel flow cytometer instrument of claim 25, wherein the beam shaping optics associated with each flow channel produce the uniform beam shape that has a beam width, a beam height and a beam width to beam height ratio that is: between about 7:1 and about 3:1, between about 6:1 and about 4:1; between about 7:1 and about 6:1; between about 6:1 and about 5:1; between about 5:1 and about 4:1; or between about 4:1 and about 3:1.

30. The multichannel flow cytometer instrument of claim 29, wherein the beam shaping optics associated with each flow channel shape a laser beam to substantially match a center portion of the beam width to the inner core stream.

31. The multichannel flow cytometer instrument of claim 30, wherein a center portion of the beam width comprises between a center half of the beam width and a center quarter of the beam width.

32. The multichannel flow cytometer instrument of claim 30, wherein a center portion of the beam width comprises an inner most half of a beam width, an inner most third of the beam width, or an inner most quarter of the beam width.

33. The multichannel flow cytometer instrument of claim 25, wherein the beam shaping optics shape the laser beam to a width that is in a range of about 70 μm to about 90 μm, about 90 μm to about 110 μm, or about 110 μm to about 130 μm.

34. The multichannel flow cytometer instrument of claim 25, wherein the analytical instrument operates at an event rate selected from the group consisting of: between about 10,000 and about 20,000 events per second; between about 20,000 and about 30,000 events per second; between about 30,000 and about 40,000 events per second; between about 40,000 and about 50,000 events per second; between about 50,000 and about 60,000 events per second; between about 60,000 and about 70,000 events per second; between about 70,000 events per second and about 80,000 events per second; and between about 80,000 events per second and about 90,000 events per second.

35. The multichannel flow cytometer instrument of claim 25, wherein there is no overlap or intersection of the beam paths from each laser to each associated flow channel.

36. The multichannel flow cytometer instrument of claim 25, wherein the beam shaping optics provide substantially similar performance at event rates between 5,000 events per second and 65,000 events per second.

37. A method of generating a population of sperm having a skewed sex ratio of viable sperm in a flow cytometer instrument, comprising:
creating a first coaxial flow of a fluid stream in an instrument, the first coaxial flow of the fluid stream comprising:
a first inner core stream of a sample fluid including sperm; and
a first outer stream of a sheath fluid;
generating a first laser beam along a first laser beam path;
modifying the first laser beam to a first beam pattern having a first beam width and a first beam height, wherein the first beam width is in a range of 70 μm to 130 μm;

creating a second coaxial flow of a fluid stream in the instrument, the second coaxial flow of a fluid stream comprising:
  a second inner core stream of a sample fluid including sperm; and
  a second outer stream of a sheath fluid;
generating a second laser beam along a second laser beam path, wherein the first laser beam path and the second laser beam path do not overlap;
modifying the second laser beam to a second beam pattern having a second beam width and a second beam height, wherein the second beam width is in a range of 70 µm to 130 µm;
interrogating the sperm in the first inner core stream with the first modified beam and interrogating the sperm in the second inner core stream with the second modified beam, wherein beam shaping optics associated with each channel provide a uniform beam shape and substantially identical performance at the first flow channel and the second flow channel and wherein and no more than a portion comprising the center half of the first beam width overlaps the first inner core stream width and no more than a portion comprising the center half of the second beam width overlaps the second inner core stream width;
detecting a response to the interrogation of the sperm with the first modified beam and detecting a response to the interrogation of the sperm with the second modified beam;
generating at least one first signal based on the detected response to the interrogation of the sperm in the first beam pattern and generating at least one second signal based on the detected response to the interrogation of the sperm in the second beam pattern;
classifying a sex differentiation characteristic of sperm in the first inner core stream based on the at least one first signal and classifying the sex differentiation characteristic of sperm in the second inner core stream based on the at least one second signal; and
differentially collecting sperm or photo-ablating sperm based on the sex differentiation characteristic.

* * * * *